(12) United States Patent
Croquette et al.

(10) Patent No.: US 12,061,139 B2
(45) Date of Patent: Aug. 13, 2024

(54) AUTOMATED VAULT MODULE

(71) Applicant: Azenta US, Inc., Burlington, MA (US)

(72) Inventors: Etienne Croquette, Altrincham (GB); Matteo F. Salvetti, Natick, MA (US); Rhett Affleck, Poway, CA (US)

(73) Assignee: Azenta US, Inc., Burlington, MA (US)

( * ) Notice: Subject to any disclaimer, the term of this patent is extended or adjusted under 35 U.S.C. 154(b) by 40 days.

(21) Appl. No.: 17/643,123

(22) Filed: Dec. 7, 2021

(65) Prior Publication Data

US 2022/0099541 A1    Mar. 31, 2022

Related U.S. Application Data

(62) Division of application No. 15/743,222, filed as application No. PCT/US2016/041916 on Jul. 12, 2016, now Pat. No. 11,209,344.

(Continued)

(51) Int. Cl.
| | | |
|---|---|---|
| *G01N 1/42* | (2006.01) | |
| *A01N 1/02* | (2006.01) | |

(Continued)

(52) U.S. Cl.
CPC ............. *G01N 1/42* (2013.01); *A01N 1/0257* (2013.01); *B01L 7/50* (2013.01); *F02D 3/00* (2013.01); *F25D 3/105* (2013.01); *F25D 11/02* (2013.01); *F25D 25/04* (2013.01); *G01N 35/00* (2013.01); *G01N 35/0099* (2013.01); *G01N 35/02* (2013.01); *G01N 35/04* (2013.01); *B01L 2300/1894* (2013.01); *G01N 33/48* (2013.01);

(Continued)

(58) Field of Classification Search
CPC ............. G01N 1/42; G01N 2001/1081; A01N 1/0257; B01L 7/50; F25D 3/105
See application file for complete search history.

(56) References Cited

U.S. PATENT DOCUMENTS

| | | |
|---|---|---|
| 5,233,844 A | 8/1993 | Knippscheer et al. |
| 5,921,102 A | 7/1999 | Vago |

(Continued)

FOREIGN PATENT DOCUMENTS

| | | |
|---|---|---|
| CN | 101970957 A | 2/2011 |
| CN | 102356291 A | 2/2012 |

(Continued)

OTHER PUBLICATIONS

JP-H09196528-A Translation.*

(Continued)

*Primary Examiner* — Elizabeth J Martin
(74) *Attorney, Agent, or Firm* — Hamilton, Brook, Smith & Reynolds, P.C.

(57) ABSTRACT

A cryogenic storage system provides automated storage and retrieval of samples in a cryogenic environment, as well as automated transfer of individual samples between cryogenic environments. Stored samples are maintained under a cryogenic temperature threshold, while also enabling access to the samples. The samples may be organized and tracked by scanning a barcode of each sample. The storage system can include multiple storage vaults and provide for transfer of individual samples between the storage vaults, as well as between a storage vault and a removable cryogenic storage device.

20 Claims, 66 Drawing Sheets

Related U.S. Application Data

(60) Provisional application No. 62/194,621, filed on Jul. 20, 2015.

(51) Int. Cl.

| | | |
|---|---|---|
| *B01L 7/00* | (2006.01) | |
| *F02D 3/00* | (2006.01) | |
| *F25D 3/10* | (2006.01) | |
| *F25D 11/02* | (2006.01) | |
| *F25D 25/04* | (2006.01) | |
| *G01N 33/48* | (2006.01) | |
| *G01N 35/00* | (2006.01) | |
| *G01N 35/02* | (2006.01) | |
| *G01N 35/04* | (2006.01) | |

(52) U.S. Cl.
CPC .............. *G01N 2035/00326* (2013.01); *G01N 2035/0418* (2013.01); *G01N 2035/0425* (2013.01)

(56) References Cited

U.S. PATENT DOCUMENTS

| | | |
|---|---|---|
| 2002/0023444 A1 | 2/2002 | Felder et al. |
| 2003/0037556 A1 | 2/2003 | Felder et al. |
| 2003/0196444 A1 | 10/2003 | Felder et al. |
| 2003/0233842 A1 | 12/2003 | Junca et al. |
| 2005/0016198 A1* | 1/2005 | Wowk ................ A01N 1/0268 62/457.2 |
| 2005/0183976 A1 | 8/2005 | Brothers |
| 2005/0260102 A1 | 11/2005 | Angelantoni et al. |
| 2007/0169487 A1* | 7/2007 | Seton ..................... F17C 3/08 220/560.04 |
| 2008/0092581 A1 | 4/2008 | Schumann et al. |
| 2008/0260511 A1 | 10/2008 | Fattinger et al. |
| 2010/0028214 A1 | 2/2010 | Howard et al. |
| 2010/0086440 A1 | 4/2010 | Fattinger et al. |
| 2011/0219788 A1 | 9/2011 | Zimmermann et al. |
| 2011/0225984 A1 | 9/2011 | Brooks |
| 2012/0060514 A1 | 3/2012 | Warhurst et al. |
| 2012/0060539 A1 | 3/2012 | Hunt et al. |
| 2013/0302097 A1 | 11/2013 | Blenkinsop et al. |
| 2015/0204598 A1 | 7/2015 | Affleck et al. |
| 2018/0202908 A1 | 7/2018 | Croquette et al. |

FOREIGN PATENT DOCUMENTS

| | | | |
|---|---|---|---|
| JP | H09196528 A | * | 7/1991 |
| JP | 2005289597 A | | 10/2005 |
| JP | 2005289598 A | | 10/2005 |
| JP | 2008169042 A | | 7/2008 |
| JP | 2008292461 A | | 12/2008 |
| JP | 2010083679 A | | 4/2010 |
| JP | 2012056730 A | | 3/2012 |
| JP | 2013508237 A | | 3/2013 |
| JP | 2014009089 A | | 1/2014 |
| JP | 2014148415 A | | 8/2014 |
| JP | 2015013736 A | | 1/2015 |
| WO | 2015021295 A2 | | 2/2015 |
| WO | 2015109315 A2 | | 7/2015 |

OTHER PUBLICATIONS

International Search Report and Written Opinion of the International Searching Authority mailed Nov. 16, 2016 from International Application No. PCT/US2016/041916 filed Jul. 12, 2016, entitled "Automated Vault Module".

Notification Concerning Transmittal of Copy of International Preliminary Report on Patentability of Int'l Application No. PCT/US2016/041916; Date Mailed: Feb. 1, 2018, entitled "Automated Vault Module".

* cited by examiner

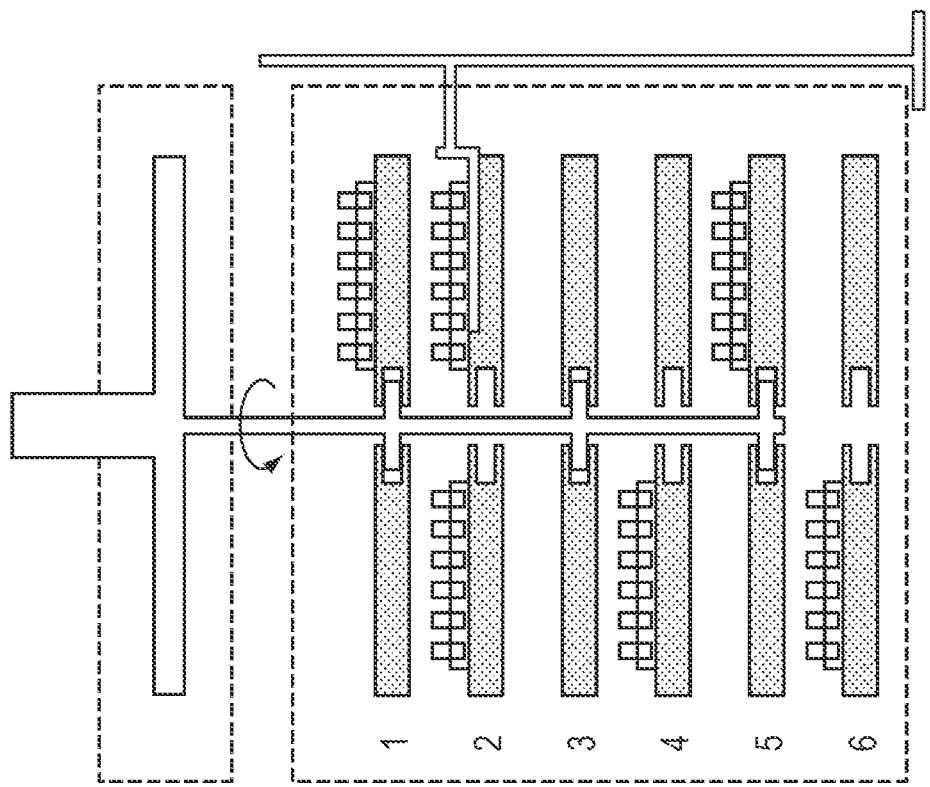
FIG. 20H
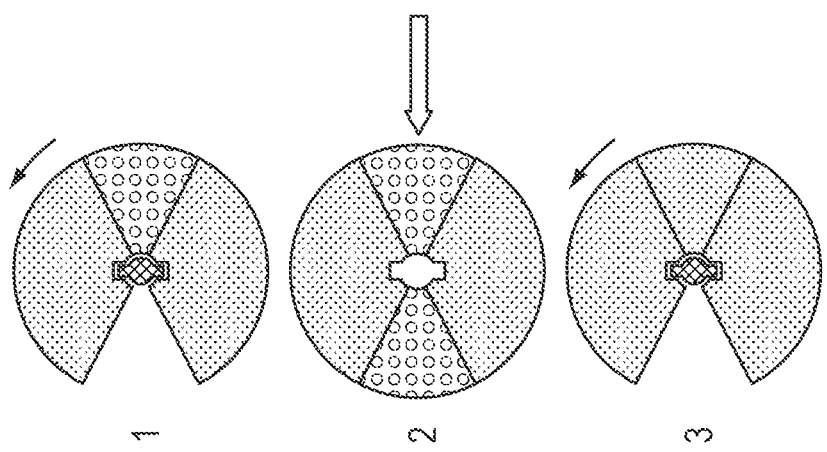

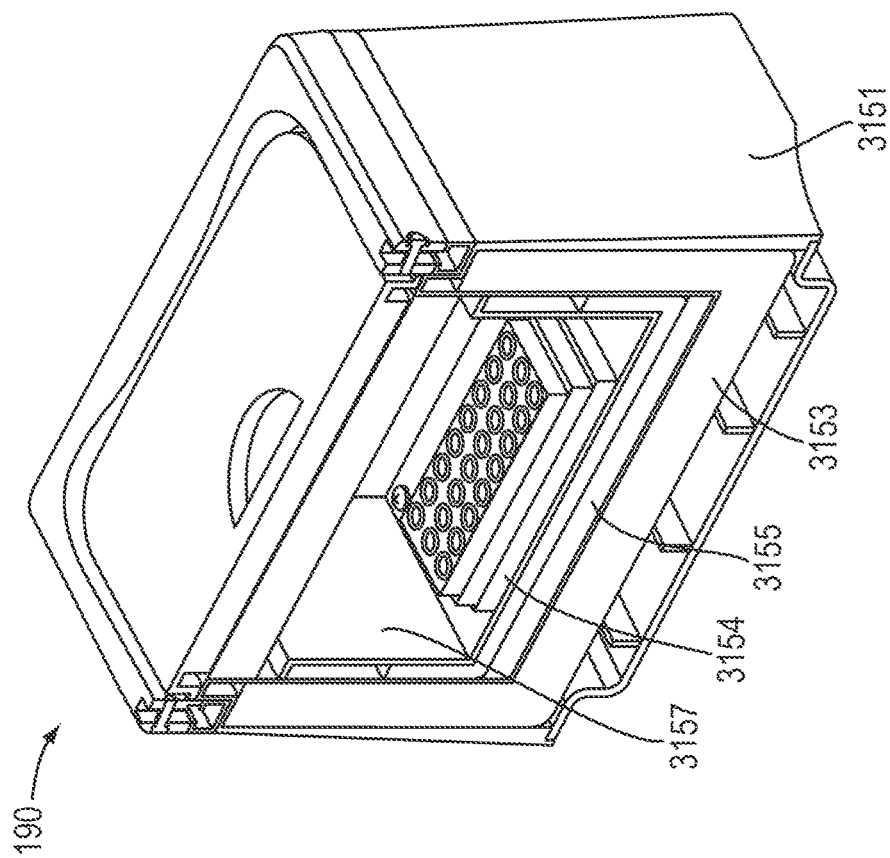
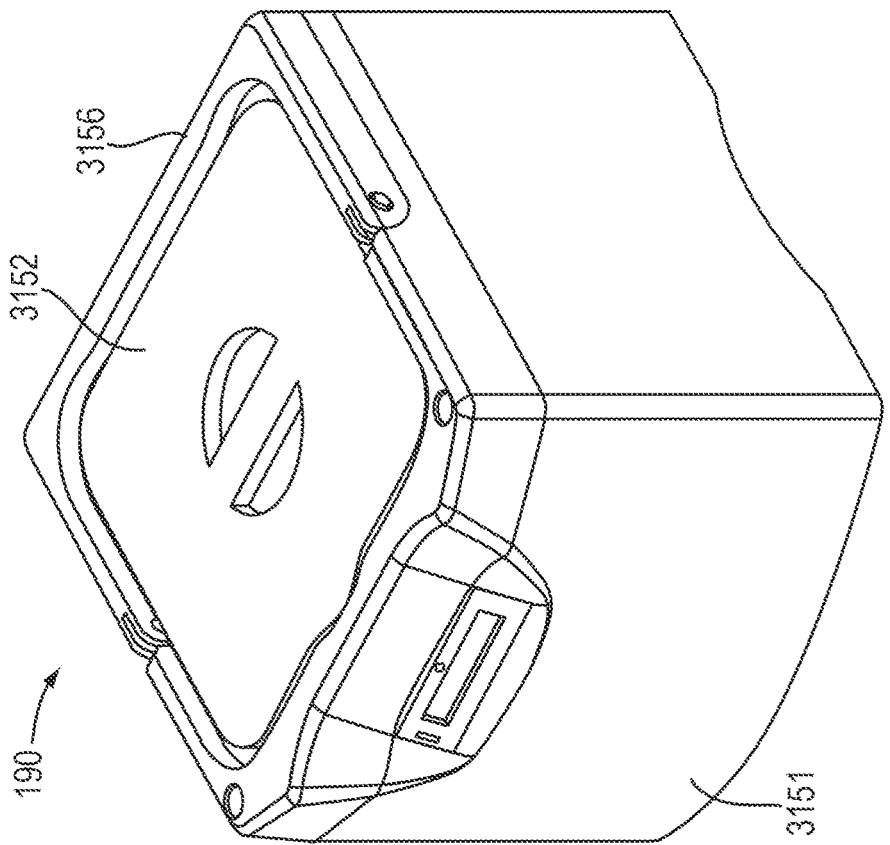
FIG. 31B
FIG. 31A

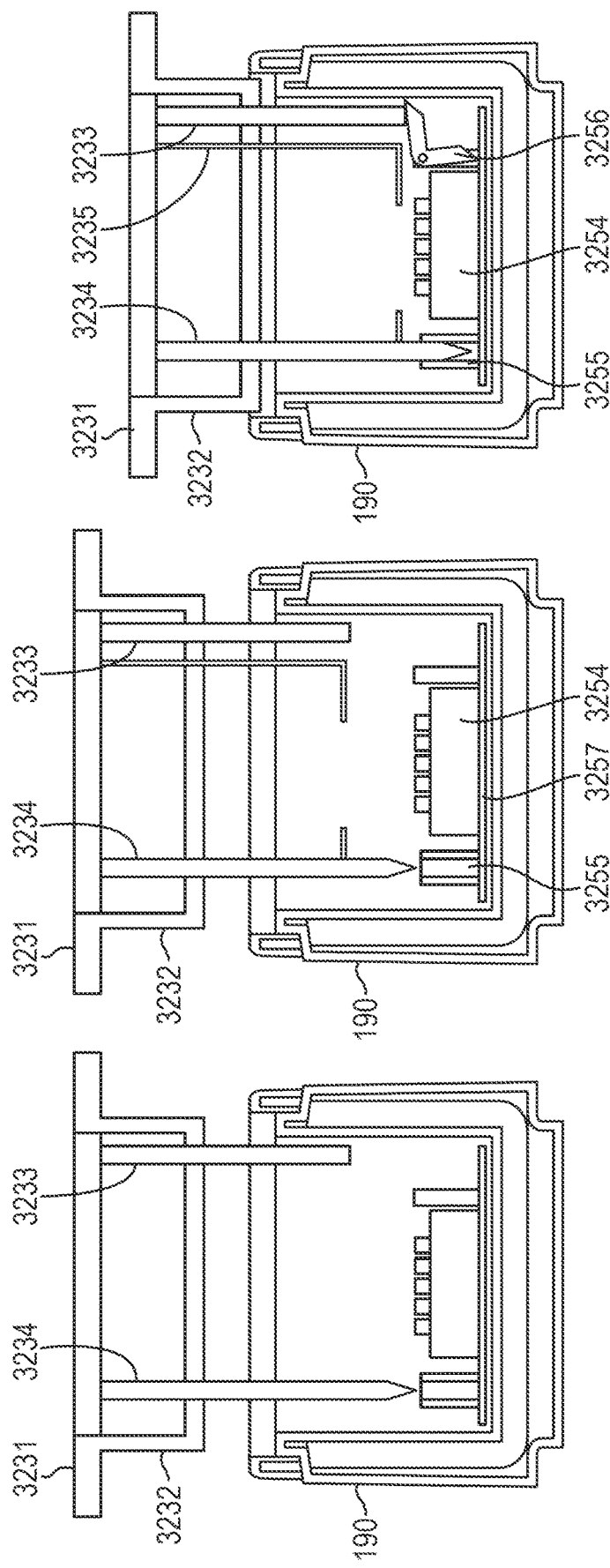

AUTOMATED VAULT MODULE

RELATED APPLICATION

This application is a divisional of U.S. application Ser. No. 15/743,222, filed Jan. 9, 2018, which is the U.S. National Stage of International Application No. PCT/US2016/041916, filed Jul. 12, 2016, which designates the U.S., published in English, and claims the benefit of U.S. Provisional Application No. 62/194,621, filed on Jul. 20, 2015. The entire teachings of the above applications are incorporated herein by reference.

BACKGROUND

Cryopreservation is a process essential to maintaining the integrity of biological substances over extended periods of storage. At sufficiently low temperatures, all chemical processes and biological functions of such substances are effectively halted, allowing them to be stored safely over nearly any length of time. A cryogenic storage dewar enables such storage by providing an insulated and controlled cryogenic environment to accommodate a number of biological or other samples. In typical storage dewars, samples are loaded into racks or trays, each of which hold several samples. The racks or trays are manually removed from the cryogenic environment of the dewar, presenting the rack or tray to a user for removing samples from, or adding samples to, the storage dewar.

SUMMARY

Example embodiments of the invention provide automated storage and retrieval of samples in a cryogenic environment, as well as automated transfer of individual samples between cryogenic environments. Embodiments can provide for maintaining samples under a cryogenic temperature threshold (e.g., −134° C.) at all times, while also enabling access to samples at all times. The samples may be organized and tracked by scanning a barcode of each sample. Embodiments may also comprise multiple storage vaults and provide for transfer of individual samples between the storage vaults, as well as between a storage vault and a removable cryogenic storage device.

In one embodiment, a cryogenic storage system comprises one or more storage vaults that provide for storing a plurality of samples in a cryogenic environment. A sample handling module is configured to transfer automatically individual samples between a cryogenic environment of the storage vault and another cryogenic environment, which may be encompassed by a removable storage device or by a further storage vault. The sample handling module may move the sample quickly through a non-cryogenic environment while maintaining the sample under the cryogenic temperature threshold.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 20A-M are schematic illustrations of the process of retrieving a sample as shown in FIG. 19.

FIGS. 31A-B are illustrations of a removable cryogenic storage device in accordance with aspects of the disclosed embodiment.

FIGS. 32A-D are illustrations of the interface between a sample handling module and a removable cryogenic storage device in accordance with aspects of the disclosed embodiment.

DETAILED DESCRIPTION

Figure 1A:
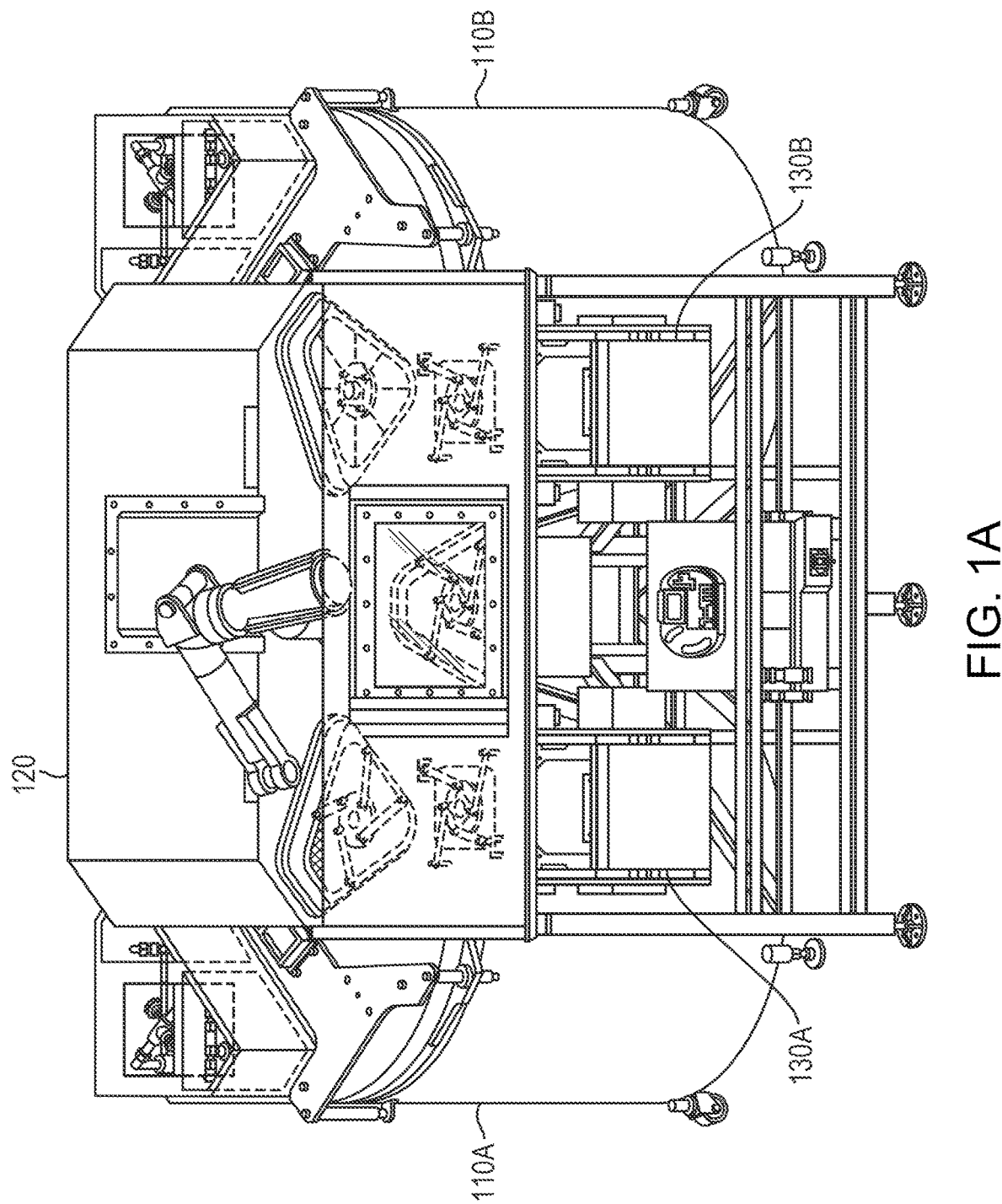
FIGS. 1A-C illustrate an automated cryogenic storage system in one embodiment.
Figure 1B:
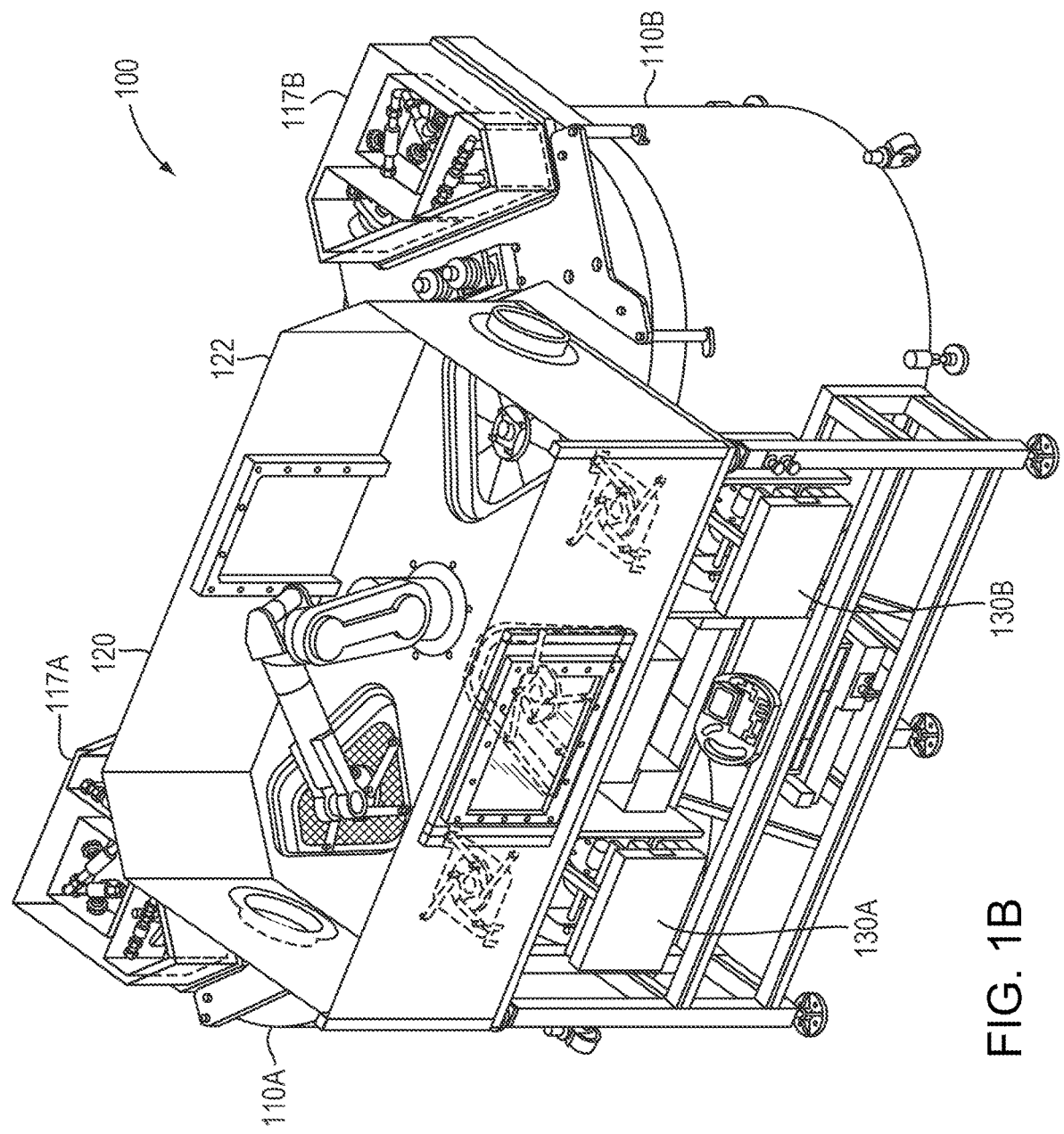
Figure 1C:
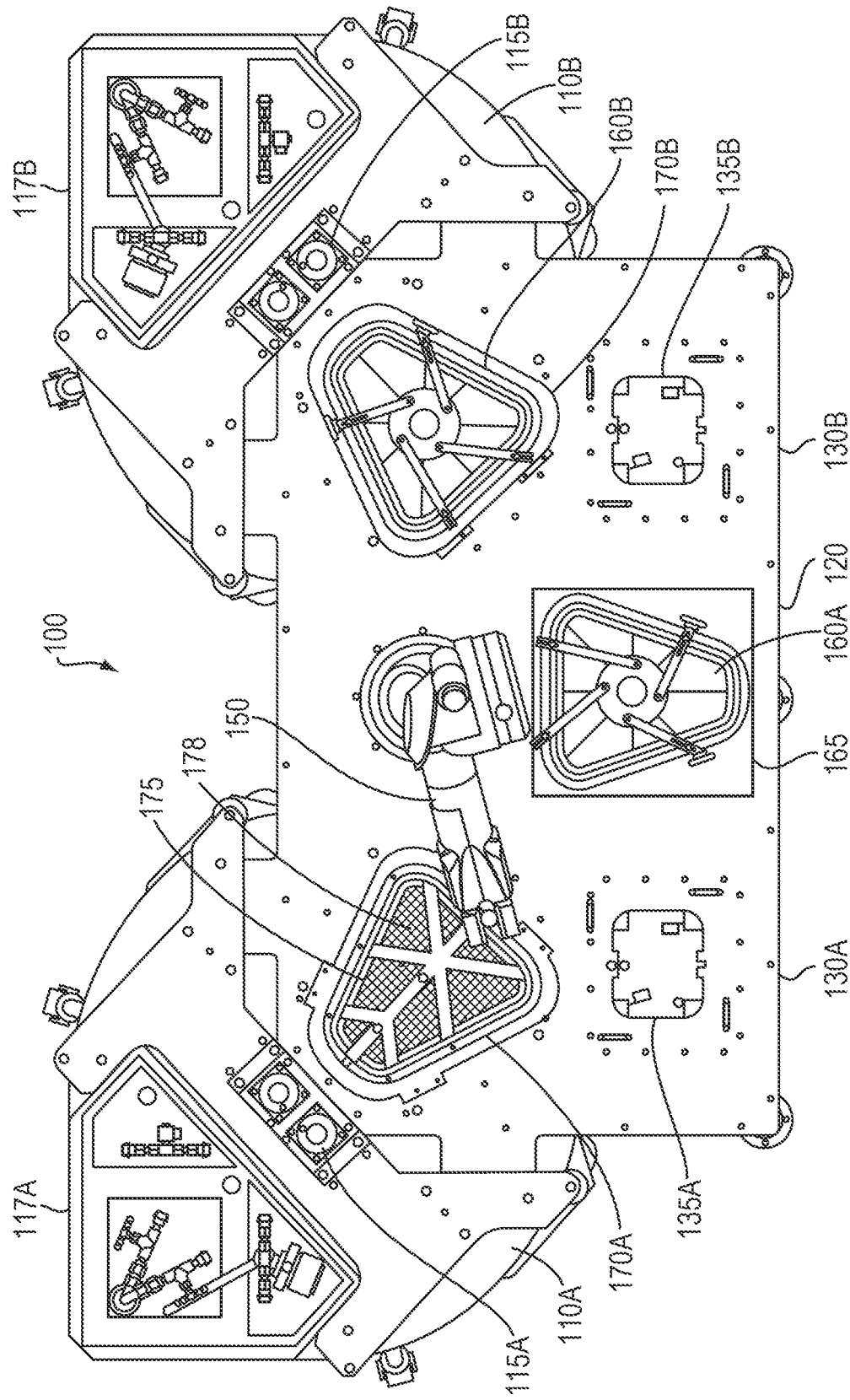

FIGS. 1A-C illustrate an automated cryogenic storage system 100 in one embodiment. FIG. 1A shows a top-front view of the system 100, which includes a first storage vault 110A, a second storage vault 110B, and a sample handling module (SHM) 120. The SHM 120 further includes external ports 130A-B. The storage vaults 110A-B each provide for storing a substantial number (e.g., 25,000) of samples (e.g., a biological or chemical sample contained in a sealed vial) in a cryogenic environment, thereby maintaining the samples below a respective glass transition temperature $T_G$. The SHM 120 connects to the first and second storage vaults 110A-B and the external ports 130A-B to which a device housing a removable cryogenic storage device (e.g., a portable cryogenic workstation, described below) may be docked. The SHM 120 may also facilitate transfer of samples between the storage vaults 110A-B, or between external ports 130A-B. In alternative embodiments, the system 100 may include a single storage vault 110, greater than two storage vaults 110, or any number of external ports 130.

FIG. 1B illustrates the system 100 in an isometric view. Here, refrigerant ports 117A and 117B of storage vaults 110A and 110B, respectively, are more clearly visible. Refrigerant ports 117A-B connect to a refrigerant supply (e.g., one or more nitrogen tanks, not shown) for channeling the entry of refrigerant to the system 100. Further, the SHM 120 includes an enclosure 122 connecting the storage vaults 110A-B and housing additional components of the SHM 120, described in further detail below.

FIG. 1C provides a top-down view of the system 100, with the enclosure 122 removed, including components internal to the enclosure 122 of the SHM 120. In particular, a samples between any combination of the storage vaults 110A-B and a device (e.g., a portable cryogenic workstation) docked at the external ports 130A-B. The robotic arm 150 accesses the storage vaults 110A-B and external ports 130A-B via respective openings at the floor of the enclosure 122. Specifically, openings 135A-B enable the robotic arm to access devices docked at external ports 130A-B, respectively. The opening 135A-B may be secured and sealed by removable covers (not shown). Further, each storage vault 110A-B connects to the enclosure 122 via respective openings 170A-B, each of which are secured and sealed by respective covers 160A-B when a transfer is not occurring. External to the enclosure 122, each of the storage vaults 110A-B includes a respective set of motors 115A-B for driving sample transfers within the vaults 110A-B. The set of motors 115A-B may be located external to the respective storage vaults 110A-B in order to isolate the temperature-sensitive components of the motors 115A-B from the cryogenic environments within the storage vaults 110A-B, as well as to allow repair and replacement of the motors 115A-B without disrupting the cryogenic environments.

The system 100 is illustrated in FIG. 1C during a transfer of a sample 178. To accomplish this transfer, the cover 160A of the storage vault 110A has been removed and placed at the cover park 165. The vault 110A has elevated a tray 175 containing individual samples 178 to the opening 170A of the enclosure 122. As a result, the robotic arm 150 may select and remove a single one of the individual samples 178 and transfer the sample 178 either to a device docked at one of the external ports 130A-B or to the other storage vault 110B. Conversely, the robotic arm 150 may also transfer individual samples 178 to the tray 175 from any of the external ports 130A-B or the other storage vault 110B.

Figure 2:
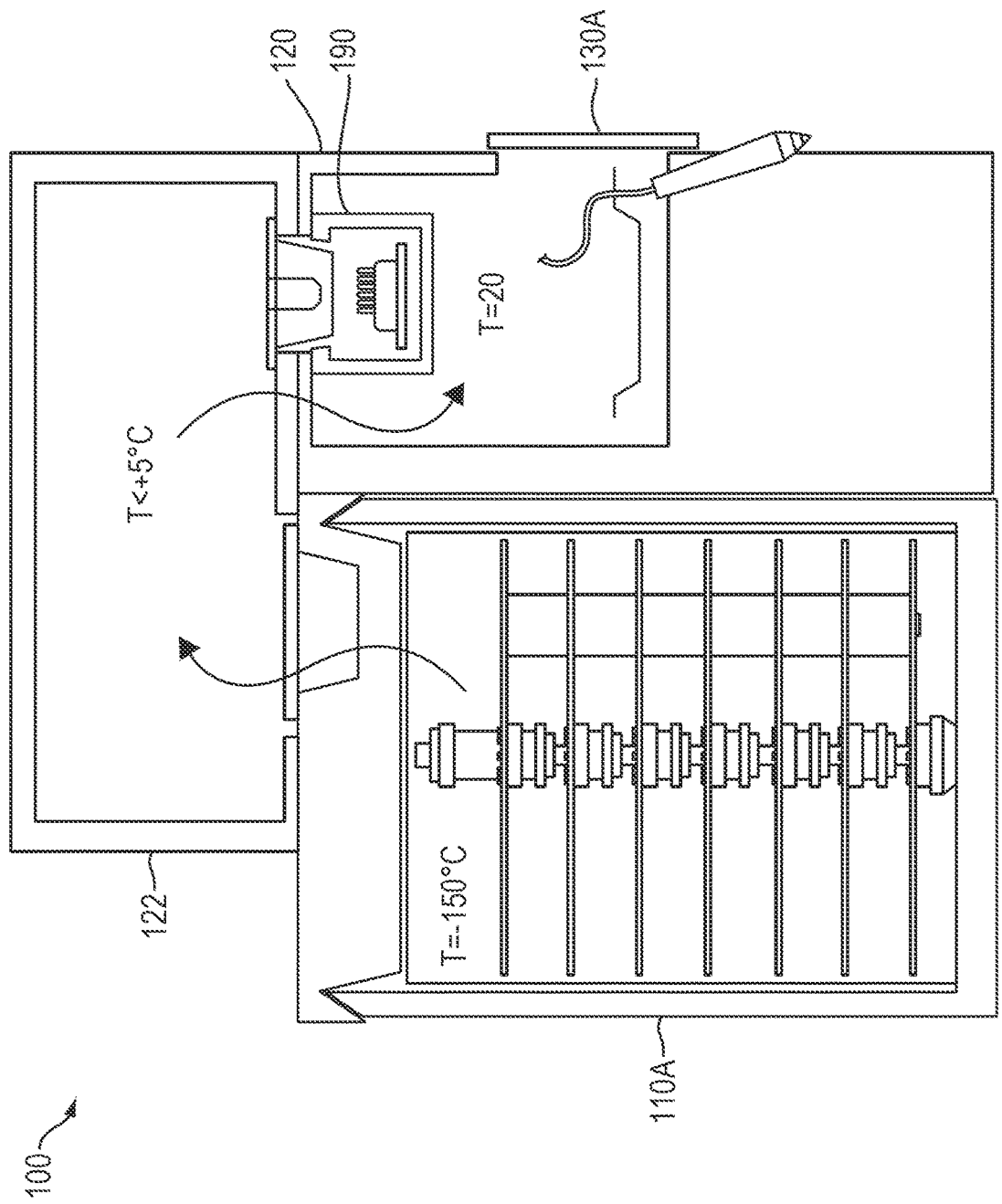
FIG. 2 is a schematic illustration of resulting refrigeration of chambers within a the embodiment of FIGS. 1A-C.

FIG. 2 is a schematic illustration of example target refrigeration levels within the system 100. The storage vault 110A (as well as the storage vault 110B, not shown) may maintain a cryogenic environment such as a temperature of −150° C. In contrast, the enclosure 122 of the SHM 120 may maintain a non-cryogenic environment having a temperature comparable to an ambient temperature, and may further control the environment to reduce moisture within the enclosure 122. Alternatively, the environment within the enclosure 122 may be cooled to below ambient temperature such as, for example, less than about 5° C. The external port 130A (as well as the port 130B, not shown) may likewise maintain a non-cryogenic environment (e.g., a temperature of about 20° C.). However, a device docked to the external port 130A, such as the portable cryogenic workstation 190, may maintain an internal cryogenic environment for storing samples 178.

Figure 3:
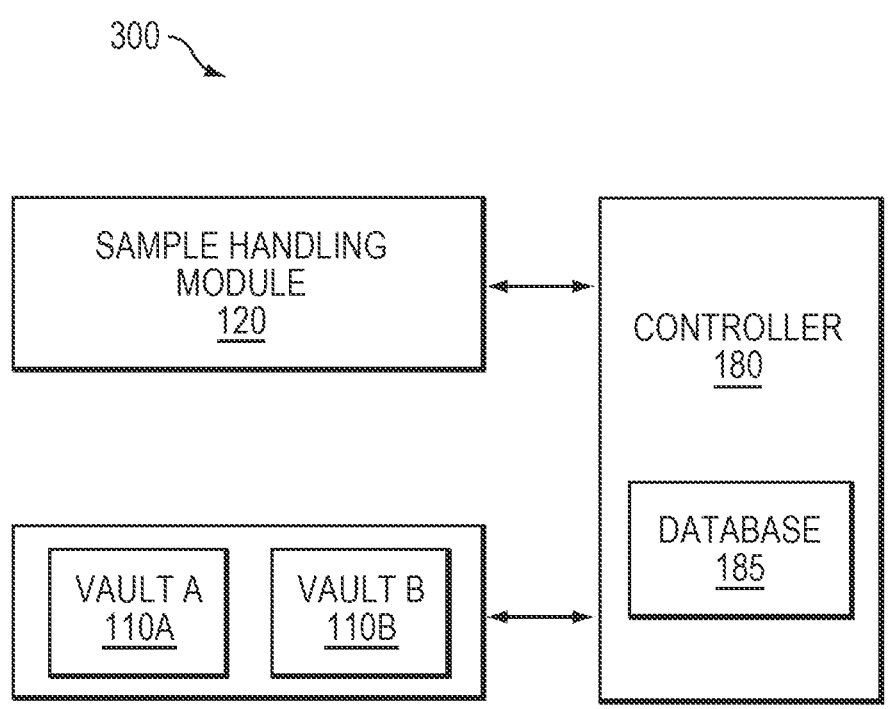
FIG. 3 is a block diagram of a cryogenic storage system including a controller in a further embodiment.

FIG. 3 is a block diagram of a cryogenic storage system 300 in a further embodiment. The system 300 may include the features of the cryogenic storage system 100 described above with reference to FIGS. 1-2, including the SHM 120 and storage vaults 110A-B, and further includes a controller 180. The controller 180 may be connectively coupled to the SHM 120 and storage vaults 110A-B, and generally controls some or all of the operations of each. For example, the controller 180 may control the storage vaults 110A-B to move sample trays 175 within each vault 110A-B to present a given sample 178 for retrieval. The controller 180 may also control the SHM 120 to transfer samples 178 between the storage vaults 110A-B and external ports 130A-B. In addition to controlling the transfer of samples 178, the controller 180 may also monitor and control refrigeration and humidity levels of the SHM 120 and storage vaults 110A-B, and may control other operations such as calibration of mechanical components, identifying samples, and failure or disaster recovery. Further, the controller 180 may maintain a database 185 storing information regarding the samples 178 stored within the storage vaults 110A-B, including the location of each sample 178 within the storage vaults 110A-B. The controller 180 may update the database 185 in response to the transfer of samples 178 into or out of the storage vaults 110A-B.

To provide such control operations, the controller 180 may include suitable computer hardware and software resources, such as one or more computer workstations and an interface configured for communication with the SHM 120 and storage vaults 110A-B. The controller 180 may also include an interface (e.g., a workstation) allowing a user to monitor the system 300 as well as monitor and/or initiate the aforementioned operations of the system 300.

Figure 4:
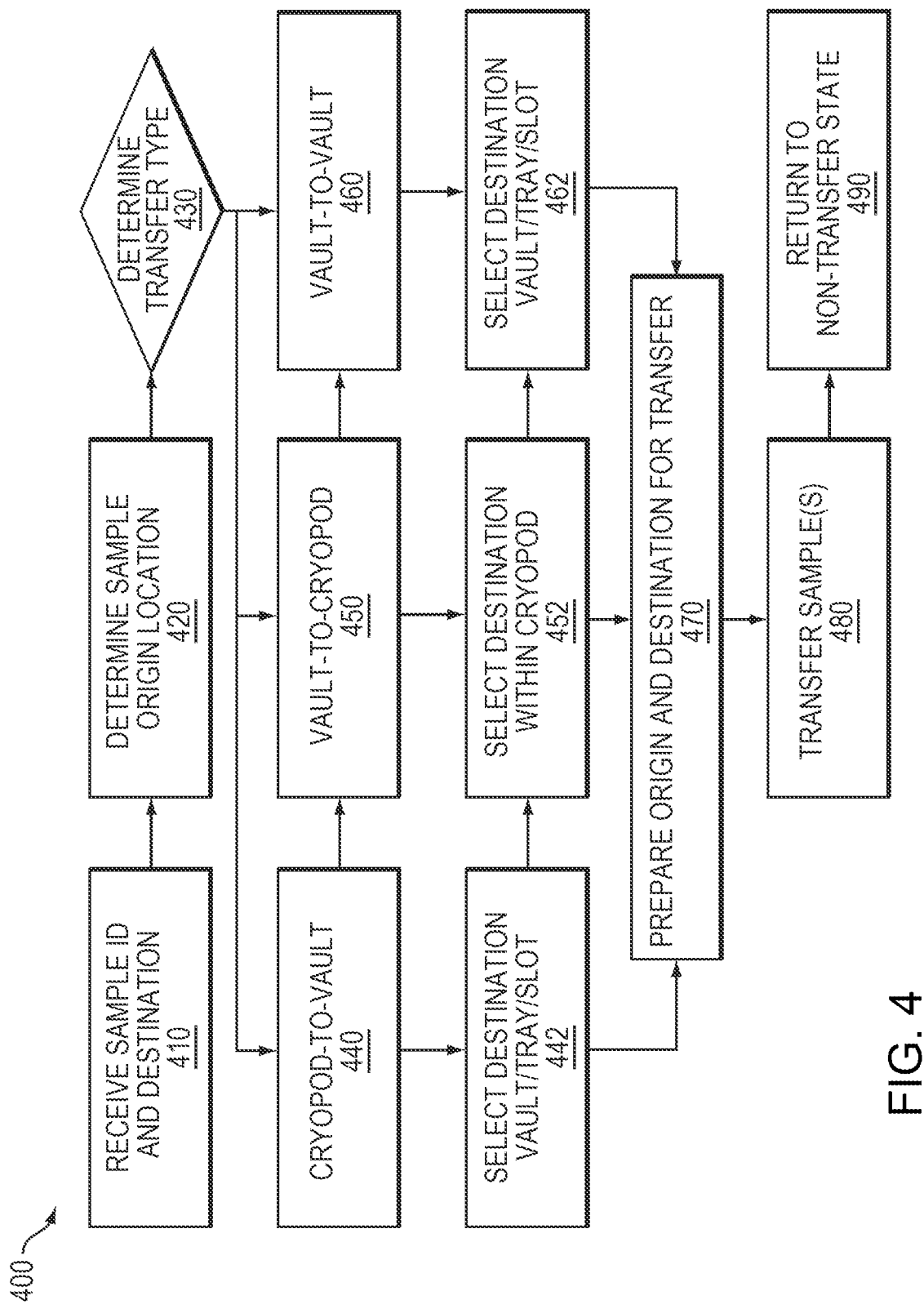
FIG. 4 is a flow diagram illustrating a process of transferring individual samples in one embodiment.

FIG. 4 is a flow diagram illustrating a process 400 of transferring individual samples 178, which may be carried out by either of the systems 100, 300 described above with reference to FIGS. 1-3. With reference to FIG. 3, the controller 180 may receive a sample identifier (ID) and intended destination for one or more samples 178 to be transferred (410). For each sample to be transferred, the controller 180 may access the database 185 to determine the present location (origin) of the sample 178, including an address of the sample within one of the storage vaults 110A-B or a portable cryogenic workstation 190 (FIG. 2) (420). Based on the determined origin and destination of the sample 178, the controller 180 may then determine a type of transfer to take place (430): a portable cryogenic workstation-to-vault transfer (440), a vault-to-portable cryogenic workstation transfer (450), or a vault-to-vault transfer (460). In alternative embodiments, a portable cryogenic workstation-to-portable cryogenic workstation transfer may also be completed.

For a portable cryogenic workstation-to-vault transfer (440), the controller selects a destination address within one of the storage vaults 110A-B (442). The address may indicate a given tray 175 and slot within a given storage vault 110A-B. For a vault-to-portable cryogenic workstation transfer (450), the controller 180 may select a destination slot within the portable cryogenic workstation 190 (452). For a vault-to-vault transfer (460), the controller selects an address within the destination storage vault 110A-B (462). The controller 180 may update the database 185 to indicate the selection of a destination address within a storage vault 110A-B or a portable cryogenic workstation 190.

For all sample transfers, both the origin and destination undergo a respective operation to prepare the origin and destination for the transfer (470). For a vault 110A-B, the controller 180 may command the vault 110A-B to present the tray 175 containing the sample 178 or the sample slot to the SHM 120. Likewise, a portable cryogenic workstation 190 may be elevated within an external port 130A-B to expose its enclosure to the SHM 120. Once both the origin and destination are prepared, the SHM 120 transfers the individual sample 178 from the origin to the destination (480). In doing so, the SHM 120 may move the sample 178 through a non-cryogenic environment, in particular the environment contained within the enclosure 122 of the SHM 120. However, the SHM 120 may move the individual sample 178 quickly (e.g., in fewer than 5 seconds) to prevent the sample 178 from reaching a temperature above the glass transition temperature $T_G$ of the sample (described in further detail below). The controller 180 may also verify the identity of the sample 178 before, during and/or after the transfer by scanning an identifying mark (e.g., a barcode) of the sample by a sensor within the storage vaults 110A-B and/or the SHM 120.

Following transfer of the sample 178, the controller 180 may determine whether additional samples 178 are to be transferred between the same origin and destination, and particularly regarding the same storage tray(s) 175 being presented to the SHM 120. If so, further transfers may be conducted accordingly (480). Such transfers may occur, for example, if multiple associated samples 178 are to be transferred simultaneously, and are stored within a common tray 175 for more efficient transfer. Following all such transfers, the origin and destination return to their state prior to the transfer (490). For example, the storage vault cover(s) 160A-B may be replaced, and the presented tray 175 is returned to its original location within the storage vault 110A-B. Likewise, a portable cryogenic workstation 190 may be sealed and prepared for removal from an external port 130A-B. Upon verifying a successful transfer, the controller 180 may update the database 185 to indicate the location of newly added or removed samples 178.

Figure 5A:
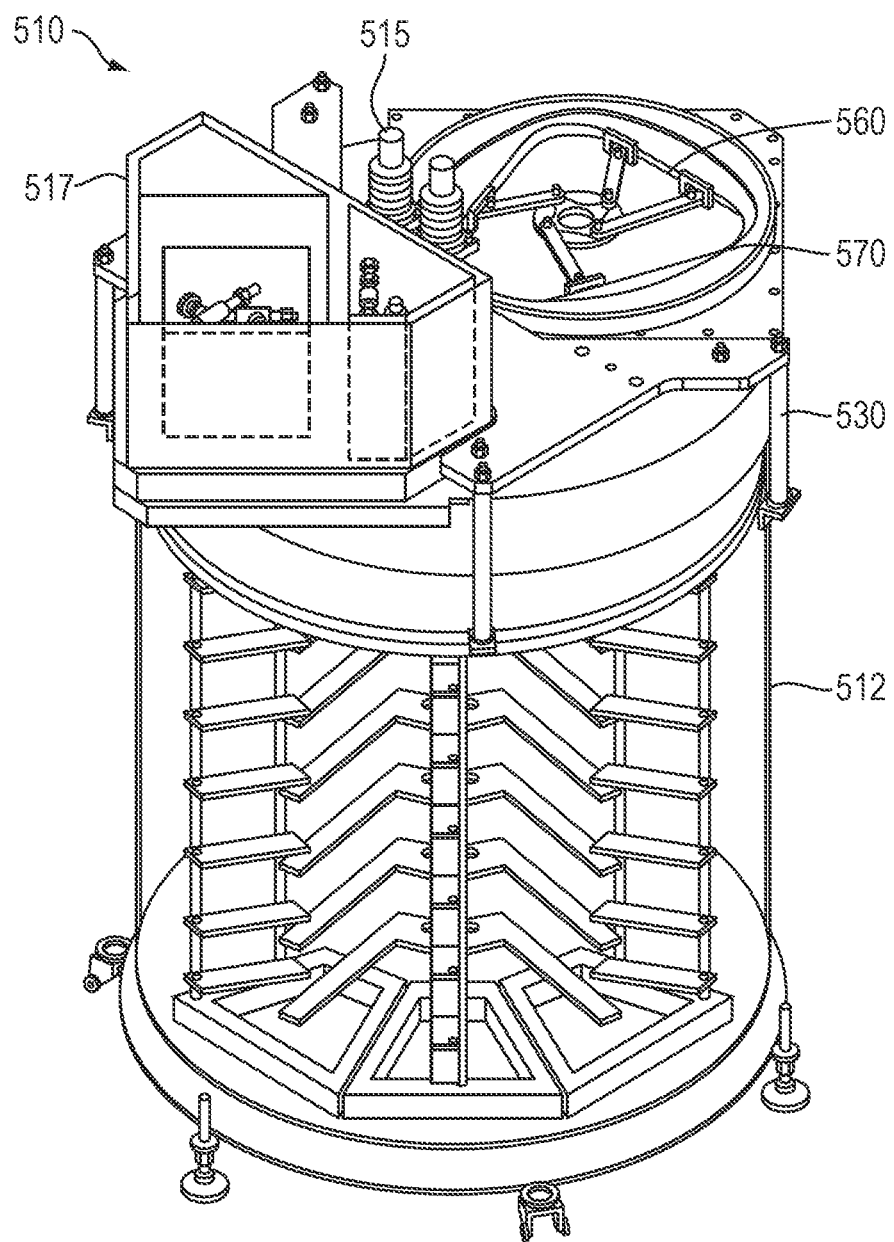
FIGS. 5A-B illustrate a cryogenic storage vault in one embodiment.
Figure 5B:
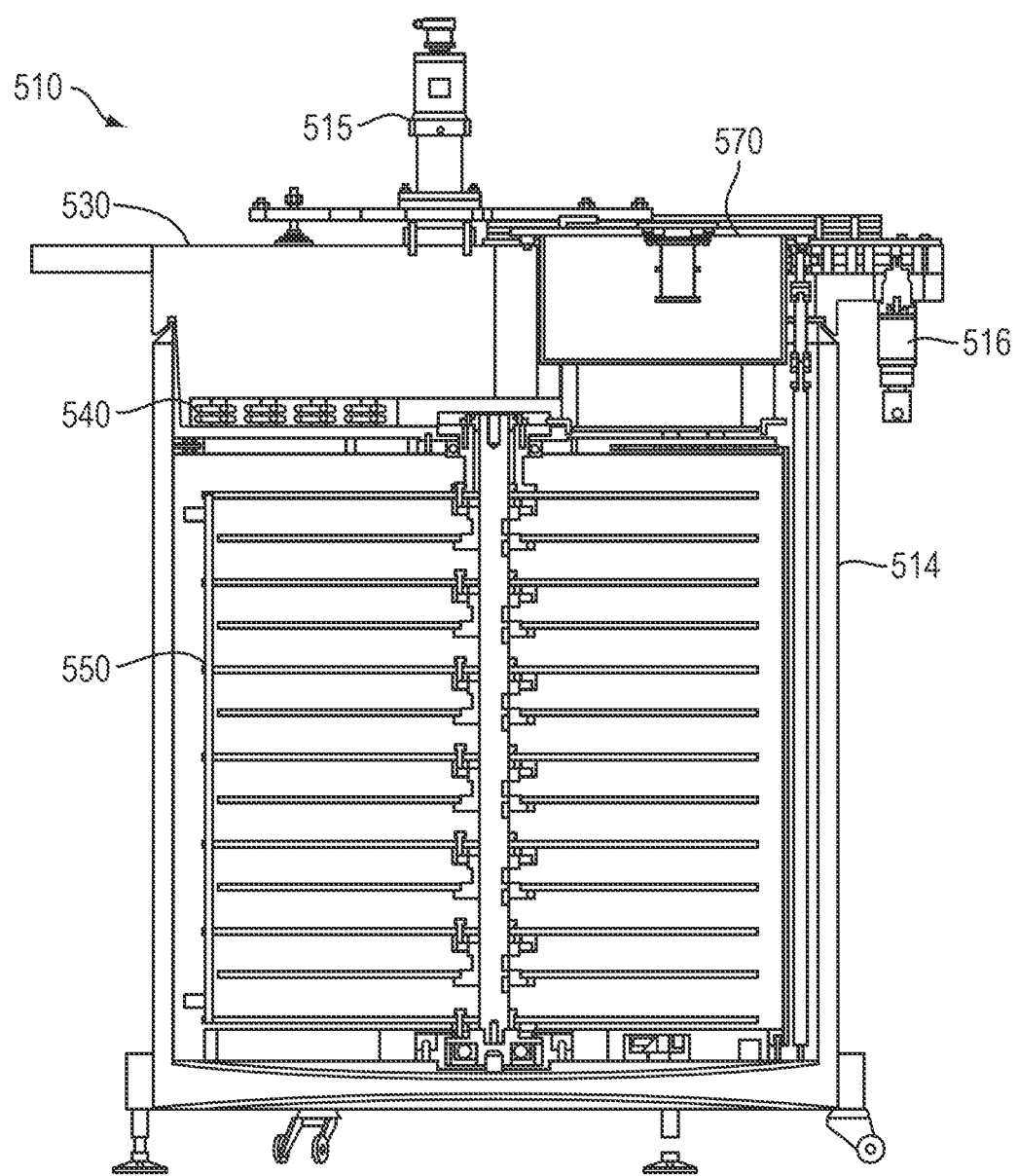

FIGS. 5A-B illustrate a cryogenic storage vault 510 in one embodiment. The storage vault 510 may be implemented in the systems 100, 300 described above with reference to FIGS. 1-3. FIG. 5A shows an external view of the storage vault 510, which includes a freezer 512, for example, a vacuum-insulated chamber such as a Dewar vessel, that is sealed at a top portion by a vault lid 530. At the top portion of the storage vault 510 resides a refrigerant port 517, which connects to a refrigerant supply (e.g., one or more nitrogen tanks, not shown) for channeling the entry of refrigerant to the storage vault 510. Motors 515, also located at the top portion and external to the storage vault 510, operate to actuate movement of samples 178 within the storage vault 510. Further, an opening 570 enables external access to samples 178 within the storage vault 510, and is sealed by vault cover 560 when samples 178 are not being added to or retrieved from the storage vault 510.

FIG. 5B shows cross-sectional internal view of the storage vault 510. Within the storage vault 510, a storage chamber 580 is surrounded by a freezer wall 514 and the vault lid 530, insulating the storage chamber 580 from external heat sources. Within the storage chamber 580 reside refrigeration coils 540 and storage rack 550. Further, located external to the storage vault 510 is an additional motor 516, which may be implemented to raise and lower trays 175 of samples 178 within the storage vault 510.

Components of the storage vault 510, as well as operations of the storage vault 510, are described below with reference to FIGS. 6-22.

Figure 6:
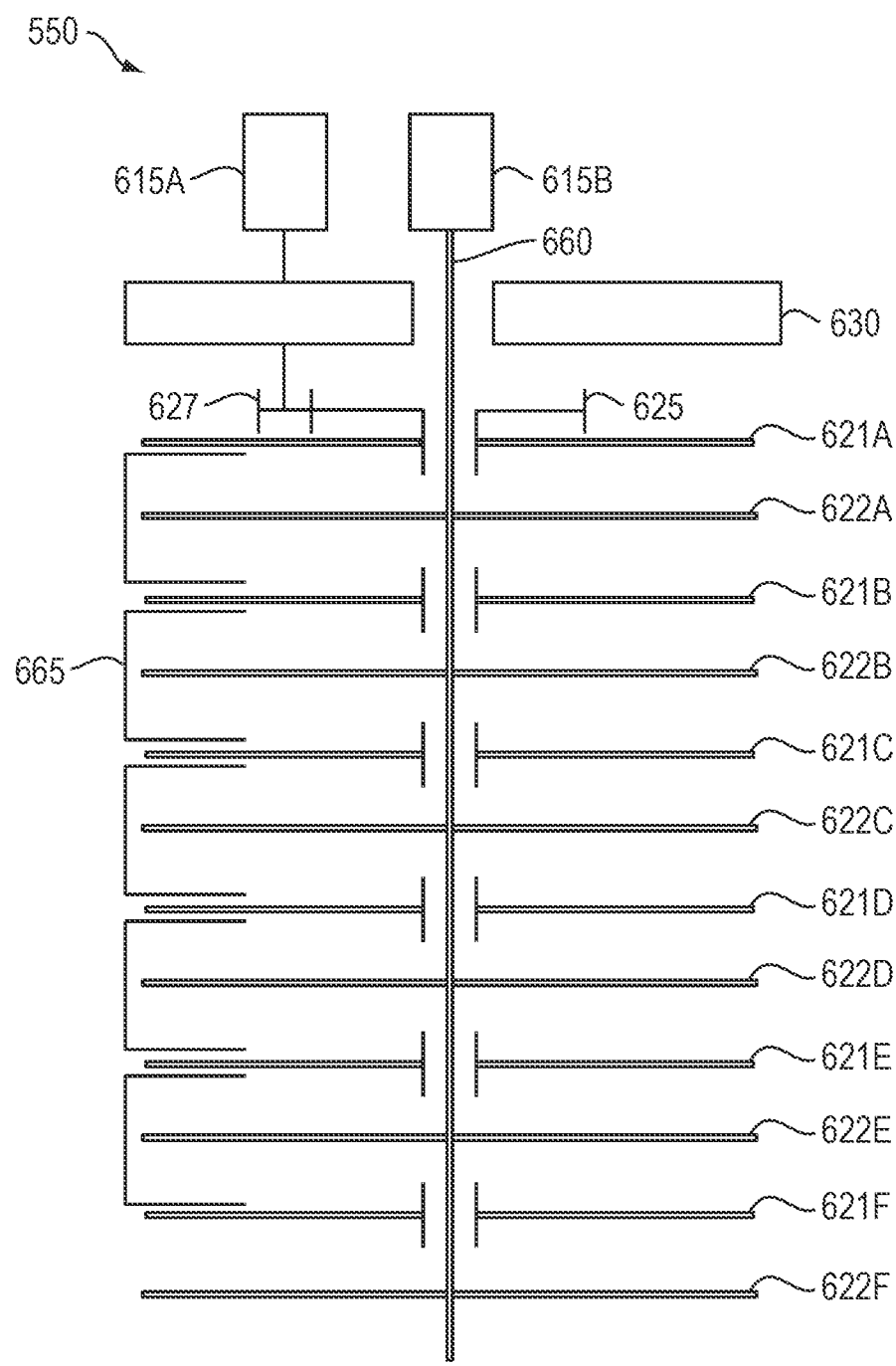
FIG. 6 is a block diagram of a storage rack adapted to support samples within a cryogenic storage vault.

FIG. 6 is a block diagram of a storage rack 550 that may be implemented in the storage vault 510 described above with reference to FIGS. 5A-B. The storage rack 550 is adapted to support a number of samples 178, and particularly a number of storage trays 175 each carrying a plurality of samples 178. The storage rack 550 includes a number of shelves, which are divided into two interleaved groups of shelves 621A-F, 622A-F. The first (or "odd") group of shelves 621A-F may be fixed to a common bracket 665 located at the outer perimeter of the shelves 621A-F. The odd group is also connected to a motor 615A (e.g., a servomotor) through a gear 625 and a pinion 627. As a result, the motor 615A can actuate the rotation of the shelves 621A-F simultaneously. Likewise, the second (or "even") group of shelves 622A-F may be fixed to a central axis 660, which is, in turn, connected to a motor 615B (e.g., a servomotor). As a result, the motor 615B can actuate the rotation of the shelves 622A-F simultaneously. As a result of the above configuration, two interleaved groups of shelves 621A-F, 622A-F can be rotated independently of one another. Both motors 615A-B may be located above the lid 630 of a storage vault 510, as shown for example in FIGS. 5A-B.

Figure 7A:
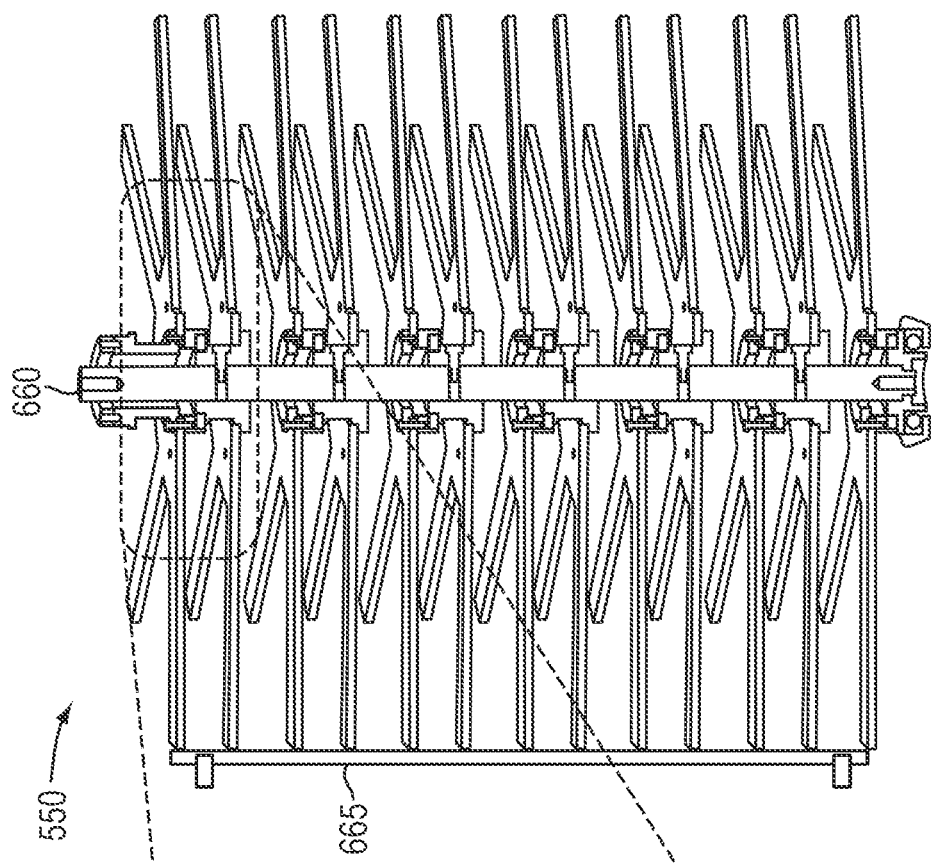
FIGS. 7A-B illustrate a storage rack in a further embodiment.
Figure 7B:
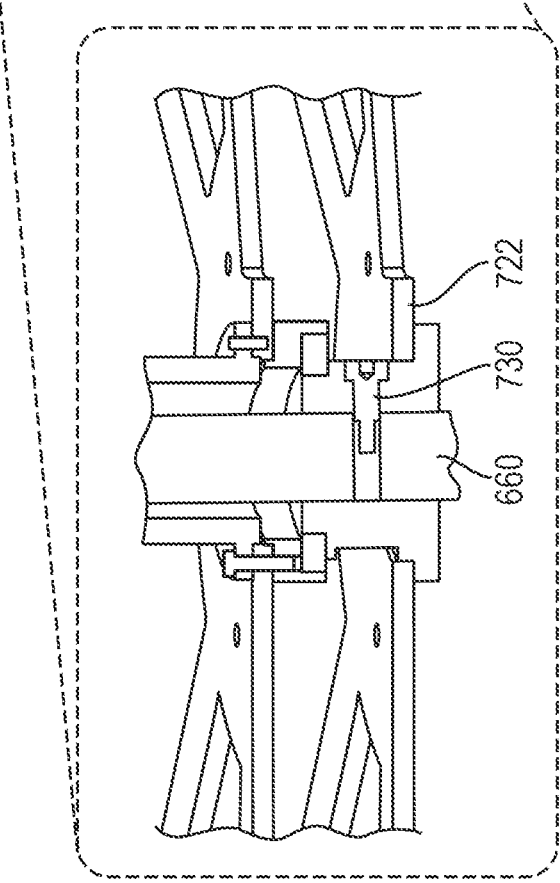

FIGS. 7A-B illustrate the storage rack 550 in further detail, with attention to the attachment of a shelf to a center axis 660. As shown in the inset of FIG. 7B, a single shelf 722 (comparable to the shelves 622A-F described above) may be fixed to the center axis 660 via a bolt 730.

Figure 8A:
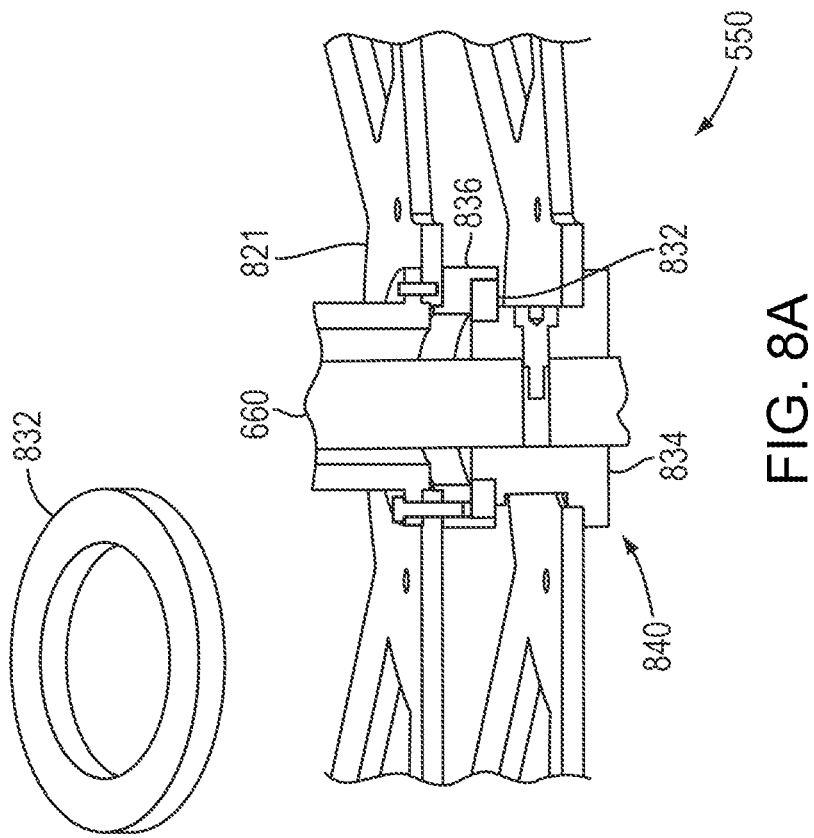
FIGS. 8A-B illustrate an axis portion of a storage rack.
Figure 8B:
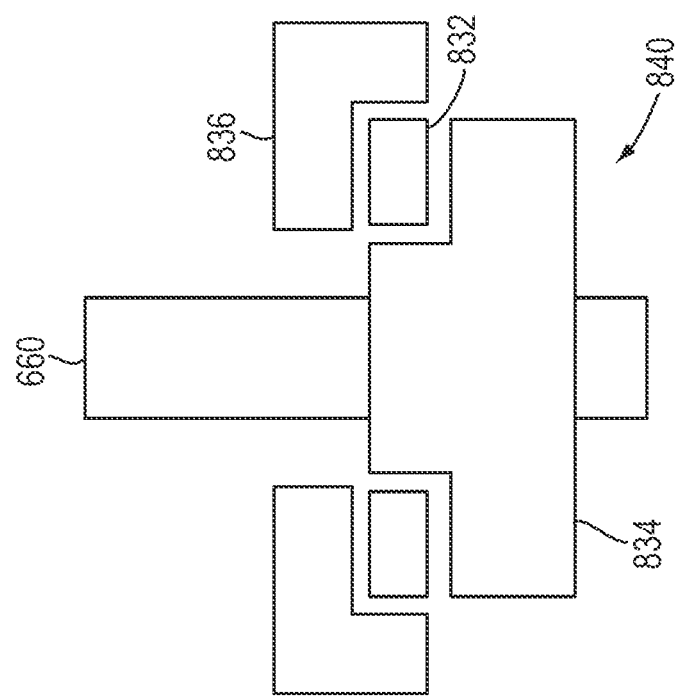

FIGS. 8A-B illustrate the storage rack 550 in further detail, with attention to the configuration of a shelf not attached to the center axis 660. FIG. 8A illustrates a shelf 821 (comparable to the shelves 621A-F described above), which is attached to a support 840 enabling the shelf 821 and bracket 821 to rotate around the center axis 660. FIG. 8B shows the support 840 in further detail. Here, a boss 834 is attached to the center axis 660 and may be adapted to a generally cylindrical shape with a portion extracted to accommodate a bearing 832. The bearing 832 may form a ring resting atop the boss 834, and may be machined of a low-friction material, such as a Polytetrafluoroethylene (PTFE) plastic (e.g., Rulon® J). A bell 836 may form a larger ring with a portion extracted to accommodate the bearing 832, and attaches to the shelf 821. As a result, the bearing 832 provides a low-friction running surface enabling the shelf 821, being fixed to the bell 836, to rotate atop the boss 834.

In one embodiment, the bearing 832 may be adapted to enable operation of the rack 550 (i.e., rotation of the shelf 821) at both cryogenic and ambient temperatures. For example, the bearing 832 may be formed of Rulon® J and have dimensions to align with the corresponding surfaces of the bell 836 and boss 834 in a temperature-dependent manner. In particular, the bearing 832 may expand in size at ambient temperatures, and contract in size at cryogenic temperatures. As a result, at ambient temperatures, the bearing 832 may be pressure-fixed to the bell 836, enabling a running surface on the boss 843. Conversely, at cryogenic temperatures, the bearing 832 may be pressure-fixed to the boss 834, enabling a running surface on the bell 836.

In order to assemble the support, the bearing 832 may be cooled to a cryogenic temperature, shrinking the bearing 832 sufficiently to be fit inside the bell 836. The bearing 832 may then be brought to ambient temperature, expanding the bearing 832 to secure it within the bell 836. At ambient temperature, the bell 836 and bearing 832 has sufficient clearance to fit atop the boss 834. Following this assembly, the support 840 may be brought to a cryogenic temperature within a storage vault 510.

Figure 9:
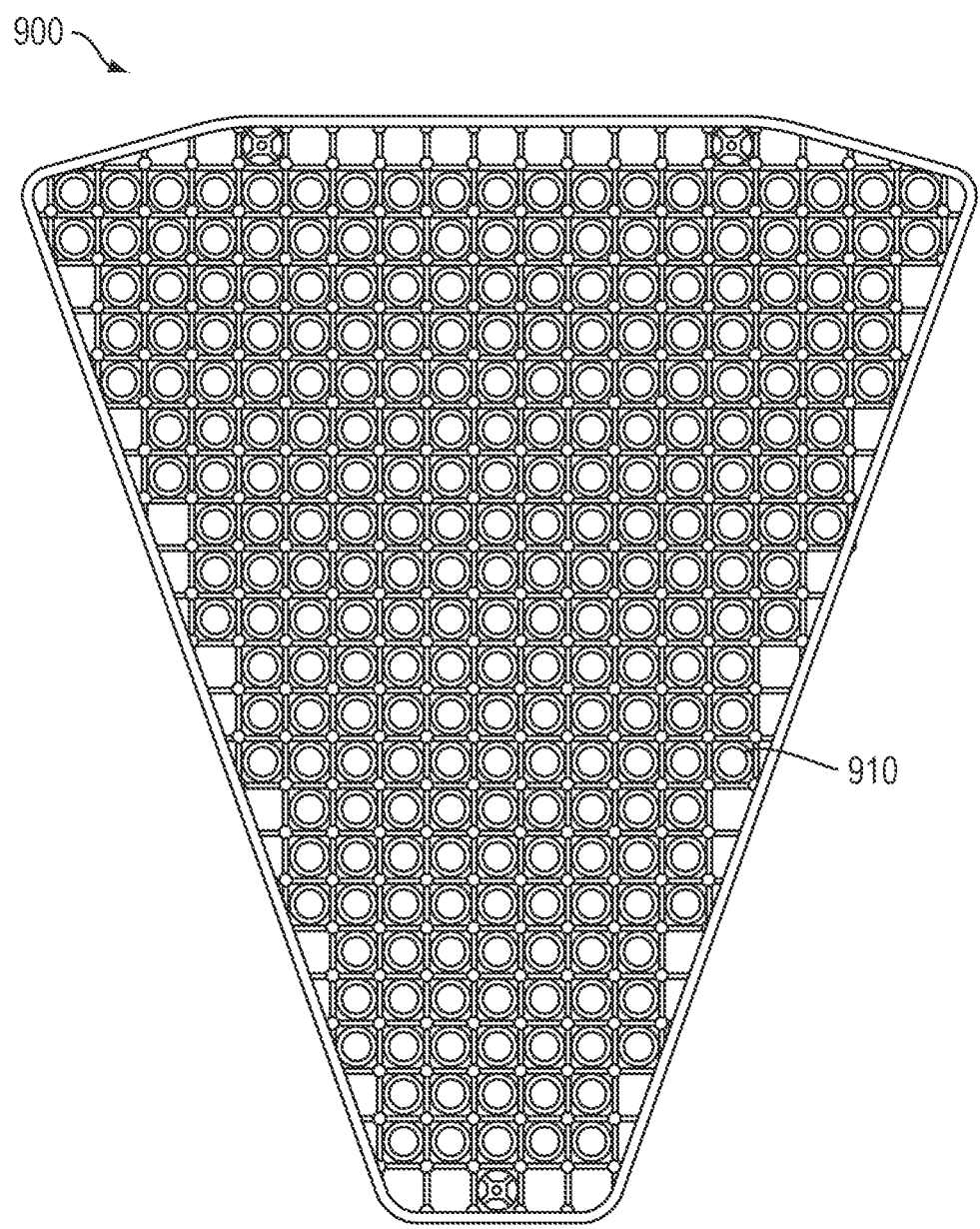
FIG. 9 illustrates a storage tray supporting samples within a storage rack.

FIG. 9 illustrates a storage tray 900 supporting samples within a storage rack (e.g., rack 550). In order to maximize storage density within a storage rack 550, the tray 900 may form a generally triangular or "pie-slice" shape, thereby maximizing usable storage space within a cylindrical storage vault 510. The storage tray 900 forms a number of slots 910 arranged into several rows and columns, each of the slots being adapted to hold an individual sample 178 (not shown). In the embodiment shown, the storage tray 900 is adapted to hold a maximum of 260 samples 178, where each sample 178 is a 2 ml-capacity vial. In alternative embodiments, the storage tray 900 may be adapted to accommodate a greater or fewer number of samples 178, and may include slots 910 adapted to receive samples 178 of larger or smaller dimensions (e.g., a 2 ml FluidX® tube 1160, or a 1.4 ml Matrix® tube 1150, see FIG. 11).

Figure 10:
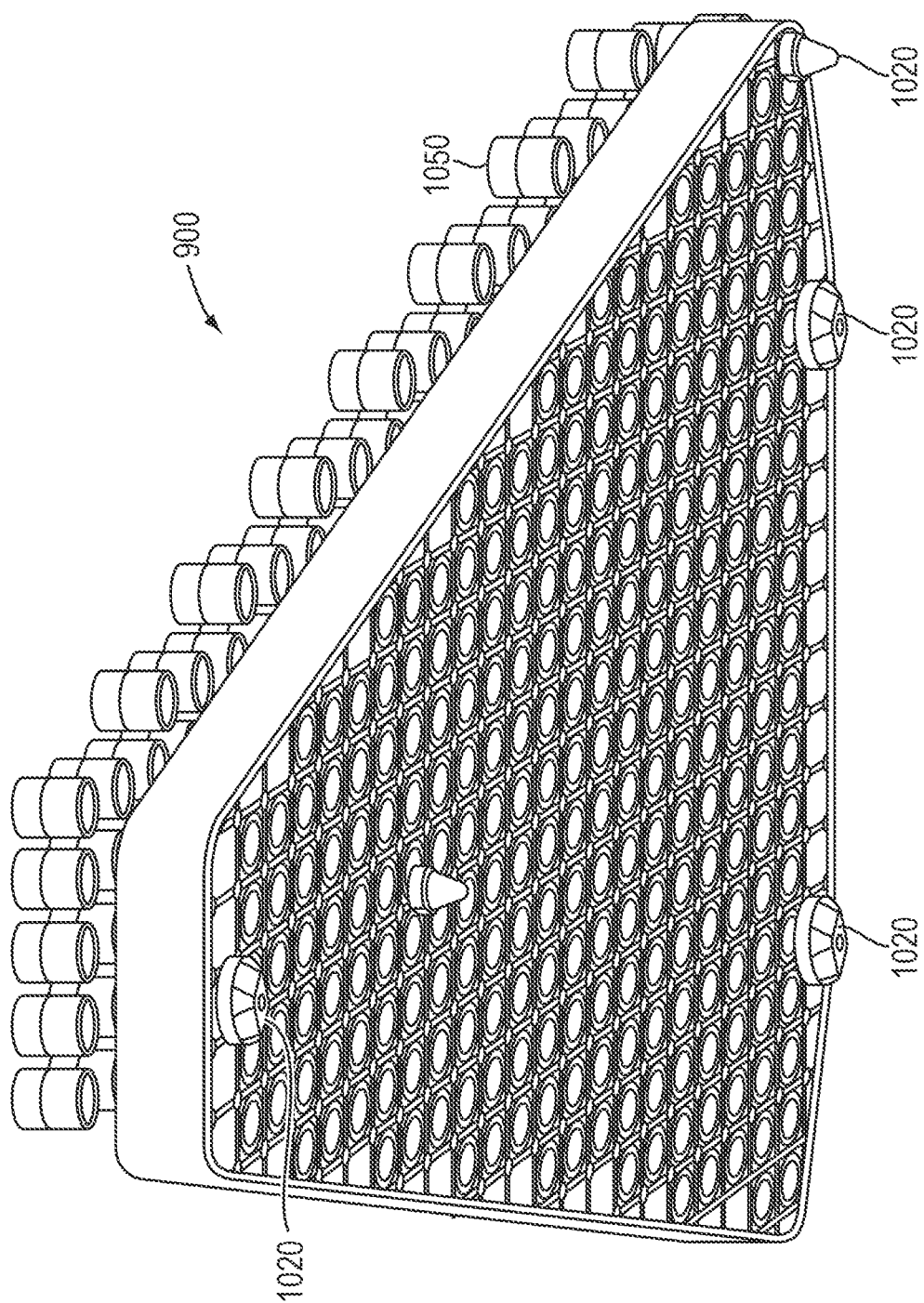
FIG. 10 illustrates a storage tray including kinematic pins.

FIG. 10 shows an underside view of the storage tray 900 holding a plurality of samples 1050. Here, the bottom surface of the tray 900 is shown to include a plurality of kinematic pins 1020. The kinematic pins 1020 may align with corresponding holes of a storage rack (e.g., rack 550), which enables precise positioning and lateral securement of the tray 900 on a storage rack 550. Further, the kinematic pins 1020 allow the tray 900 to be vertically lifted from the storage rack 550 without engaging a locking mechanism. A first subset of the kinematic pins 1020 may be adapted to secure the tray 900 to a storage rack 550, while a separate or overlapping second subset of the kinematic pins 1020 may be adapted to accommodate a vertical shuttle assembly 1300 (described below) for transferring the tray 900. In one example, the first subset of kinematic pins 1020 may be formed to minimize any movement of the tray 900 while stored on the storage rack 550, while the second subset of kinematic pins 1020 may be formed to allow for some movement in order to properly seat the tray 900 during a transfer.

Figure 11:
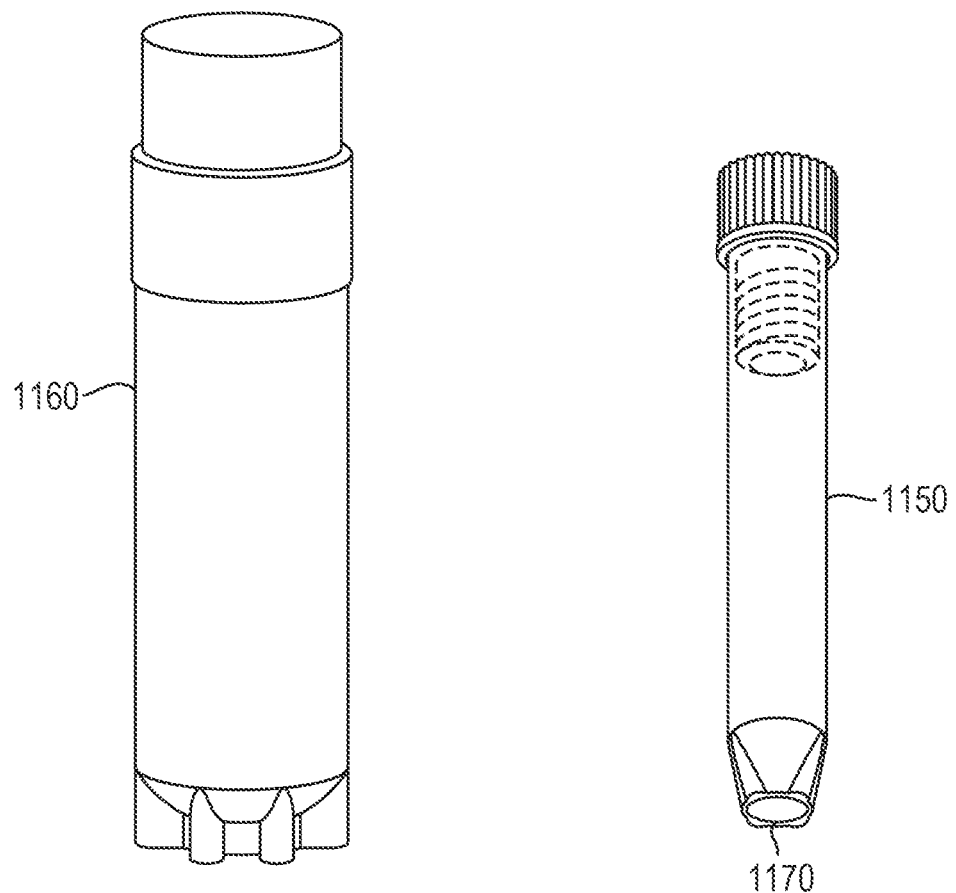
FIG. 11 illustrates an individual sample in one embodiment.

FIG. 11 illustrates two example individual samples 1150, 1160. The first sample 1150 is a 1.4 ml Matrix® sealed sample vial, which includes a barcode 1170 located at the bottom of the sample 1150. The barcode 1170 may include a unique code identifying the sample 1150, and may be read by a sensor component (e.g., camera, barcode reader, etc.) of a storage system (e.g., systems 100, 300) to verify the identity of the sample 1150 prior to or during a transfer of the sample 1150. The second sample 1160 is a 2 ml FluidX® sealed sample vial, which may also include a barcode at its bottom end (not shown) for identifying the sample 1160.

Figure 12:
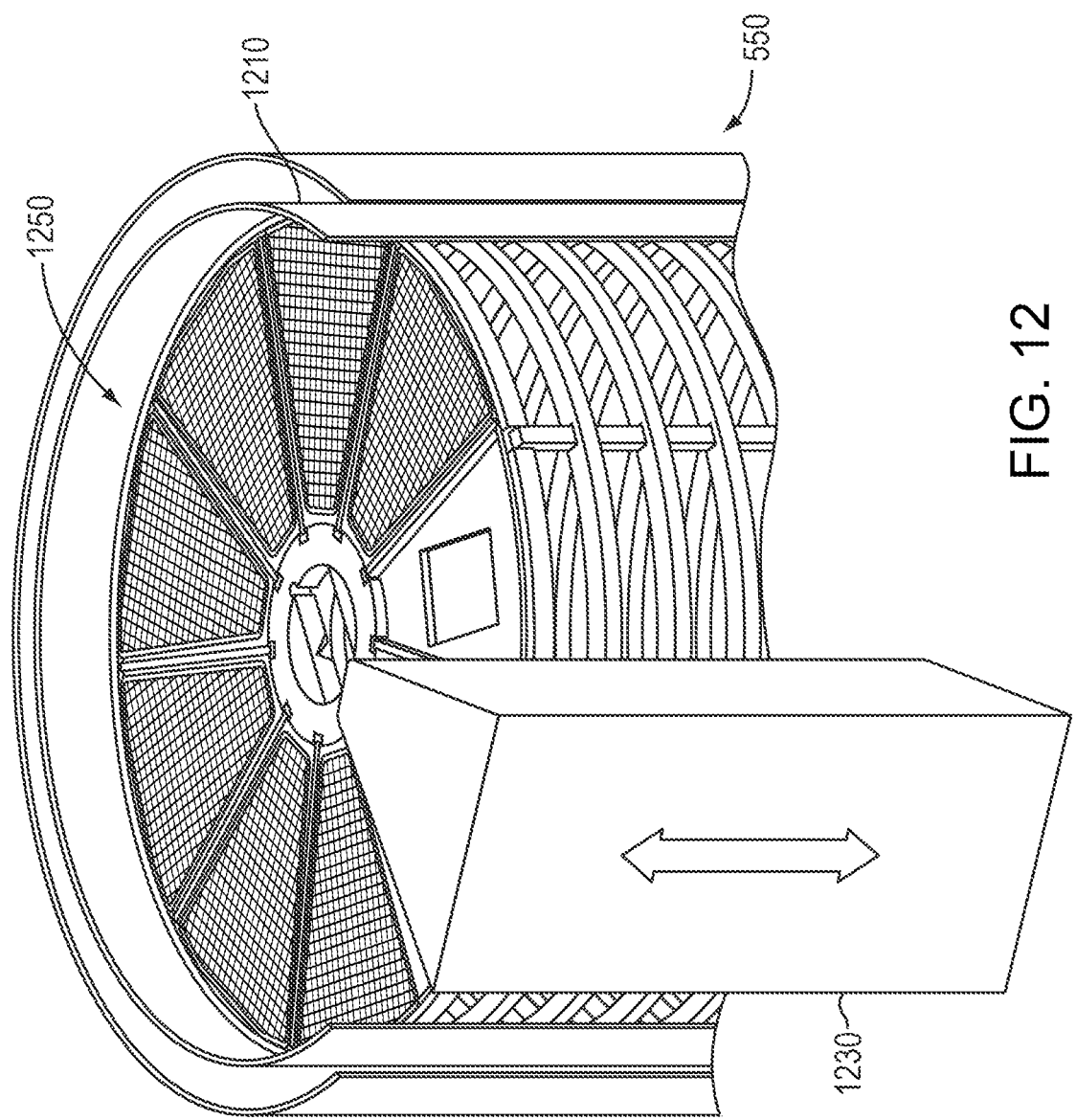
FIG. 12 illustrates an arrangement of storage trays on a shelf of a storage rack.

FIG. 12 illustrates an arrangement of storage trays 1250 (comprising, e.g., a number of storage trays 900) on a top shelf 1210 of a storage rack 550. The top shelf 1210, as well as lower shelves, may be divided into a number of sections (e.g., 8 sections), where each section can accommodate an individual storage tray 900. The arrangement 1250, as well as arrangements on the lower shelves, may also include a gap such that, when the rack 550 is configured in a certain state, the gaps form a vertical shaft 1230 through which an individual tray 900 can be moved to the top of the storage vault 110, 550 for presentation to a SHM 120. To perform such transfers, a vertical shuttle assembly 1300 may occupy a portion of the vertical shaft 1230. A vertical shuttle assembly 1300 in one embodiment is described below with reference to FIGS. 13-14.

Figure 13B:
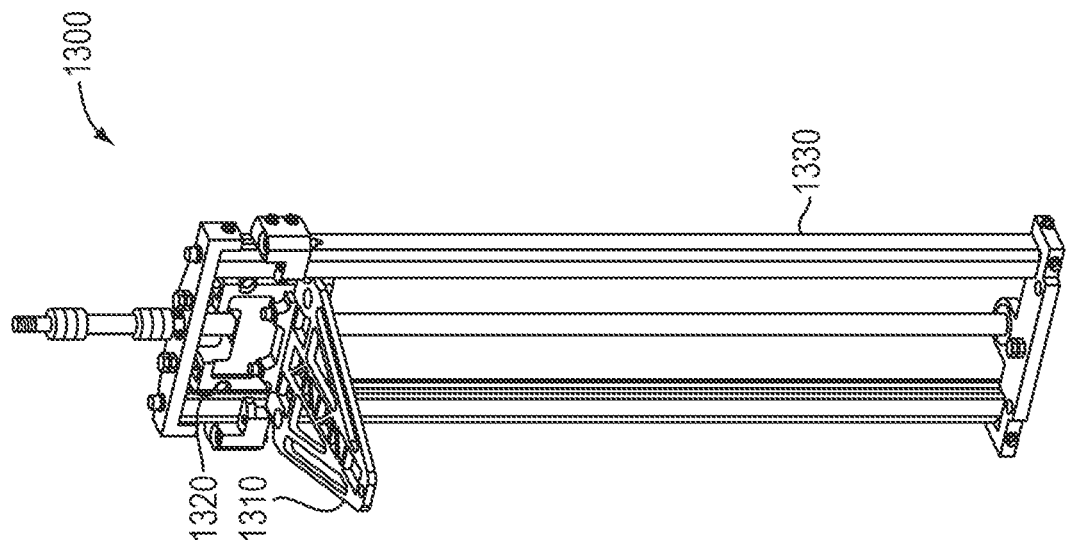
FIGS. 13A-B illustrate a vertical shuttle for transferring a storage tray within a storage vault in one embodiment.
Figure 13A:
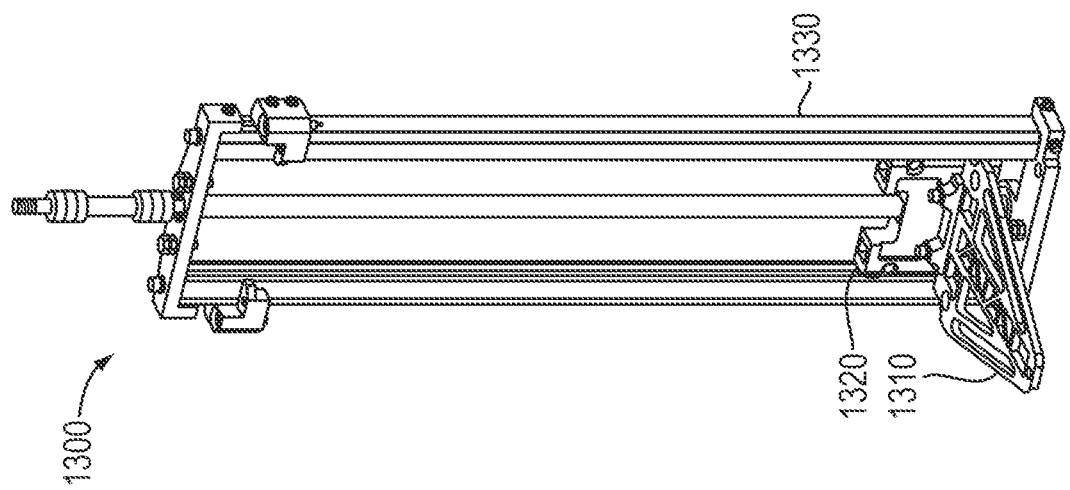

FIGS. 13A-B illustrate a vertical shuttle assembly 1300 for transferring a storage tray 900 within a storage vault 110, 510. The assembly 1300 includes rails 1330 that extend through a vertical dimension of a storage vault. A truck 1320 is adapted for securement between the rails 1330 and can be moved vertically through the length of the rails 1320. The truck 1320 further supports a platform 1310 fixed to it, the platform 1310 adapted to carry a storage tray (e.g., storage tray 900). The platform 1310 may be particularly formed to support a storage tray 900 in a stable position while avoiding contact with the portions of a storage rack 550 supporting the storage tray 900 during storage. FIG. 13A illustrates the assembly 1300 when the platform 1310 is lowered to the bottom extent of the rails 1330, while FIG. 13B illustrates the assembly 1300 when the platform 1310 is raised to the topmost extent of the rails 1330.

Figure 14A:
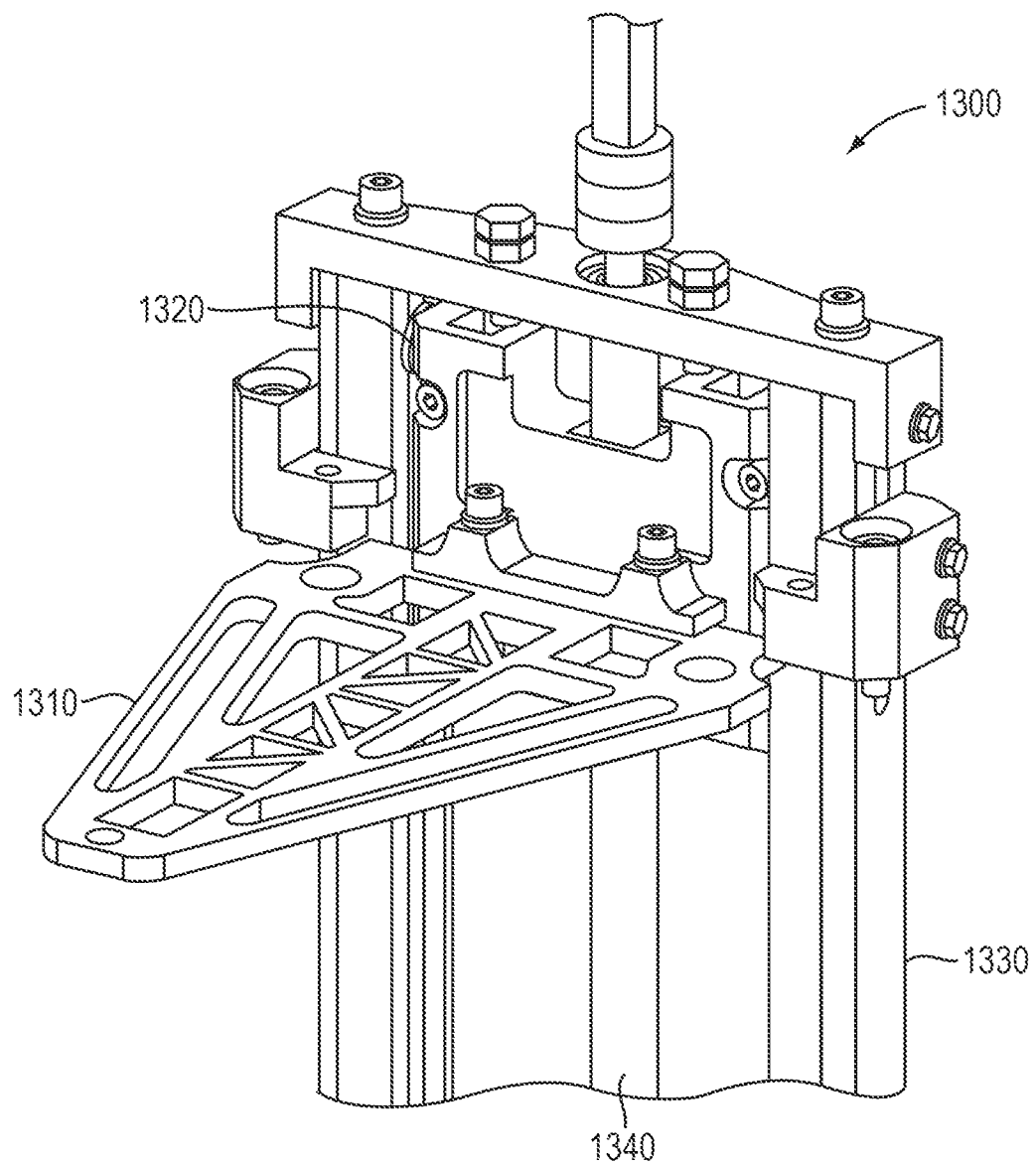
FIGS. 14A-B illustrate a vertical shuttle in further detail.
Figure 14B:
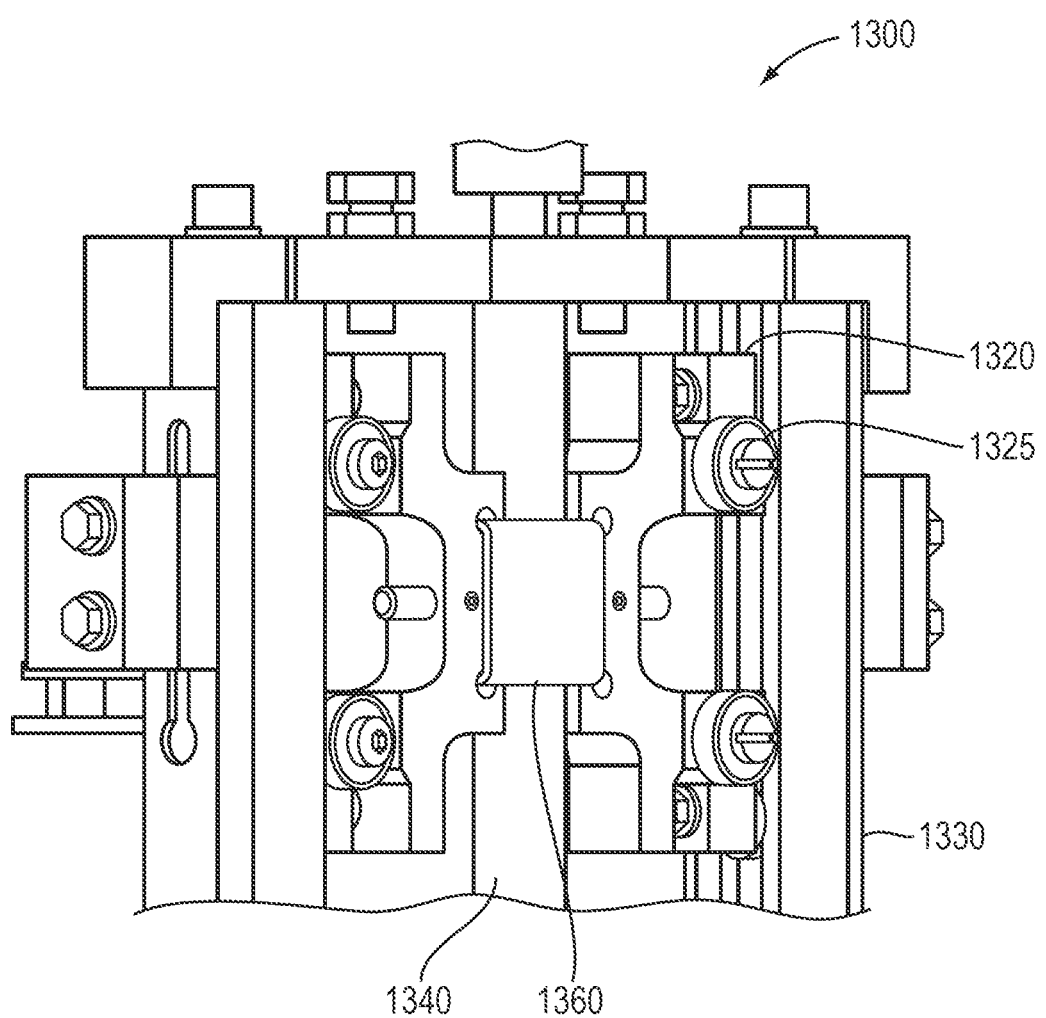

FIG. 14A-B illustrates the vertical shuttle assembly 1300 in further detail. FIG. 14A shows a front view of the vertical shuttle assembly 1300. In addition to the components described above, a leadscrew 1340 is positioned vertically between the rails 1330. FIG. 14B shows a back view of the vertical shuttle assembly 1300. The truck 1320 may connect to the leadscrew 1340 via a threaded attachment nut 1360 such that, when the leadscrew 1340 is rotated clockwise or counterclockwise, the truck 1320 is raised or lowered along the rails 1330. The truck 1320 may further include wheels 1325 contacting the rails 1330 for reducing friction during raising and lowering of the truck 1320. The leadscrew may be driven by a motor (e.g., a servomotor) such as the motor 516 described above with reference to FIG. 5B.

Figure 15:
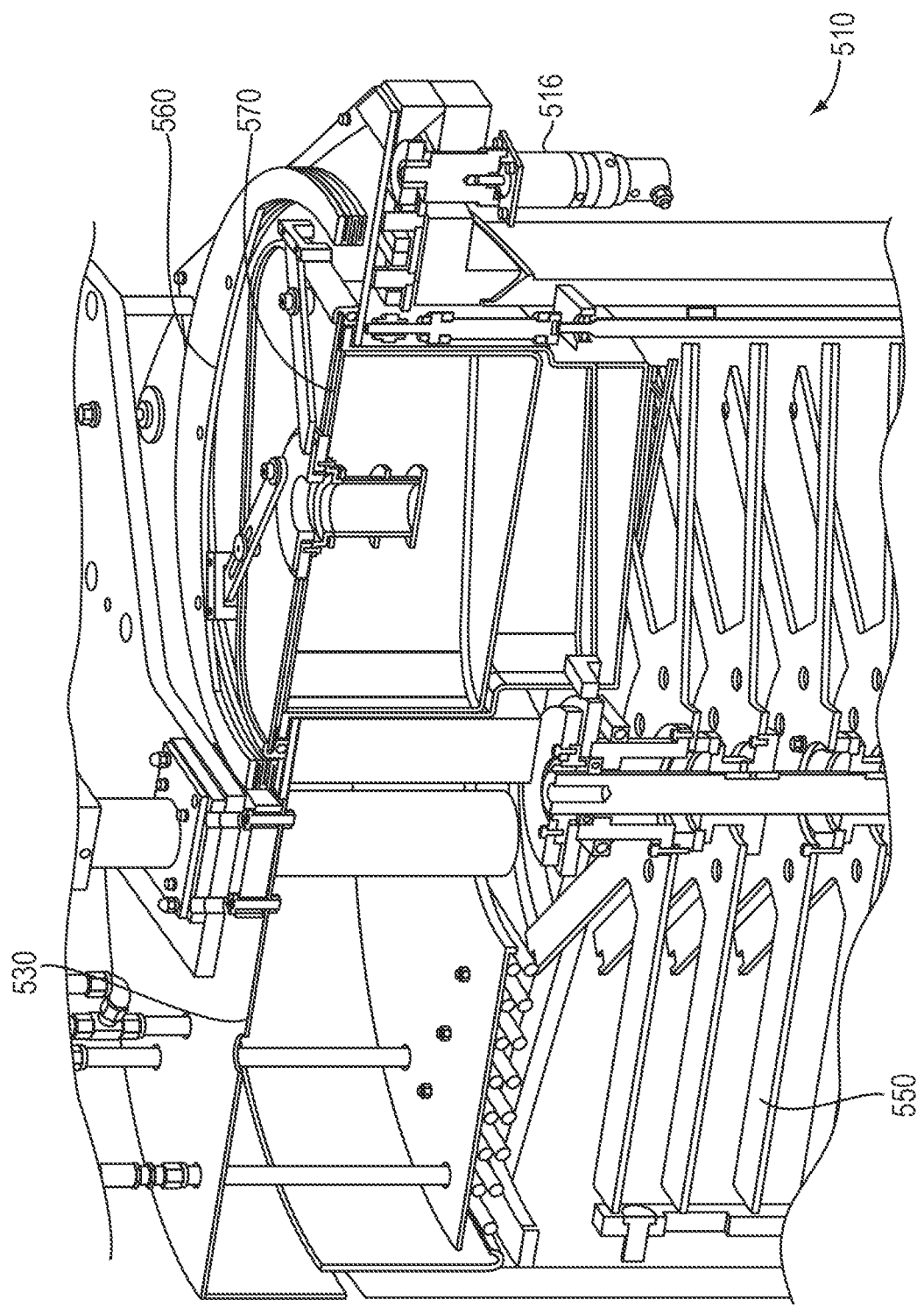
FIG. 15 illustrates a top portion of a storage vault.

FIG. 15 illustrates a top portion of a storage vault 510, including the lid 530, storage rack 550, motor 516, opening 570 and cover 560 as previously described above. Further, it can be seen that the opening 570 includes a chamber that extends between the top of the vault 510, through the entire depth of the lid 530, thereby enabling access to samples within the vault 510 from an external entity (e.g., a sample handling module). The cover 560 may include a portion that extends into some or all of this chamber when positioned to seal the opening 570 as shown.

Figure 16A:
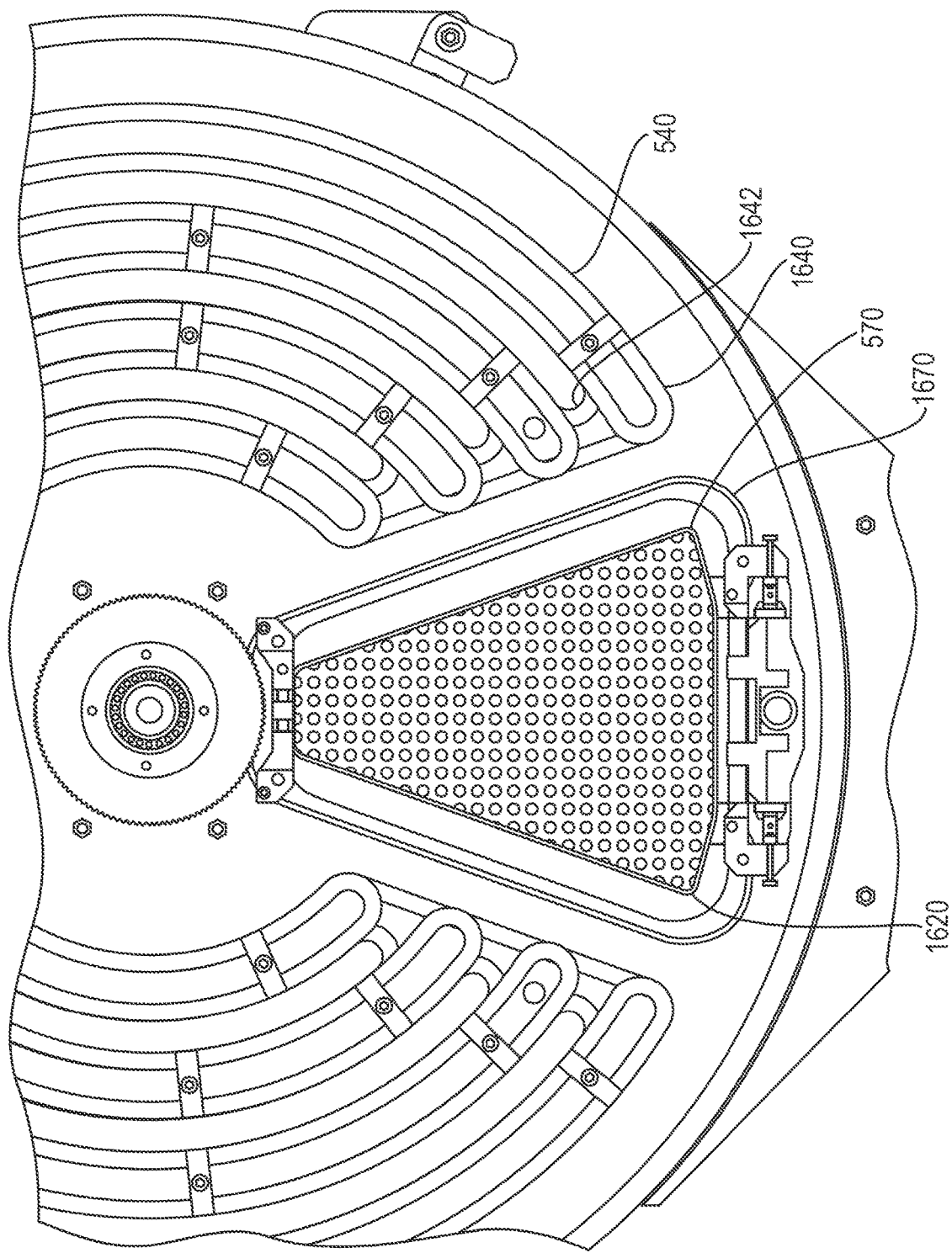
FIG. 16A illustrates a top-down view of a storage vault with lid removed, including docking of a storage tray for sample transfer.
Figure 16B:
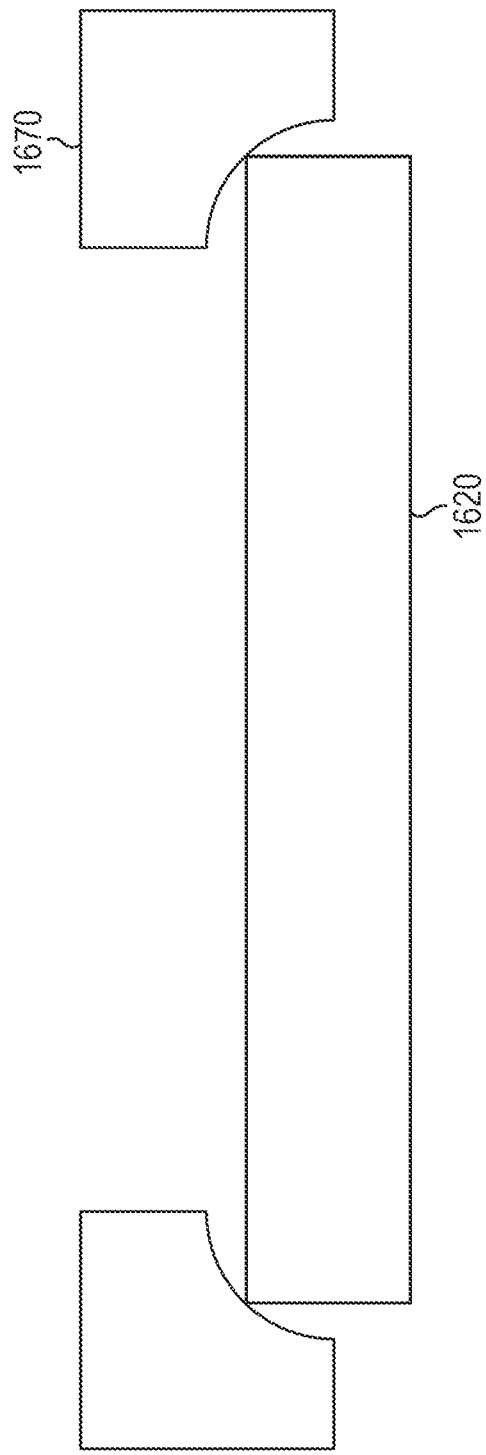
FIG. 16B is a side schematic illustration of the docked tray.

FIG. 16A illustrates a top-down view of an upper portion of a storage vault 510, including docking of a storage tray 1620 for sample transfer. Here, it can be seen that the opening 570 may form a top-down shape generally conforming to the top-down shape of the storage tray 1620. Further, the bottom of the opening 570 may include a threshold 1670 that is shaped similarly, thereby "framing" the tray 1620 when it is positioned at the bottom of the opening 570. This configuration is shown in a side view in FIG. 16B, where the upper corner of the storage tray 1620 is raised to contact the opening threshold 1670. In some embodiments, by positioning the storage tray 1620 against the threshold 1670, the leakage of heat and moisture into the cryogenic environment of the storage vault 510 can be reduced. Positioning the storage tray 1620 against the threshold 1670 may also prevent mishandled samples from falling into the storage vault during picking and placing samples from and into the sample slots. The storage tray 1620 and threshold 1670 need not form a seal across the opening 570, but may do so in an alternative embodiment.

Returning to FIG. 16A, the refrigerator coils 540 may extend in a circular pattern around the upper portion of the cryogenic environment except for a portion occupied by the opening 570. The coils 540 may include a primary coil 1640 and a secondary coil 1642, which may be positioned atop one another, as shown, or within a common plane. The primary and secondary coils 1640, 1642 may be connected to respective refrigerant conduits, and may be operated independently of one another. For example, under normal operation, the storage vault 510 may operate only the primary coil 1640 to maintain a cryogenic environment, the secondary coil 1642 serving as a backup coil in the event of a fault. Further, one or both coils 1640, 1642 may include one or more perforations or openings to enable a controlled quantity of refrigerant gas (e.g., nitrogen gas) to expel into the storage chamber, for example, to keep the storage chamber dry. In order to maintain samples in the storage tray 1620 within a cryogenic temperature (e.g., below the respective $T_G$), the coils 1640, 1642 may be positioned above the storage tray 1620 when the storage tray 1620 is fully elevated to the threshold 1670, thereby ensuring that the storage tray 1620 is continually exposed to convection cooling and refrigerant gas generated by the coils 1640, 1642. Operation of the refrigeration system is described in further detail below with reference to FIGS. 21-22.

Figure 17A:
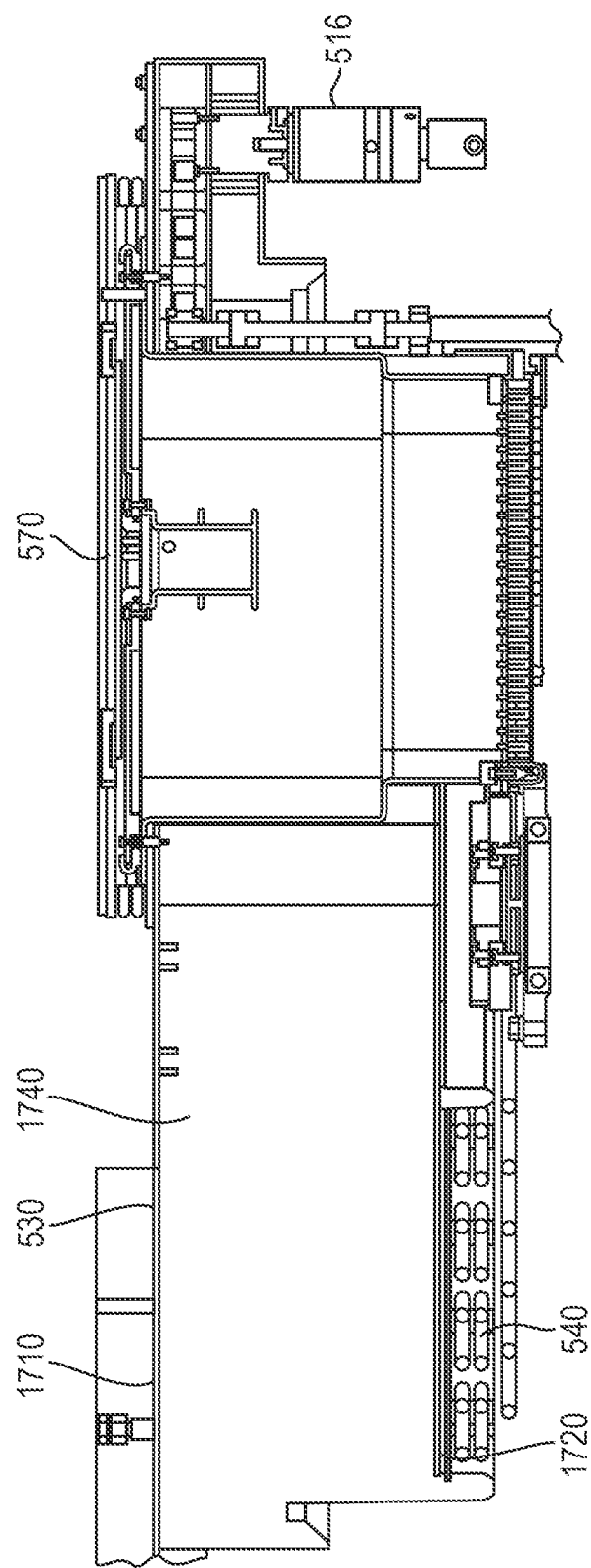
FIGS. 17A-C illustrate a lid portion of a storage vault in one embodiment.
Figure 17B:
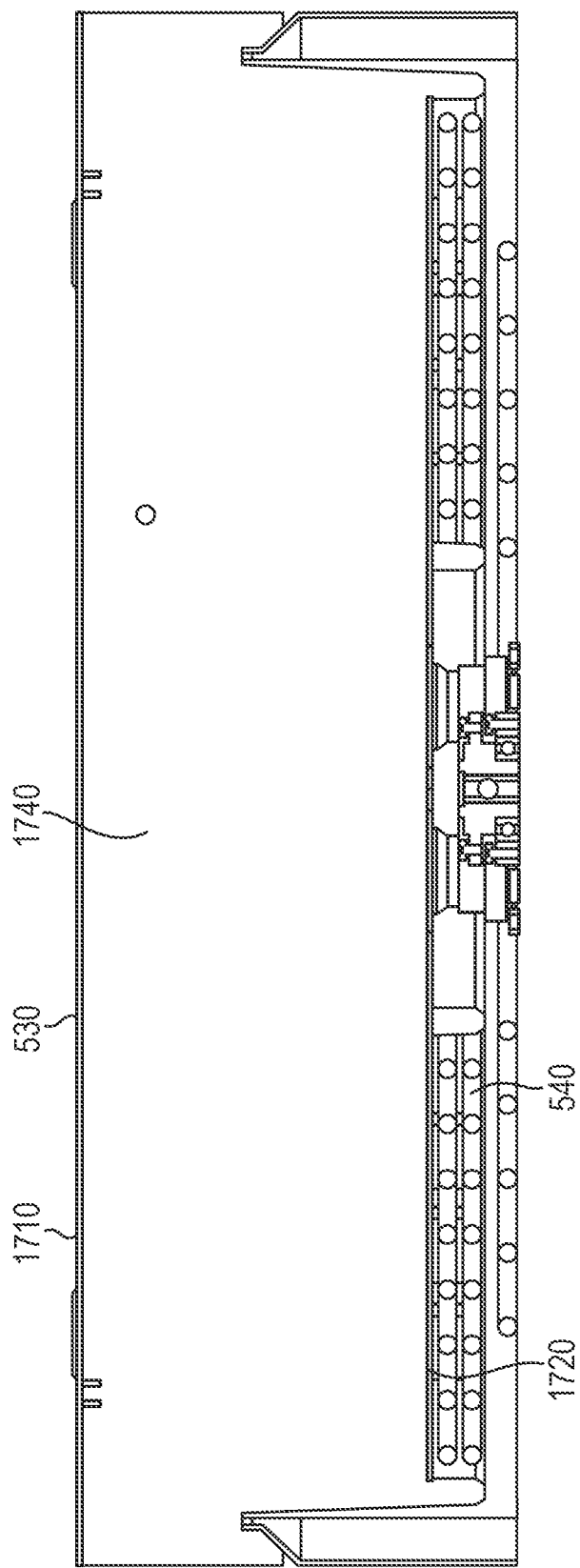
Figure 17C:
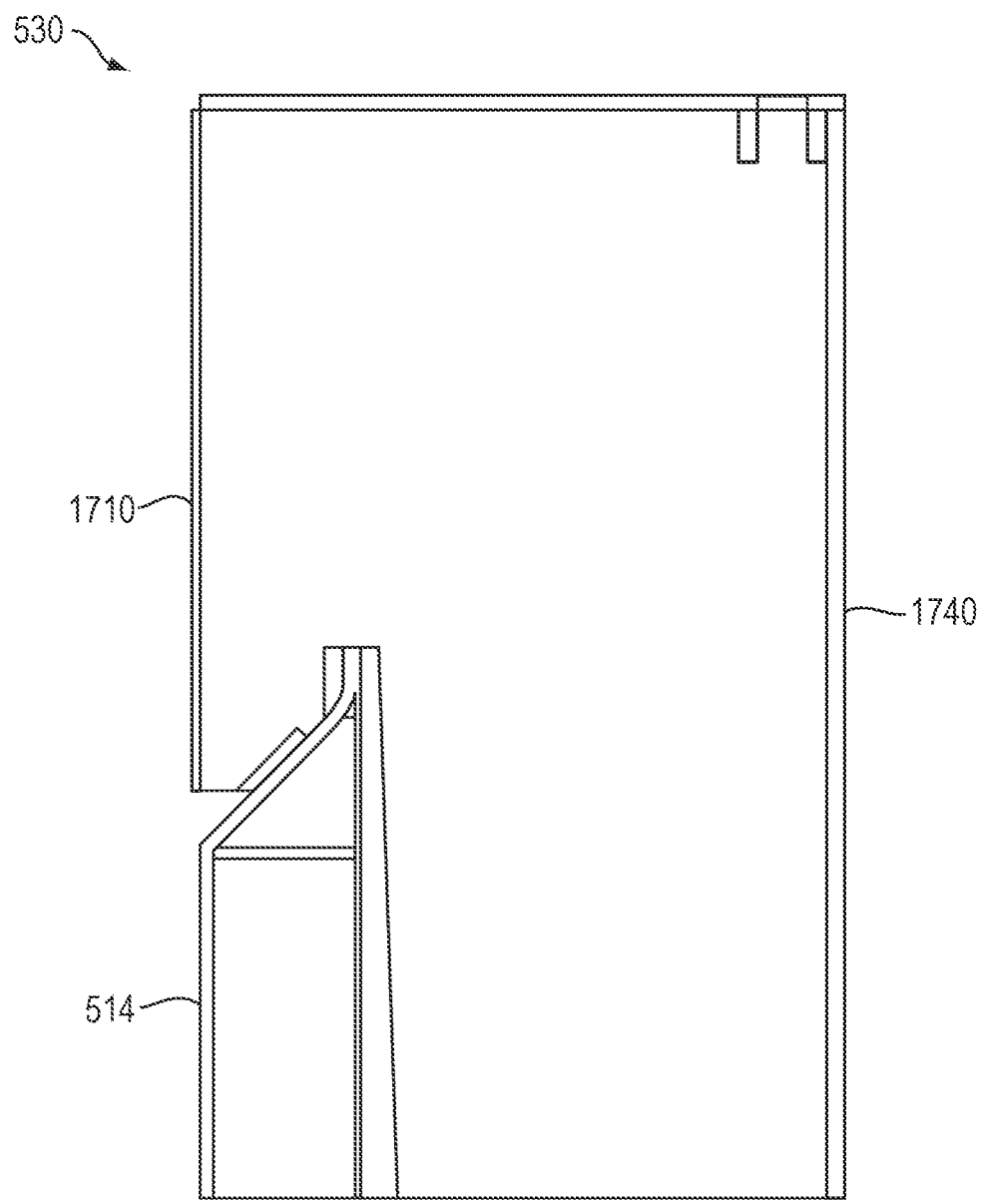

FIGS. 17A-C illustrate a lid 530 in further detail. FIG. 17A depicts a side view of a top portion of a storage vault 510, including the lid 530, opening 570 and refrigeration coils 540 as described above. FIG. 17B depicts a similar side view, but is rotated to a cutaway of the lid 530 through a portion not occupied by the opening 570.

FIG. 17C depicts a top and side portion of the lid 530 in further detail. An upper skin 1710 may comprise a metal (e.g., stainless steel) layer covering the top and sides of the lid 530, thereby preventing long-term diffusion of moisture through the lid 530. The lid 530 may be seated onto the freezer wall 514, and the union between the lid 530 and freezer wall 513 may be sealed by silicone sealant and/or a band of cryotape. A lower plate 1720 of the lid 530 may be composed of stainless steel or other metal. In alternative embodiments, the lower plate 1720 may be composed of a glass-reinforced plastic (GRP) moulding. The lower plate 1720 may occupy an inner wall of the lid 530 contacting the freezer wall, and/or may comprise the bottom surface of the lid 530 (as shown) as well as a wall forming the boundary of the opening 570. Alternatively, the wall forming the boundary of the opening may be composed of a GRP moulding. The lower plate 1720 may also serve as a structural support to the refrigeration coils 540, which may be fixed to the bottom surface of the lower plate 1720. The lid core 1740 may comprise a polyurethane foam.

Figure 18:
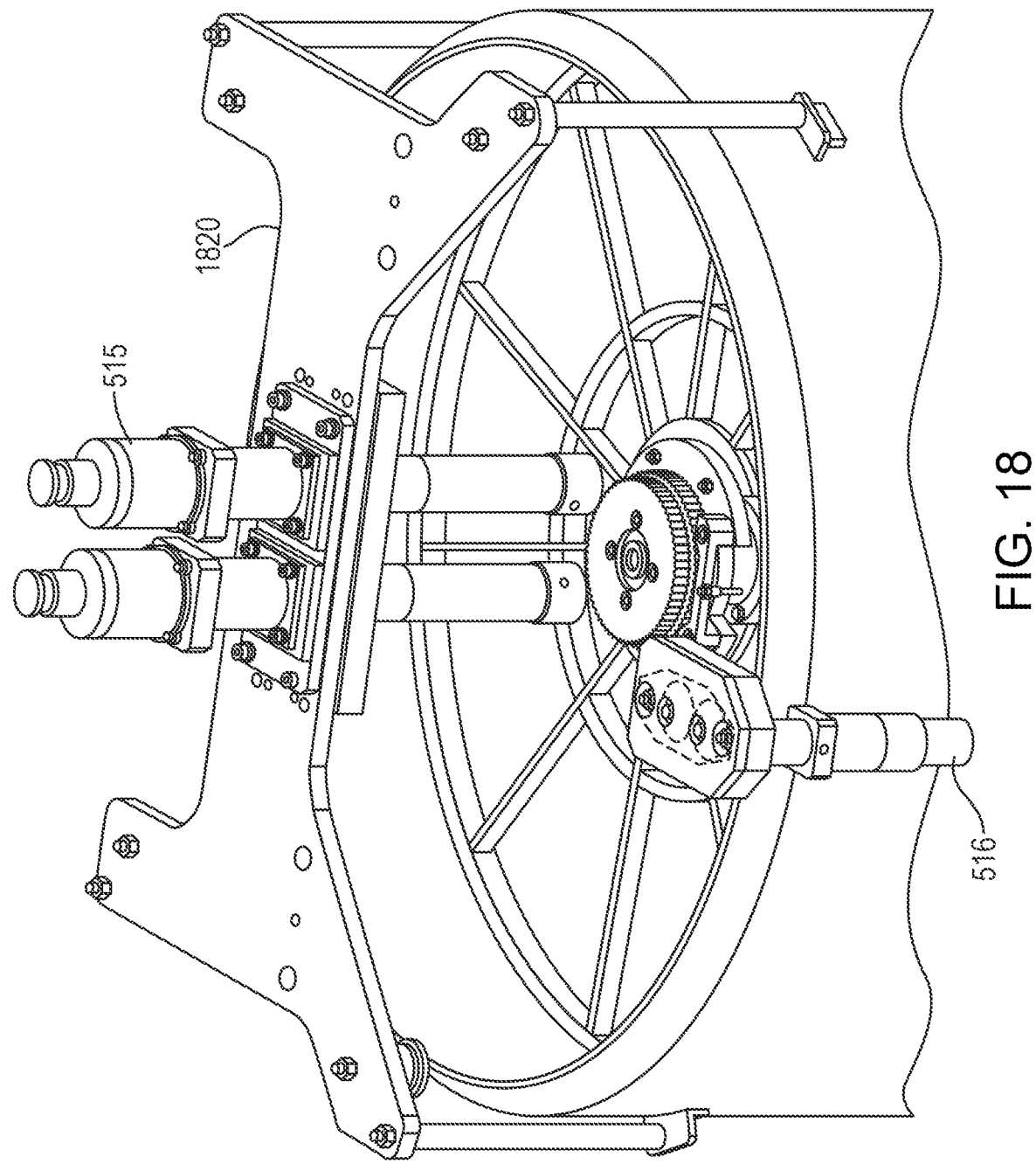
FIG. 18 illustrates a top external portion of a storage vault, including motors with lid removed, in one embodiment.

FIG. 18 illustrates a top external portion of a storage vault 510, including motors 515, 516 as previously described above. The motors 515 may be located external to the cryogenic environment within the storage vault 510 in order to isolate the temperature-sensitive components of the motors 515, 516 from the cryogenic environment, as well as to allow repair and replacement of the motors 515, 516 without disrupting the cryogenic environment. A bracket 1820, extending above and across the vault 510, supports the motors 515, 516 in the aforementioned position.

Figure 19:
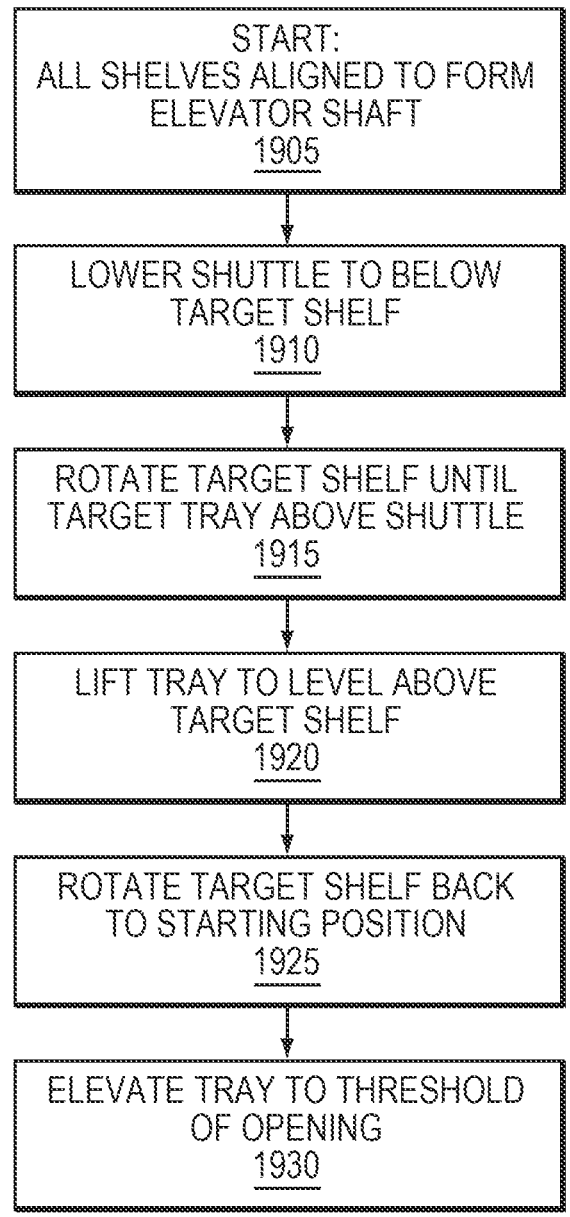
FIG. 19 is a flow diagram of a process of retrieving a sample from a storage vault in one embodiment.

FIG. 19 is a flow diagram of a process 1900 of retrieving a sample from a storage vault (e.g., storage vault 510). The process 1900 is described in further detail below with reference to FIGS. 20A-M.

FIGS. 20A-M are schematic illustrations of the process of retrieving a sample as shown in FIG. 19. Each of the block diagrams of FIGS. 20A-M depict a simplified schematic of a storage vault 2000 at right, which may be comparable to the storage vaults described above with reference to FIGS. 1-18. The storage vault 2000 includes several stacked shelves, numbered 1-6, each shelf supporting a respective storage tray 175 holding plural samples 178. The storage vault 2000 further includes a vertical shuttle assembly 1300 at right. To the left of the vault 2000 is shown a top-down view of each shelf 1-3, as well as the vertical position of the vertical shuttle assembly 1300 relative to the shelves. The process 1900 described below is an example process for retrieving a tray 175 from shelf 3 and presenting the tray 175 to a SHM 120 (not shown) for the transfer of samples 178 to and/or from the tray 175.

Figure 20A:
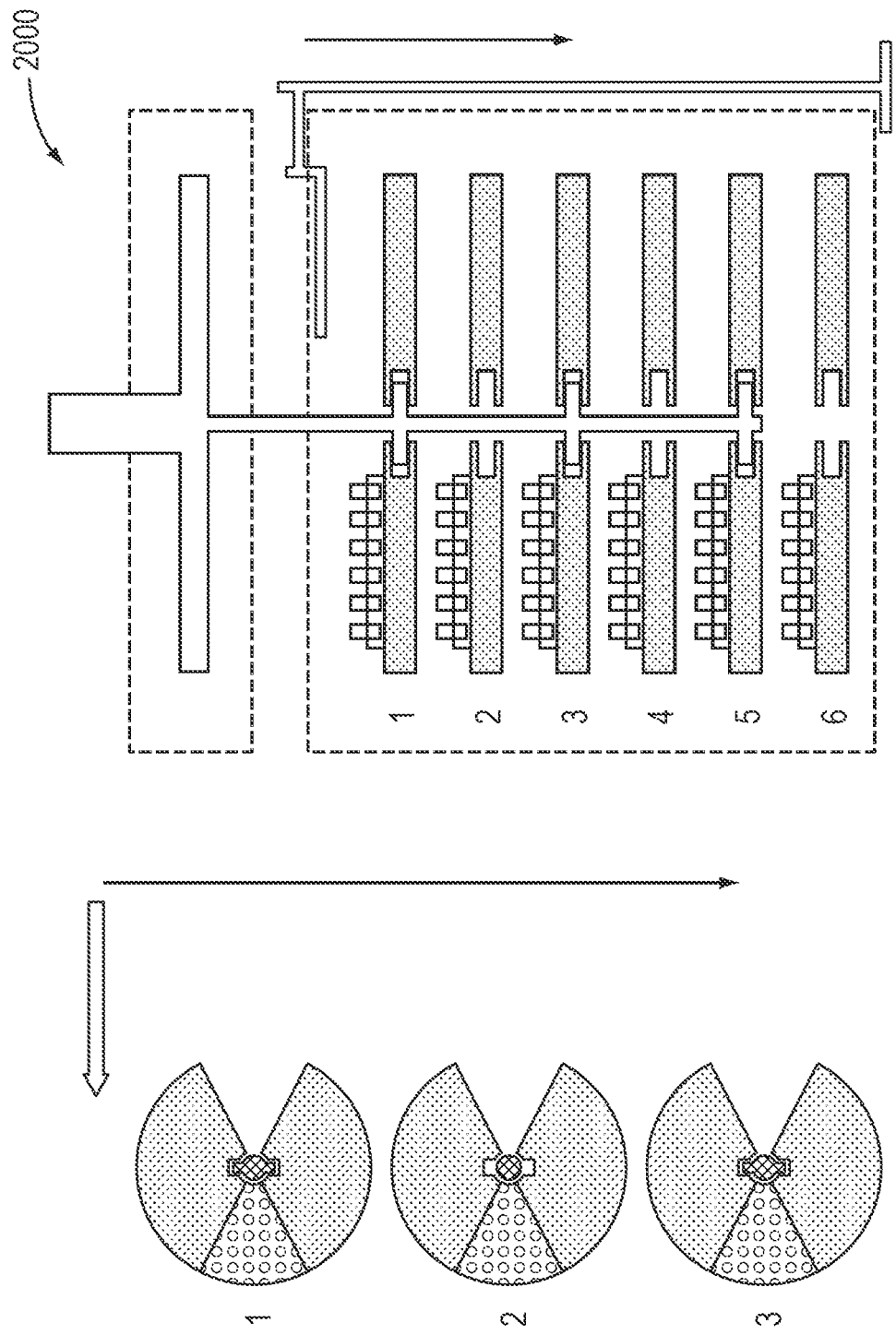
Figure 20B:
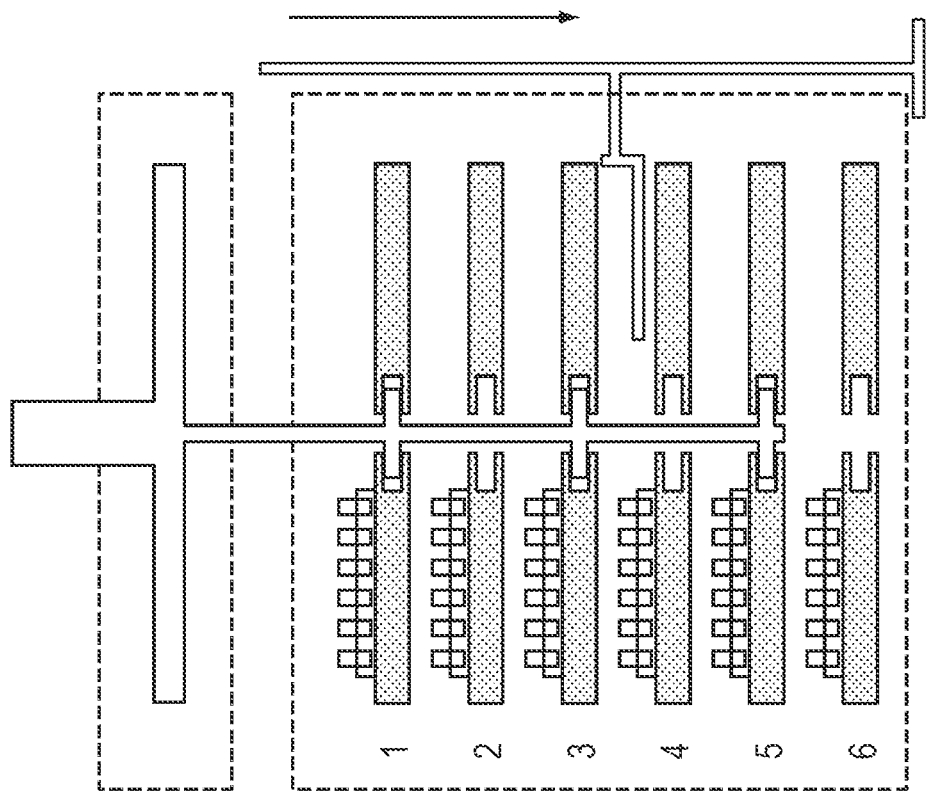
Figure 20B:
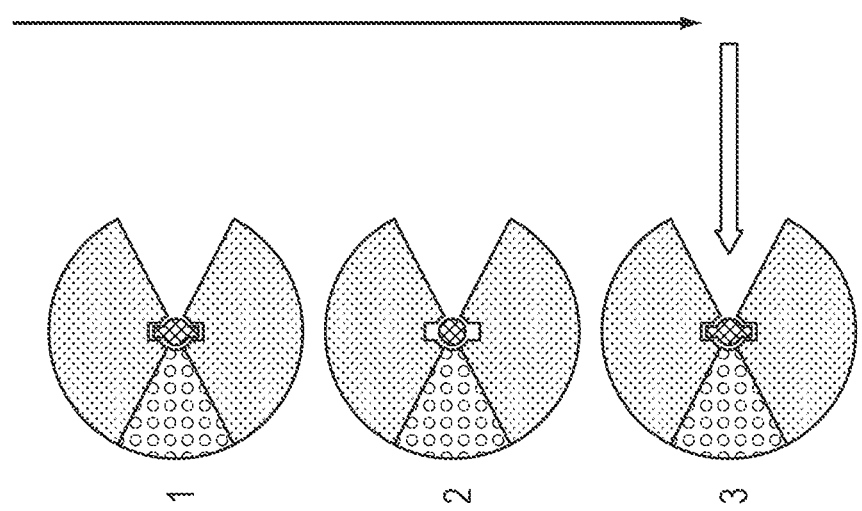
Figure 20C:
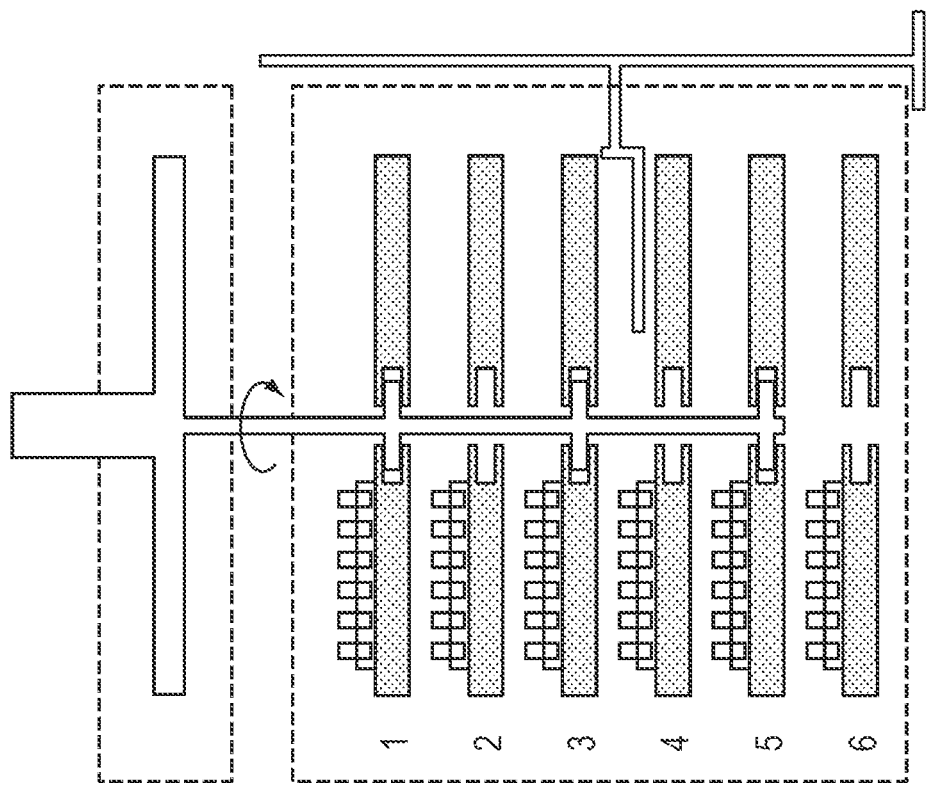
Figure 20C:
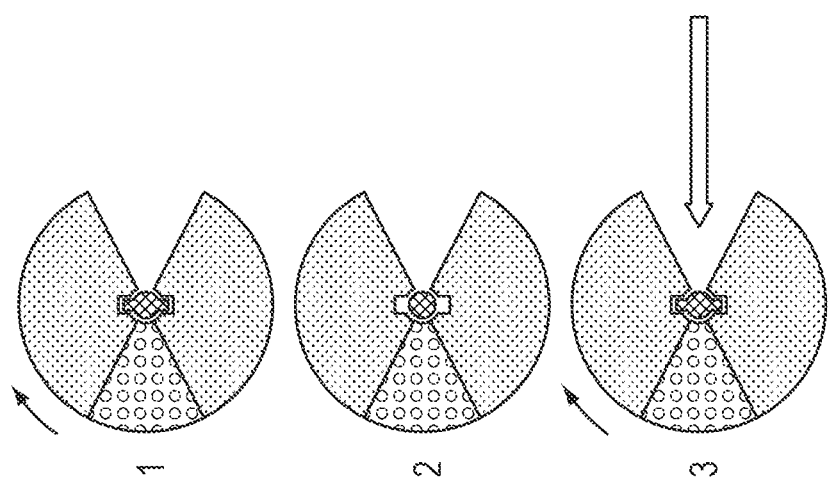
Figure 20D:
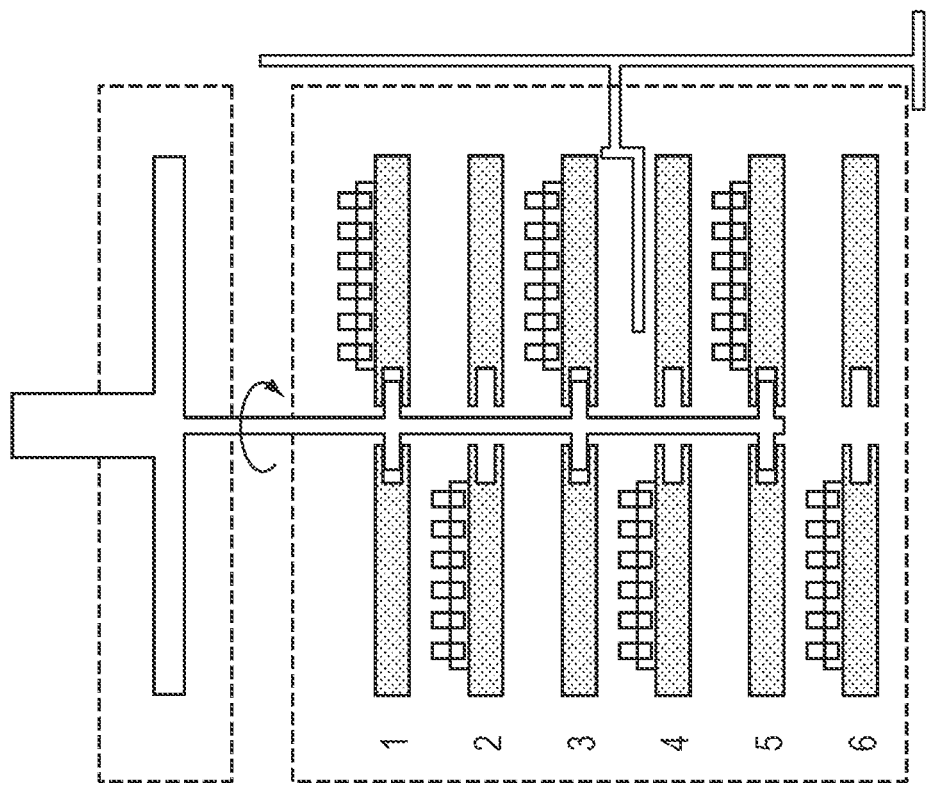
Figure 20D:
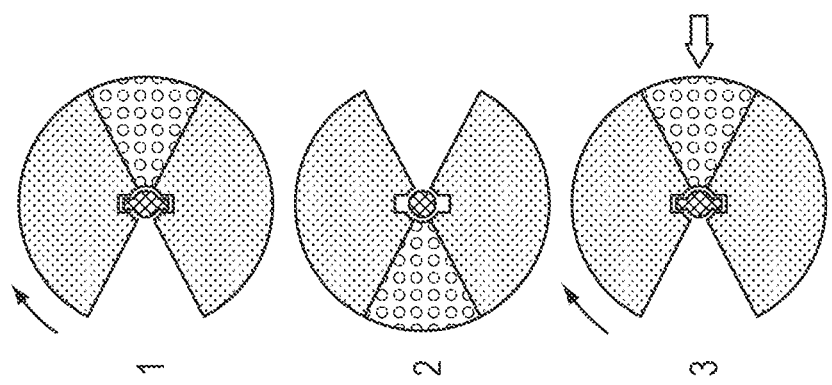
Figure 20E:
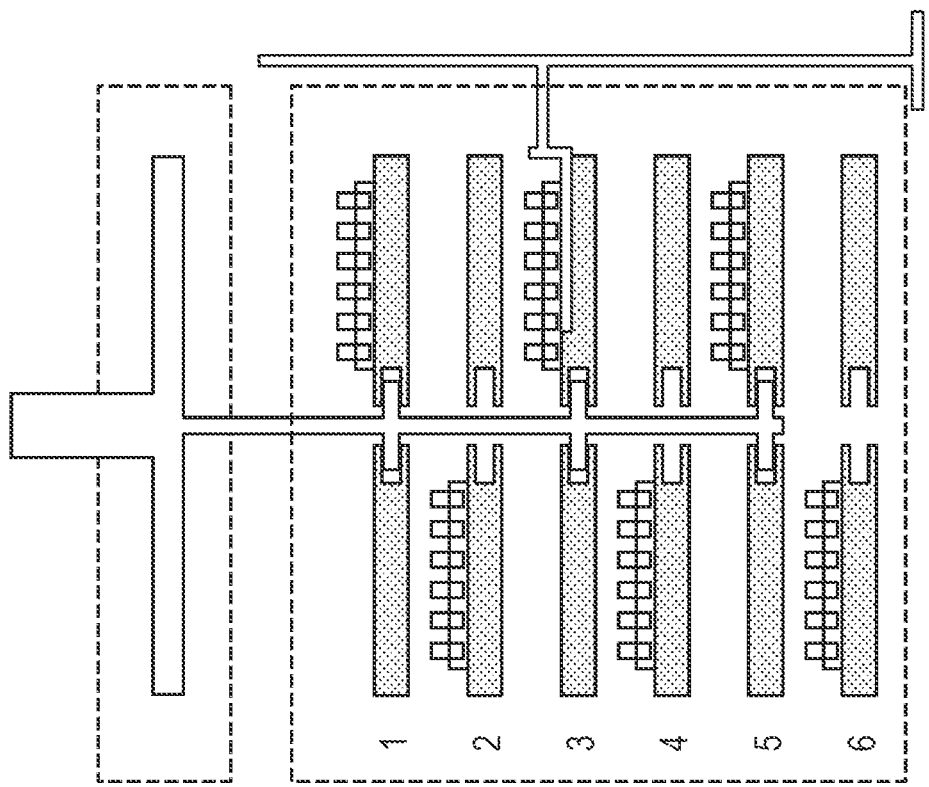
Figure 20E:
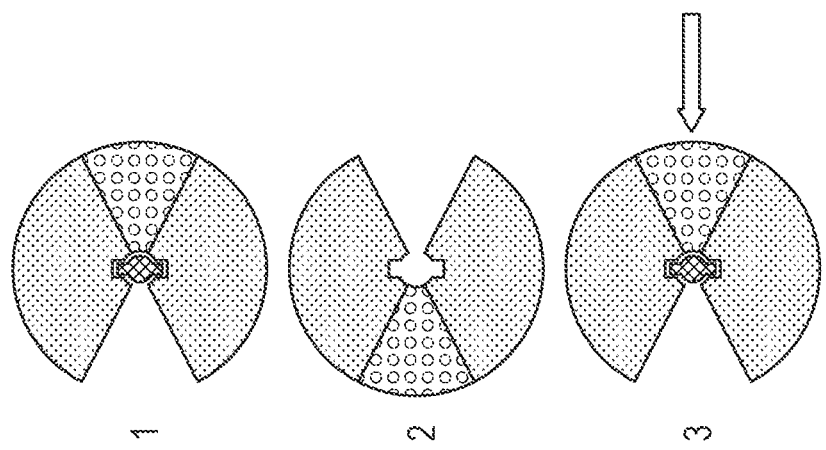
Figure 20F:
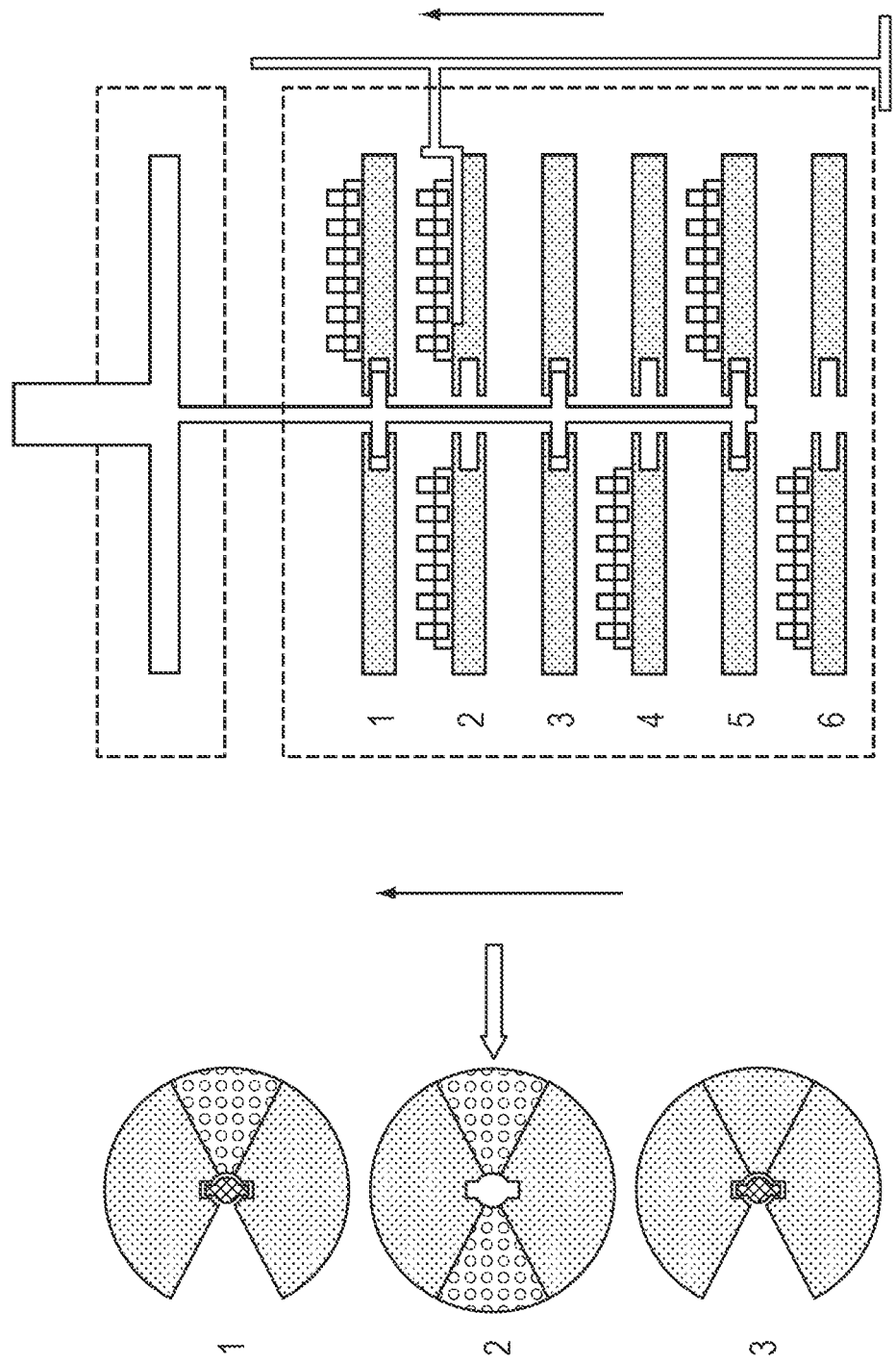
Figure 20G:
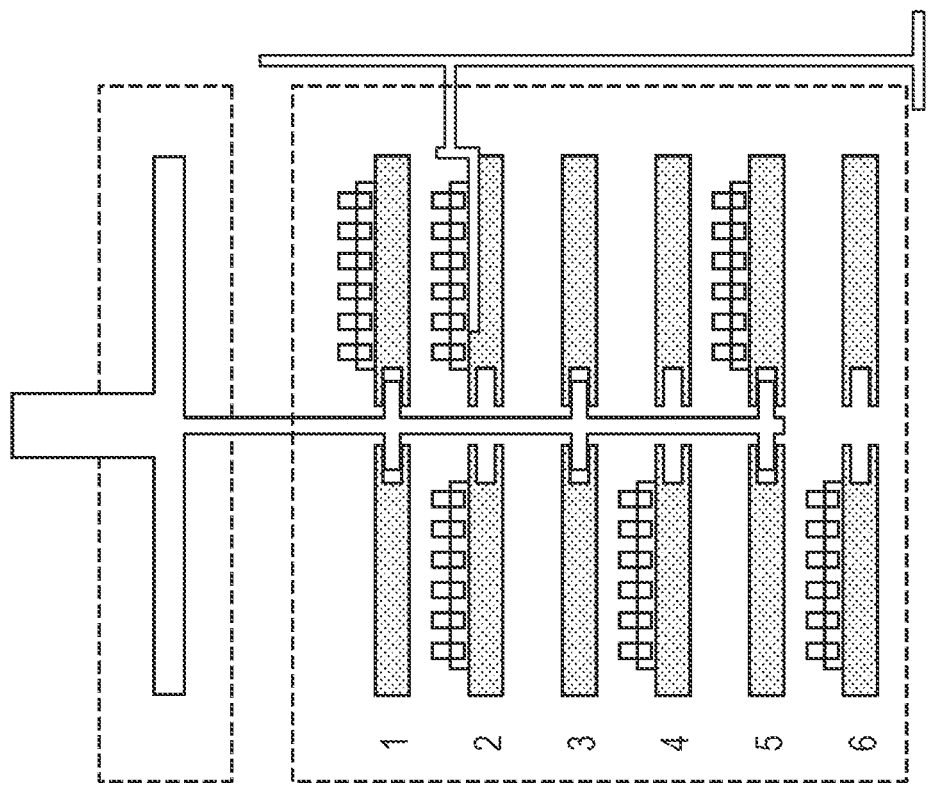
Figure 20G:
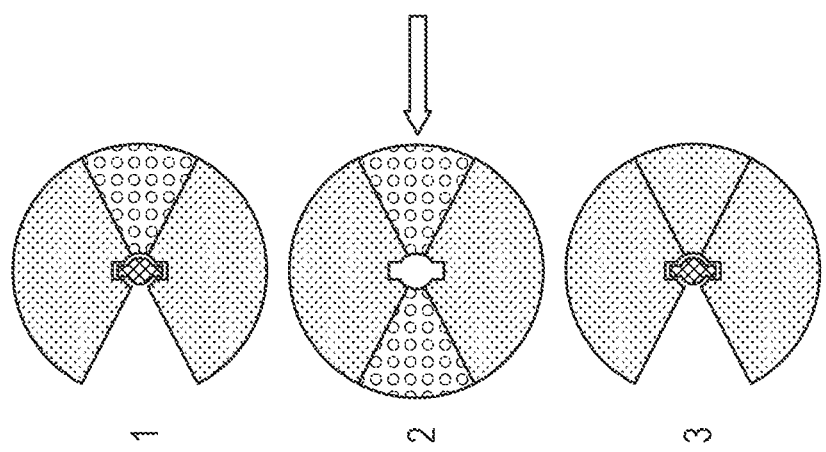
Figure 20I:
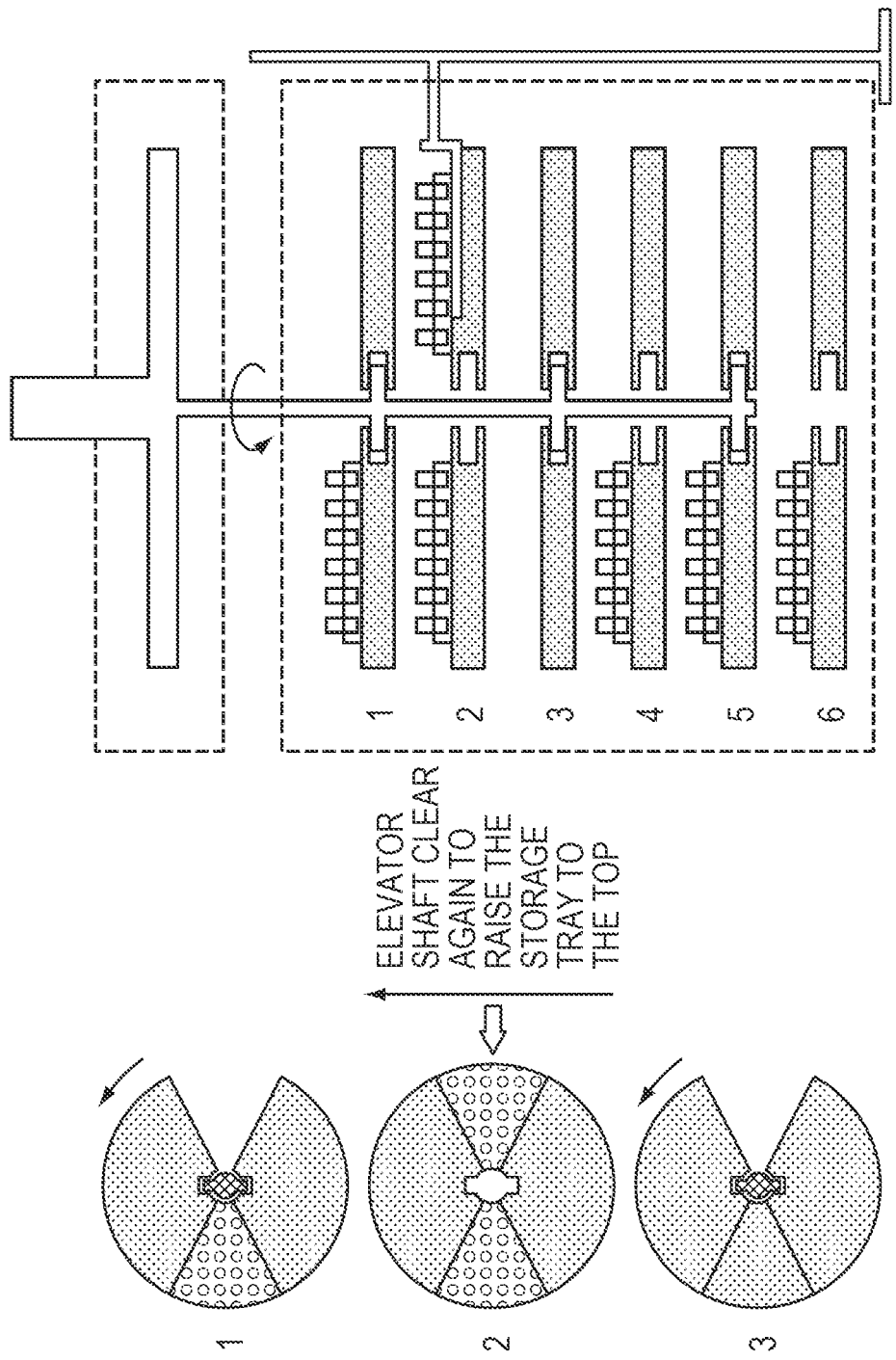
Figure 20J:
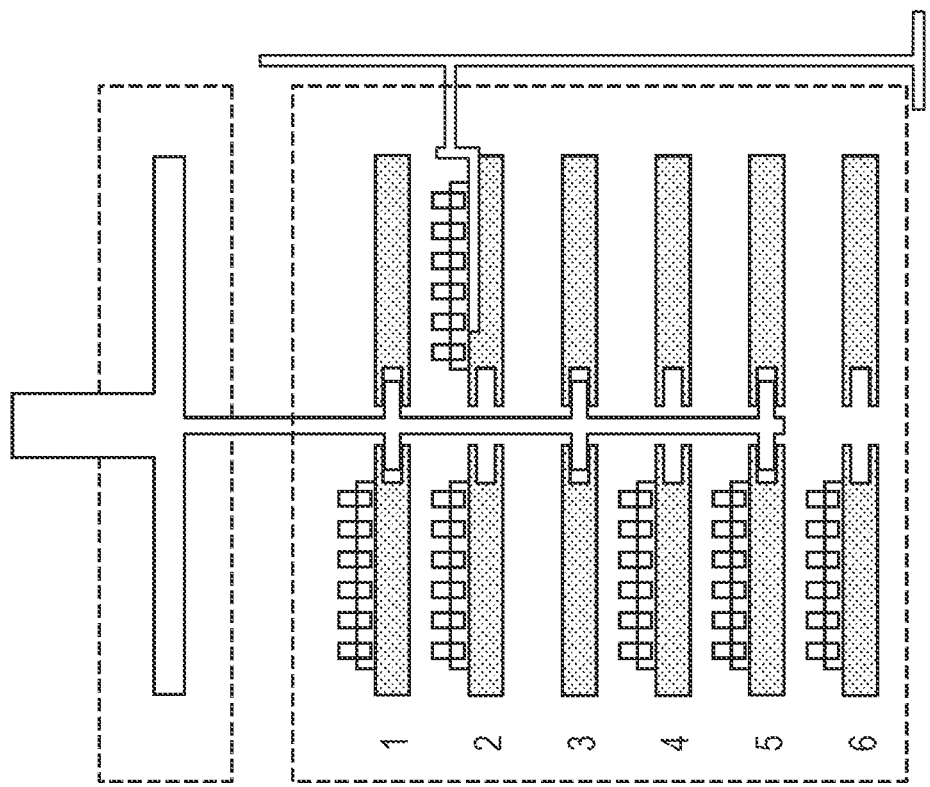
Figure 20J:
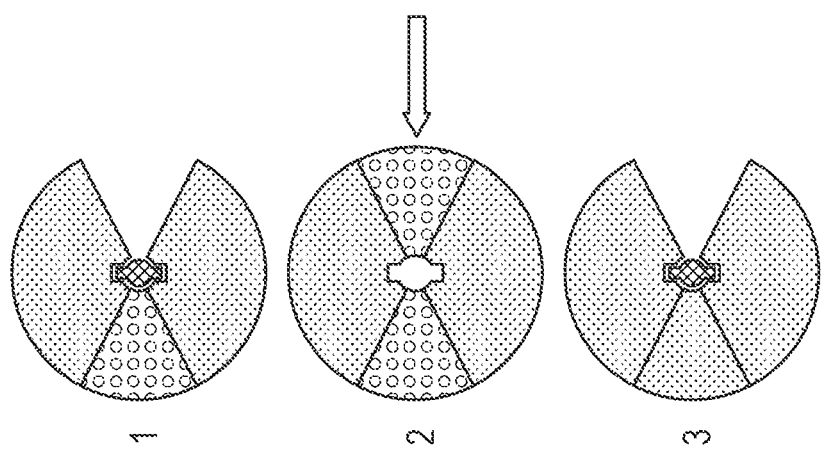
Figure 20K:
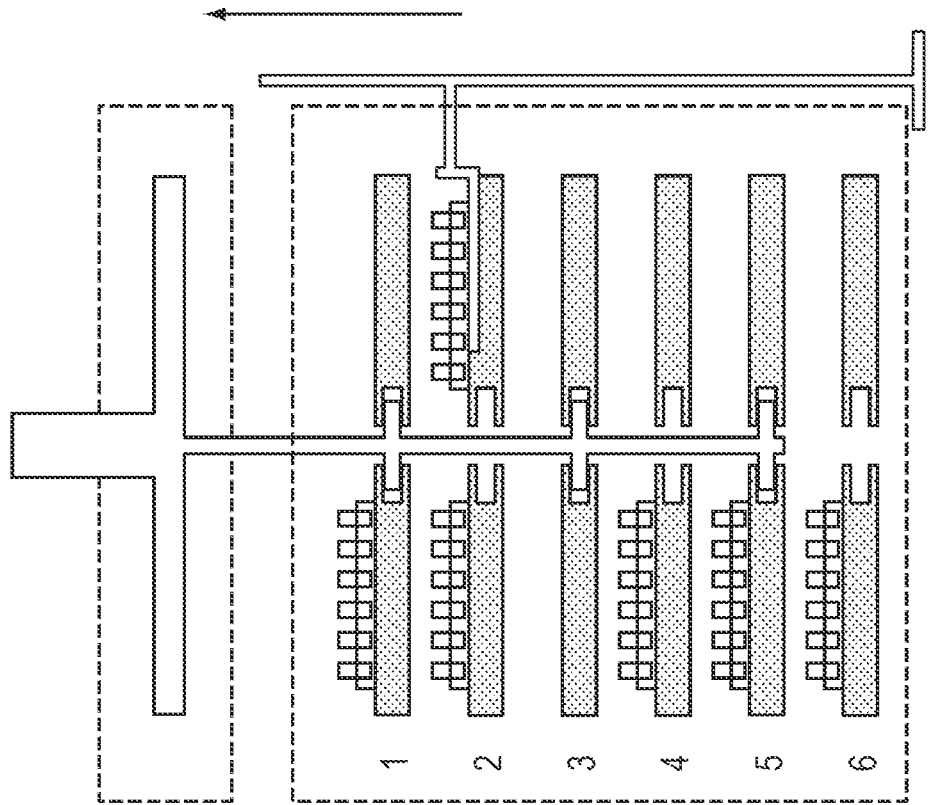
Figure 20K:
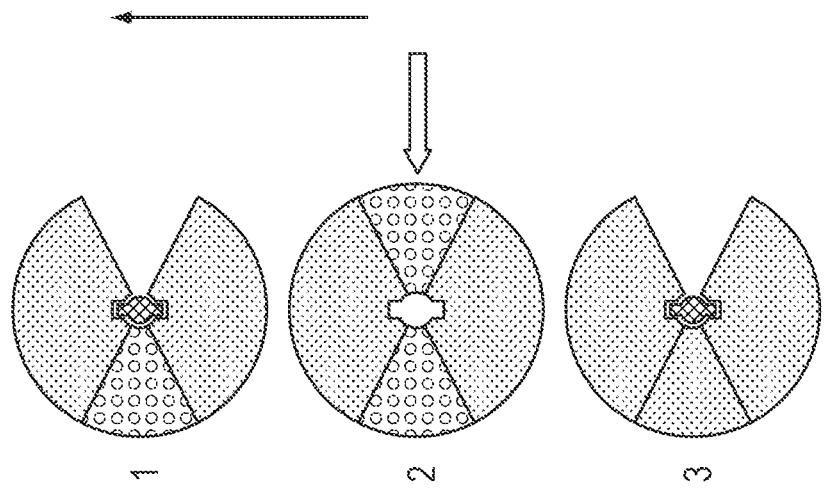
Figure 20L:
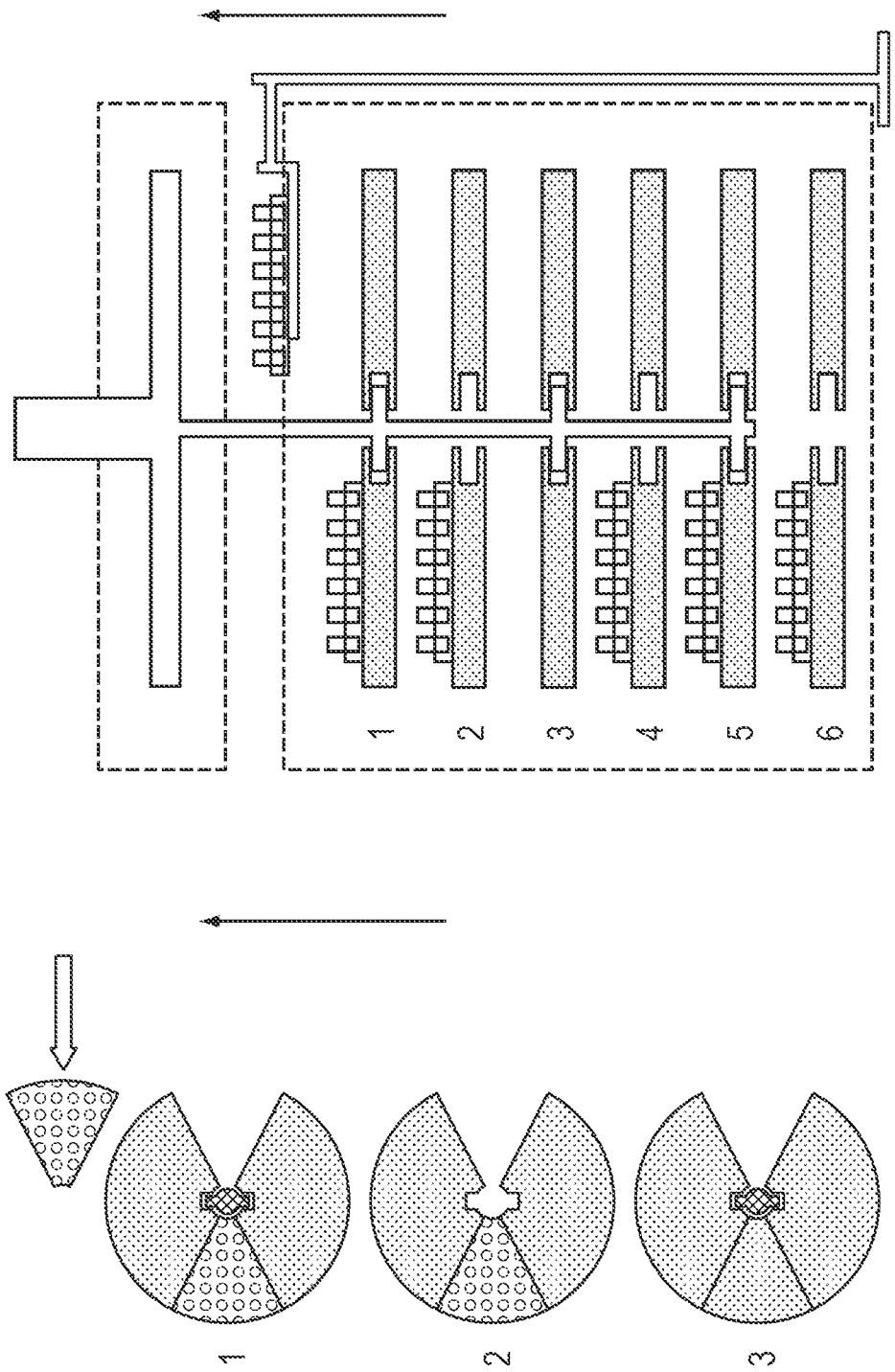
Figure 20M:
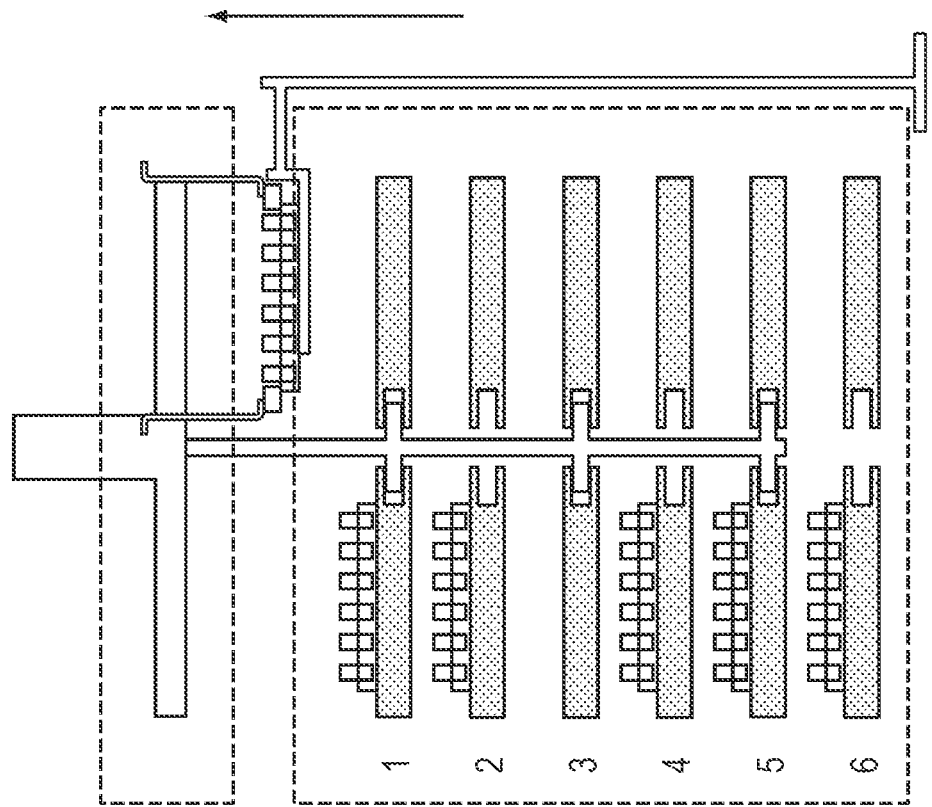
Figure 20M:
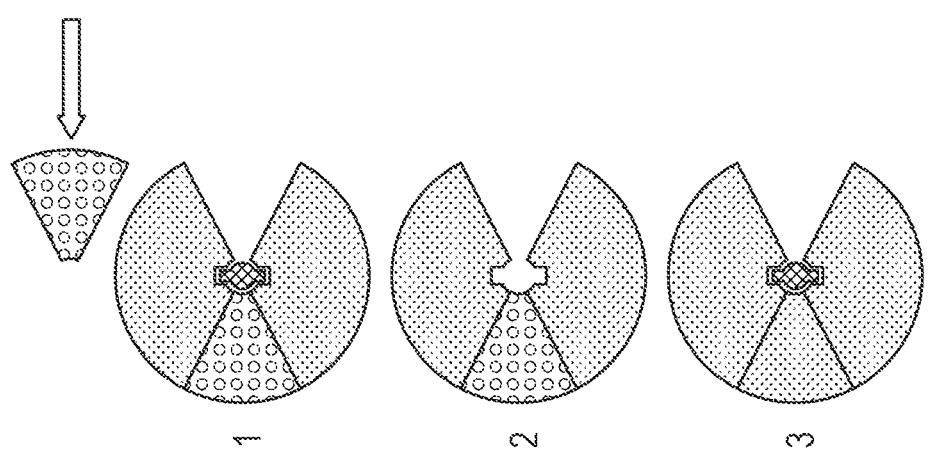

With reference to FIG. 19, and as shown in FIG. 20A, at a starting position, the vertical shuttle assembly 1300 is located at a top portion of the storage vault 510, and all of the shelves are aligned to form a vertical column ("elevator shaft") below the shuttle (1905). As shown in FIG. 20B, the shuttle is lowered to a position below the target shelf 3 (1910). As shown in FIGS. 20C-D, the target shelf is rotated until the target tray is located directly above the vertical shuttle (1915). Because the shelves are linked by common actuators in an interleaved manner, rotating the target shelf 3 also rotates all of the "odd" numbered shelves, including shelf 1. Following the positioning of the target tray, the vertical shuttle contacts the tray and lifts the tray to a level above the target shelf 3 (i.e., the level of shelf 2), as shown in FIGS. 20E-G (1920). As shown in FIGS. 20H-J, the target shelf (and all odd-numbered shelves) are then rotated back to a starting position, thereby returning clearance to the vertical shuttle (1925). Lastly, as shown in FIGS. K-M, the vertical shuttle may elevate the tray to a threshold of the vault opening for access the samples held by the tray (1930).

Figure 21:
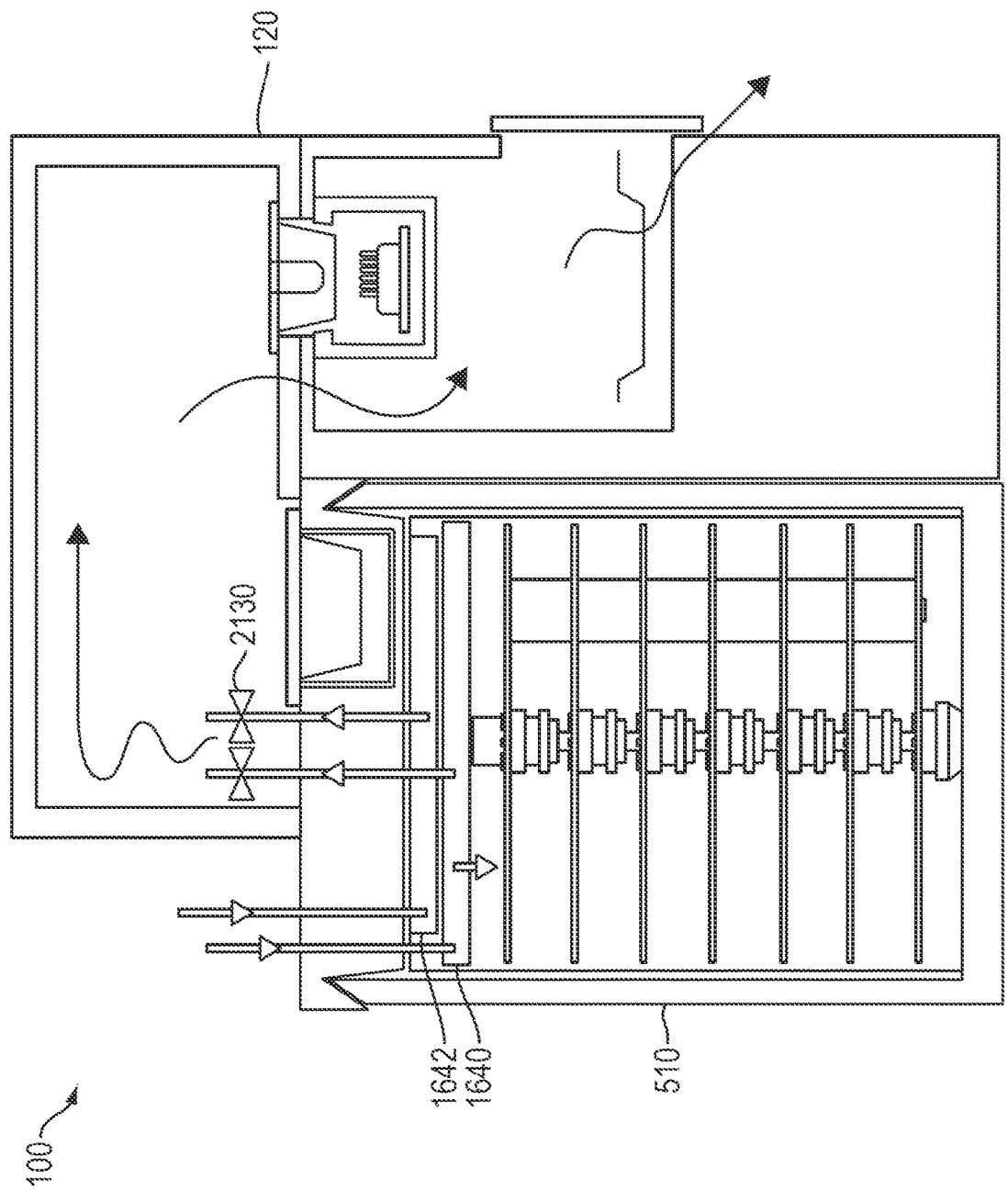
FIG. 21 is a schematic illustration of a refrigeration system in one embodiment.
Figure 22:
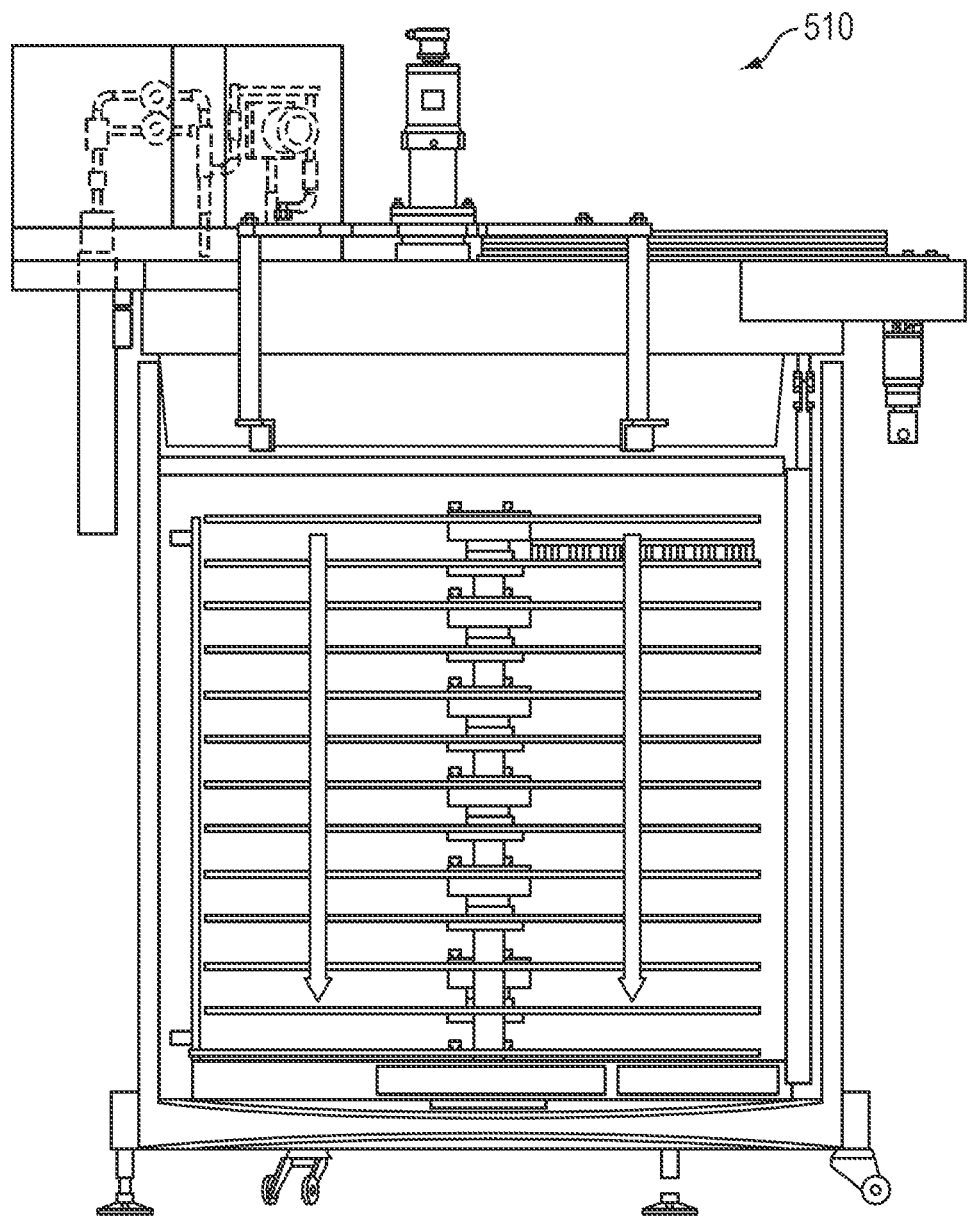
FIG. 22 illustrates cooling within a vault provided by a refrigeration system.

FIGS. 21-22 illustrate a refrigeration system that may be implemented in one embodiment. As shown in FIG. 21, the cryogenic storage system 100 may include a storage vault 510 and a sample handling module (SHM) 120 having an external port 130 as previously described above. Primary and/or secondary refrigeration coils 1640, 1642 circulate a refrigerant (e.g., liquid nitrogen that is piped to the coils from an external Dewar or mini-bulk tank) to maintain a cryogenic environment within the storage vault 510. In one embodiment, the primary coil 1640 includes one or more of small perforations (e.g., orifices under 1 mm in diameter). These perforations allow some of the liquid refrigerant to evaporate, forming a gas (e.g., nitrogen gas) within the top portion inside of the storage vault. As shown in FIG. 22, the gas gradually falls toward the bottom of the vault interior, providing a "cold/dry gas bath" effect to control temperature and/or moisture within the cryogenic environment. The gas may provide a positive pressure of cold dry gas that helps to prevent moisture ingress to the storage vault. The gas may also be expelled into SHM 120 when the opening to the SHM 120 is exposed during a transfer. The primary coil 1640, in enabling this evaporation, also provides a constant bleed of pressure into the storage vault 510 interior, aiding in the removal of moisture within the storage vault 510. The secondary coil 1642 may be a closed coil without such perforations, or, in an alternative embodiment, may be similarly perforated.

Turning again to FIG. 21, in some embodiments, solenoid valves 2130 may extend from the coils 1640, 1642 to the chamber of the SHM 120. The valves 2130 enable a controlled amount of refrigerant gas to vent to the SHM 120, which can aid in controlling temperature and moisture within the SHM 120. By positioning the solenoid valves 2130 "downstream" from the coils 1640, 1642, refrigerant consumption can be reduced, as the heat load added to the refrigerant by the solenoid valves 2130 occurs only after the refrigerant has cooled the storage vault 510.

In some embodiments, the refrigeration system does not contain refrigeration coils and instead a quantity of free cryogen (e.g., liquid nitrogen) is introduced to the storage vault at periodic intervals. The cryogen may form a pool beneath the sample storage area in the storage vault. In some embodiments, liquid cryogen is prevented from directly contacting the stored samples during its introduction to the storage vault.

Figure 23A:
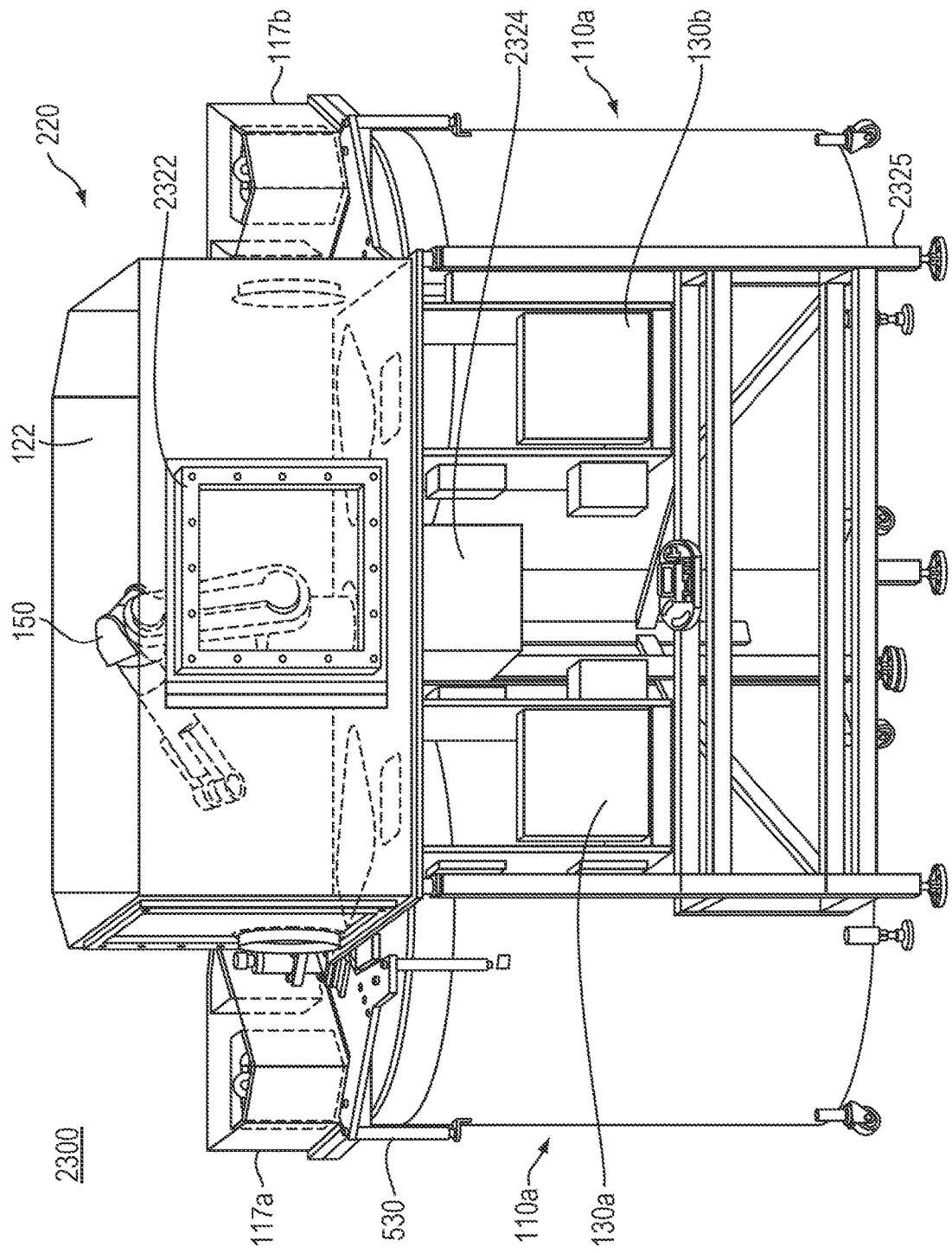
FIGS. 23A-B are schematic illustrations of an automatic cryogenic storage system including a sample handling module with a sample transfer robot in accordance with one embodiment.

FIG. 23A is a front-perspective view of an automatic cryogenic storage system 2300 including a SHM 2320 with a sample transfer robot 150 in accordance with aspects of the disclosed embodiment. Embodiments of an automated cryogenic storage system 2300 include one or more cryogenic storage vaults 110a-b connected to a SHM 2320 which is supported by a frame 2325 and the vaults 110. The SHM 2320 interfaces with the lid 530 of the cryogenic storage vault 110a to enable a sample transfer robot 150 to access the cryogenic storage vault 110a-b. The SHM 2320 has an enclosure 122 which contains a sealed environment and may include one or more maintenance access hatches 2322. The SHM 2320 has one or more ports 130a-b configured to dock a removable cryogenic storage device, such as a portable cryogenic workstation 190, and enable the sample transfer robot to deliver or remove samples from a docked portable cryogenic workstation 190. The SHM 2320 may be connected to the refrigeration system 1 and receive exhaust gas flow from the cryogenic storage vaults 110a-b to lower the humidity inside the SHM 2320. The temperature inside the SHM 2320 may be kept, for example, around ambient temperature or colder, such as less than about 5° C. In some embodiments, dew point is controlled within the SHM using one or more of temperature control; introduction of dry gas from the storage vault and/or refrigeration coils 1640, 1642 to the SHM; and removal of water from the SHM by a dehumidifier device. In some embodiments, the dew point of the air in the SHM is controlled to be, for example, less than about −50° C. The sample transfer robot 150 may be a standard 6 axis robot equipped with a gripper (not show) to secure a protect samples during a transfer. The operations of the sample transfer robot 150 and gripper are detailed in FIGS. 26-30. A transfer may include, for example, picking a sample from inside a first cryogenic storage vault 110a (kept at −150° C.) and quickly moving it to a second cryogenic storage vault 110b (also kept at −150° C.). A transfer may also include picking a sample from inside a first cryogenic storage vault 110a at −150° C. and placing the sample inside a docked portable cryogenic workstation 190 (not shown), where the inside of the portable cryogenic workstation 190 is also −150° C. The details and operation of the SHM 2320 and portable cryogenic workstation 190 are detailed in FIGS. 31 and 32.

Figure 23B:
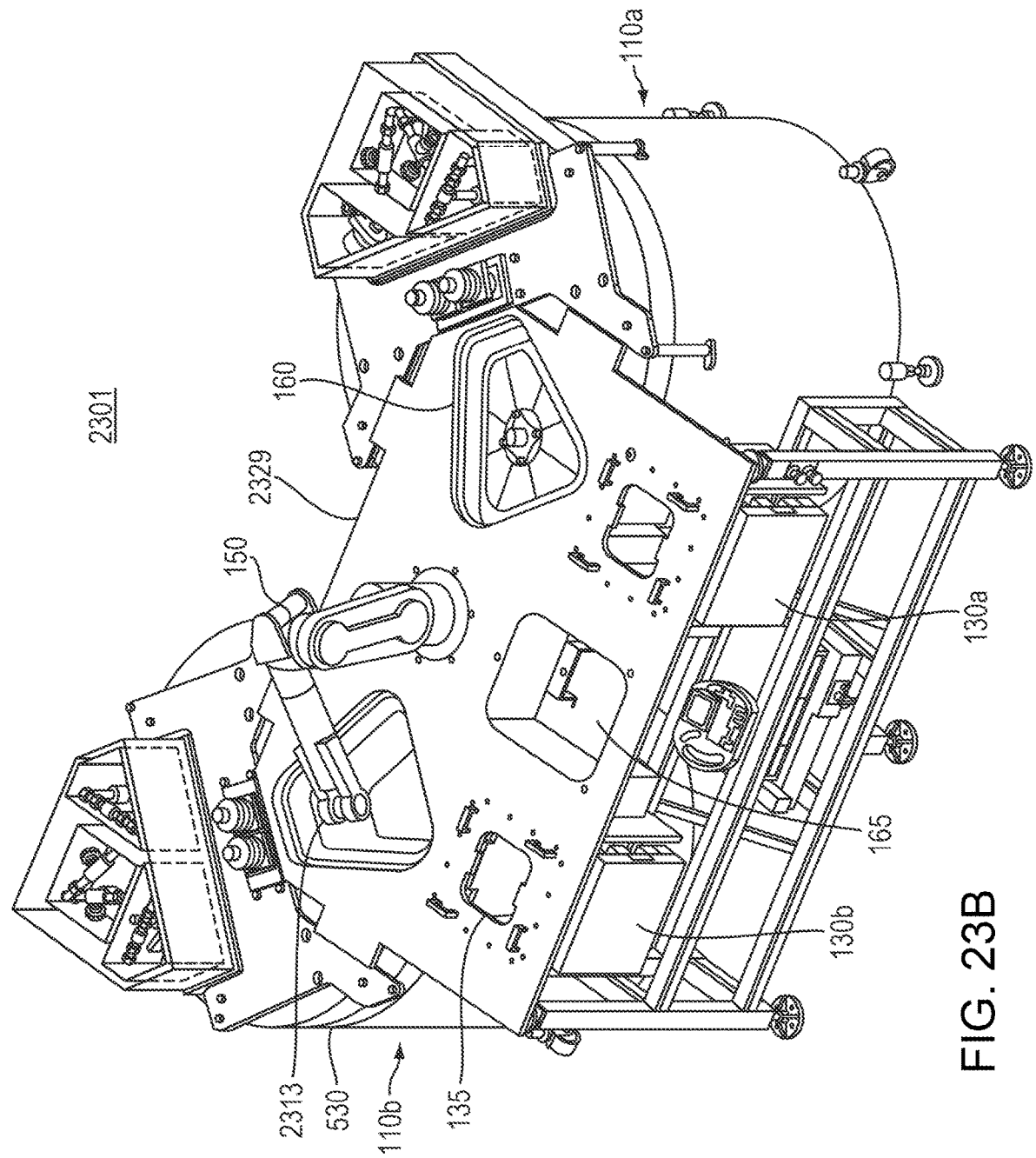

FIG. 23B is a top-down perspective view of an automatic cryogenic storage system 2301 including a SHM 2320 with an exterior housing of the SHM 2320 removed to show interior details in accordance with aspects of the disclosed embodiment. FIG. 23B shows an automated cryogenic storage system 2301 with the enclosure (122 in FIG. 23A) of the SHM (2320 in FIG. 23A) removed to show the lower SHM assembly 2329 of the SHM (2320 in FIB. 23A). The lower SHM assembly 2329 attaches to one or more cryogenic storage vaults 110a-b about vault openings 2337 that provide access to a vault cover 160 and a threshold 2313 of a cryogenic storage vault 110 when the cover 160 is removed. The lower SHM assembly 2329 may also include one or more portable cryogenic workstation dock positions 2311, also referred to as cryodocks, which allow the sample transfer robot 150 to access a docked portable cryogenic workstation 190 (not shown) and a vault cover parking position 165 to temporarily receive a vault cover 160 removed by the sample transfer robot 150 during a transfer in or out of a cryogenic storage vault 110*a-b*. The sample transfer robot 150 may be configured to interface with the vault cover 160 and place it in the vault cover parking position 165 during access to the cryogenic storage vaults 110*a-b*. The sample transfer robot 150 may be any commercial 6-axis robot able to transfer covers and samples using an attached gripper (not shown), for example, the Staubli TX60 L.

Figure 24:
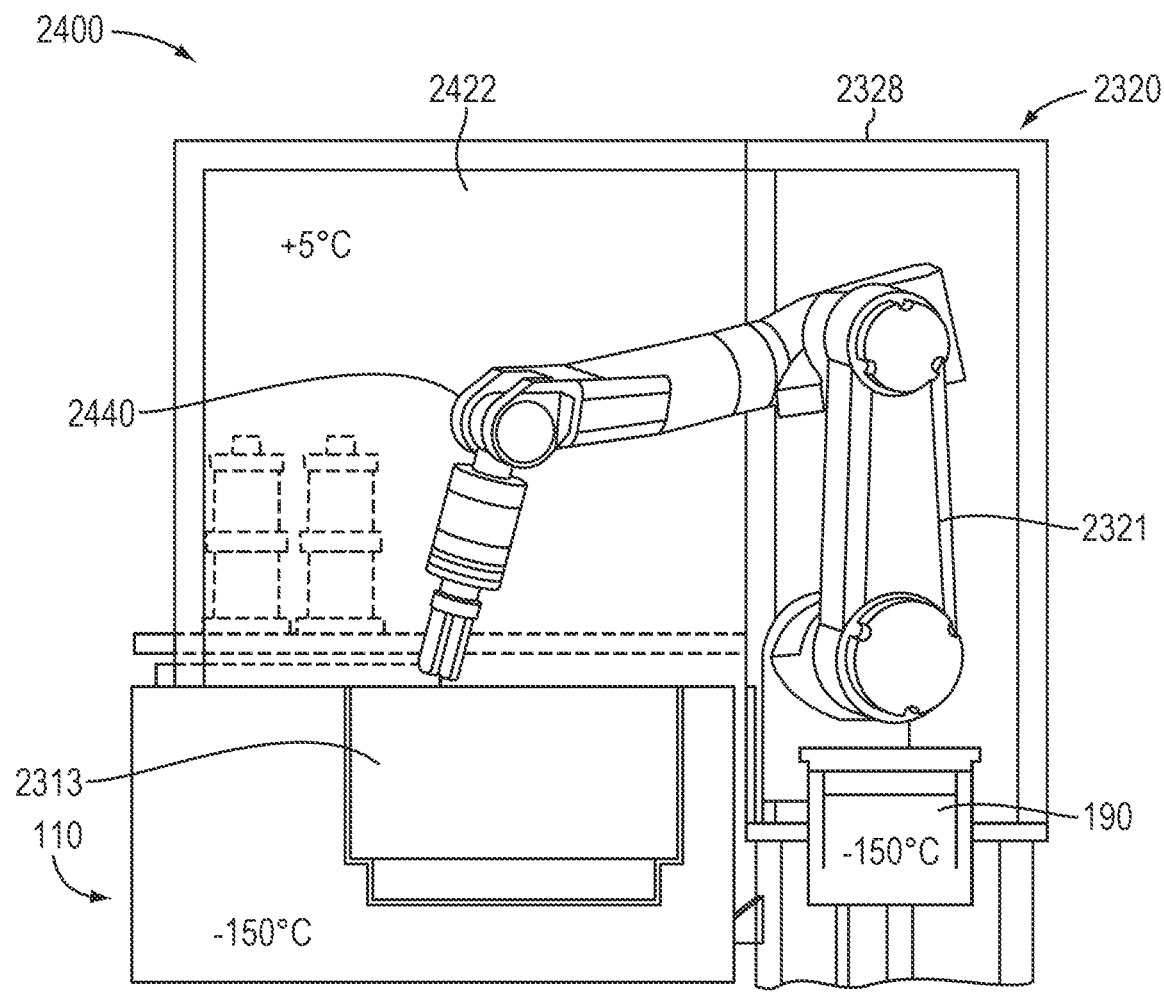
FIG. 24 is a cross-section illustration of an automatic cryogenic storage system including a sample handling module with a sample transfer robot configured to access two cryogenic storage environments in accordance with aspects of the disclosed example embodiment.

FIG. 24 is a cross-section illustration of an automatic cryogenic storage system 2400 including a SHM 2320 with a sample transfer robot 150 configured to access two cryogenic storage environments in accordance with aspects of the disclosed embodiment. FIG. 24 shows a cross section of an automated cryogenic storage system 2400 with a SHM 2320 attached to a cryogenic storage vault 110. Additionally, a portable cryogenic workstation 190 is docked to the SHM 2320. The cryogenic storage vault 110 and the portable cryogenic workstation 190 both have environments maintained at or below −150° C. The enclosure 122 of the SHM 2320 contains an internal environment 2422 with an appropriate temperature and humidity level. A sample handing robot 150 in the sample handing module 2320 includes a gripper 2644 configured to secure individual samples (not shown) in the cryogenic storage vault 110 or the portable cryogenic workstation 190 and transfer a sample between the two environments without the sample's temperature rising above the glass transition of water, i.e., −134° C. In some embodiments, this transfer takes place in less than 15 seconds, and in other embodiments this transfer takes less than 5 seconds.

A sample operation follows: (i) A portable cryogenic workstation 19 is placed in the cryodock (135 in FIG. 23A) by an operator. (ii) The portable cryogenic workstation 190 is lifted to seal with the lower SHM assembly (2329 in FIG. 23B). (iii) The cryogenic storage vault 110 positions a tray (not shown) in a picking position in the threshold 2313 at the top of the vault. The sample transfer robot 150 removes the cryoport cover (not shown) and places it in the vault cover parking position (165 in FIG. 24B). (v) The sample transfer robot 150 removes the vault cover (160 in FIG. 23B) and places it in the vault cover parking position (165 in FIG. 24B). (vi) The sample handing robot 150 secures an individual sample tube (not shown) out of the tray in the threshold (2313 of FIG. 23B). (vii) The sample handing robot 150 places the sample tube (not shown) into the portable cryogenic workstation 190 and may repeat the preceding two steps for a plurality of sample tubes to be transferred. (viii) The sample handing robot 150 replaces the vault cover (160 in FIG. 23B) to seal the cryogenic storage vault 110. (ix) The sample handing robot 150 replaces the cryoport cover (not shown). (x) The portable cryogenic workstation 190 is lowered away from the lower SHM assembly (2329 in FIG. 23B). And (xi), the portable cryogenic workstation 190 is removed by an operator.

Figure 25:
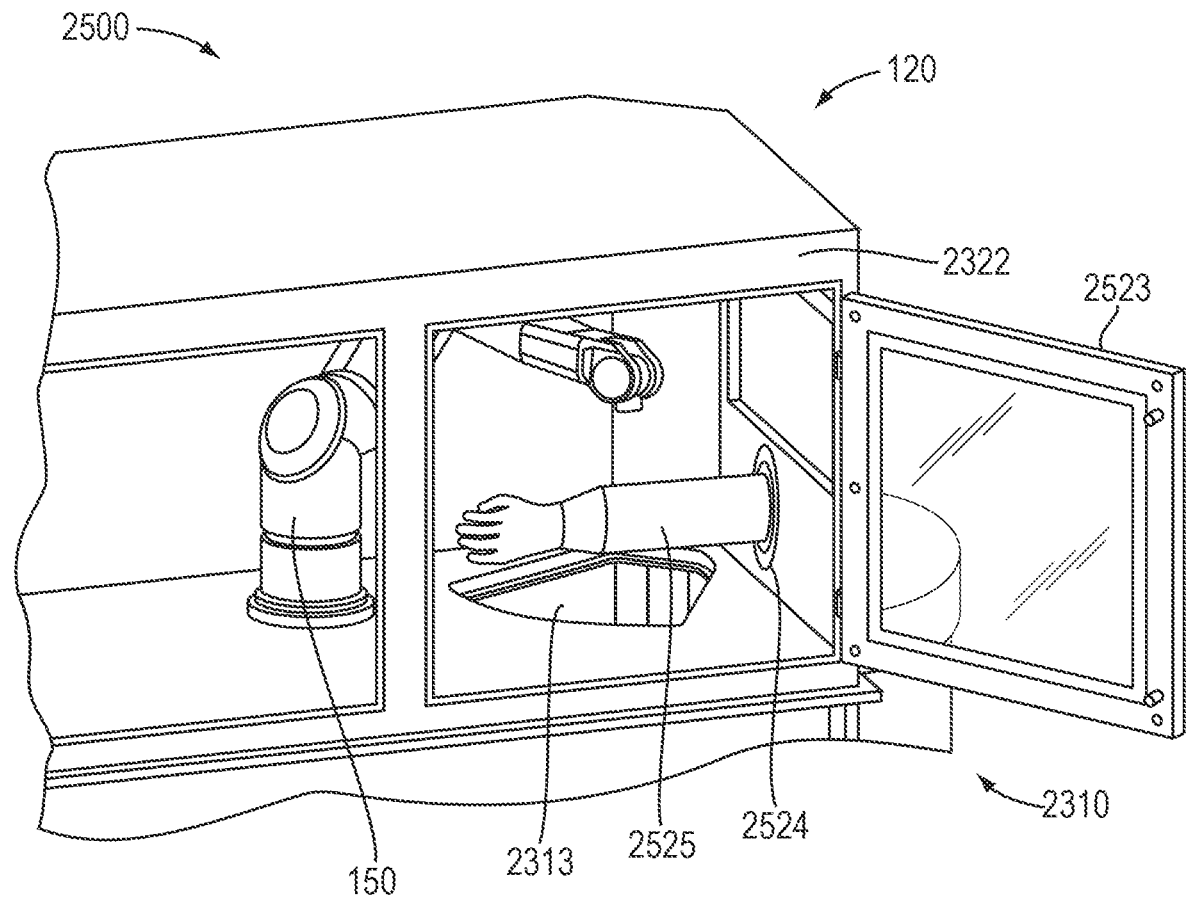
FIG. 25 is a schematic illustration of a sample handling module having an open exterior hatch to show interior details in accordance with aspects of the disclosed example embodiment.

FIG. 25 is an illustration of a SHM 120 having an open exterior hatch to show interior details in accordance with aspects of the disclosed embodiment. FIG. 25 shows an automated cryogenic storage system 2500 having a SHM 120 attached to a cryogenic storage vault 110. The SHM 120 includes two maintenance hatches 2322 with corresponding doors 2523 for sealing the hatches 2322. The doors 2523 may include operator viewing window for ease of use. Inside the SHM 120 is a sample transfer robot 150 and a glove port 2524 comprising rubber glove 2525, with heated internal glove, permits user or maintenance access to an upper section, for example, a threshold 160, of the cryogenic storage vault 110, and in particular a storage tray (not shown) datumed in the threshold 2313, for easy recovery of misplaced samples, etc. An external (interlocked) cover may be normally fitted to glove port 2524 to prevent moisture ingress into SHM 120 and ensure operator safety.

Figure 26B:
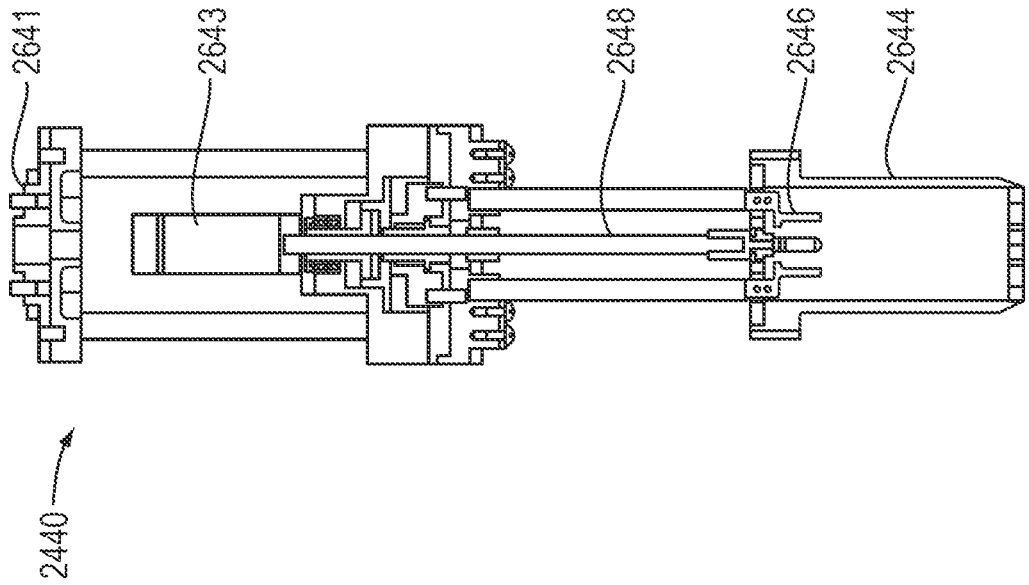
FIGS. 26A-B are perspective and cross-section views, respectively, of a gripper configured to be attached to the end of a sample transfer robot in accordance with aspects of the disclosed embodiment.
Figure 26A:
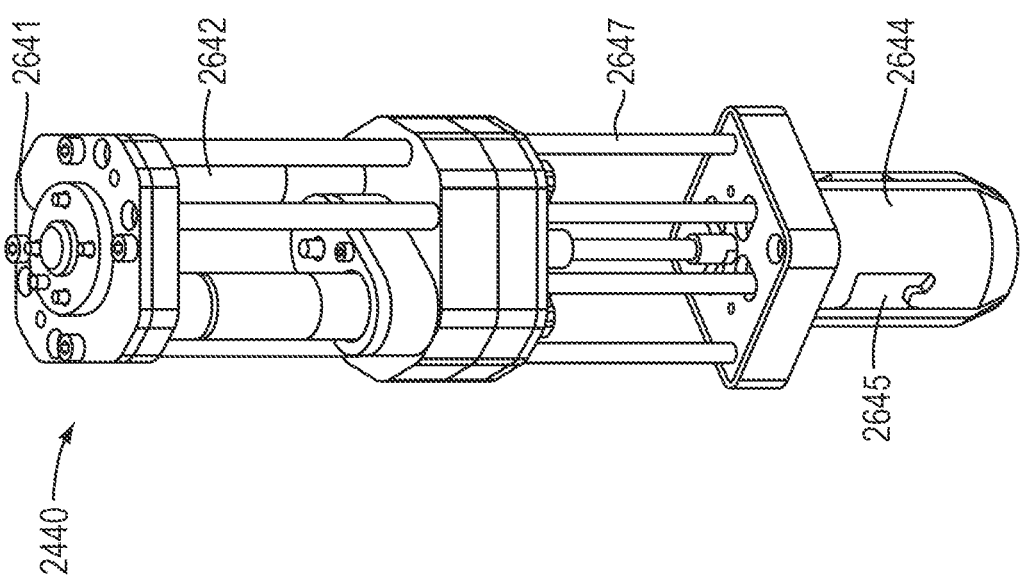

FIGS. 26A-B are perspective and cross-section views, respectively, of a gripper 2644 configured to be attached to the end of a sample transfer robot 150 in accordance with aspects of the disclosed embodiment. FIG. 26A shows a gripper 2644 adapted to be fitted to a sample transfer robot (150 of FIG. 23A) via a robot interface 2641. The gripper 2644 includes an extendable insulating sleeve 2644 driven by a first servo motor 2642. The first servo motor 2642 drives sleeve lead screws 2647 which translate the extendable insulating sleeve 2644. The extendable insulating sleeve 2644 also includes one or more grooves 2645 for interfacing with corresponding pegs (not shown) on a vault door cover locking mechanism (as show in FIG. 27).

FIG. 26B shows a cross sections of the gripper 2644 of FIG. 26A. The gripper 2644 includes parallel action picking fingers 2646 inside the extendable insulating sleeve 2644 to secure an individual sample tube (as shown in FIGS. 30A-D). A second servo motor 2643 drives a picker lead screw 2648 which opens and closes the picking fingers 2646 in the extendable insulating sleeve 2644. The extendable insulating sleeve 2644 may be adapted to protect a sample tube (not shown) during transfer by extending to completely surrounding it and further extends the transfer window time by decreasing heat soak from the environment outside the extendable insulating sleeve 2644. The extendable insulating sleeve 2644 may be made of, for example, expanded polystyrene.

Figure 27:
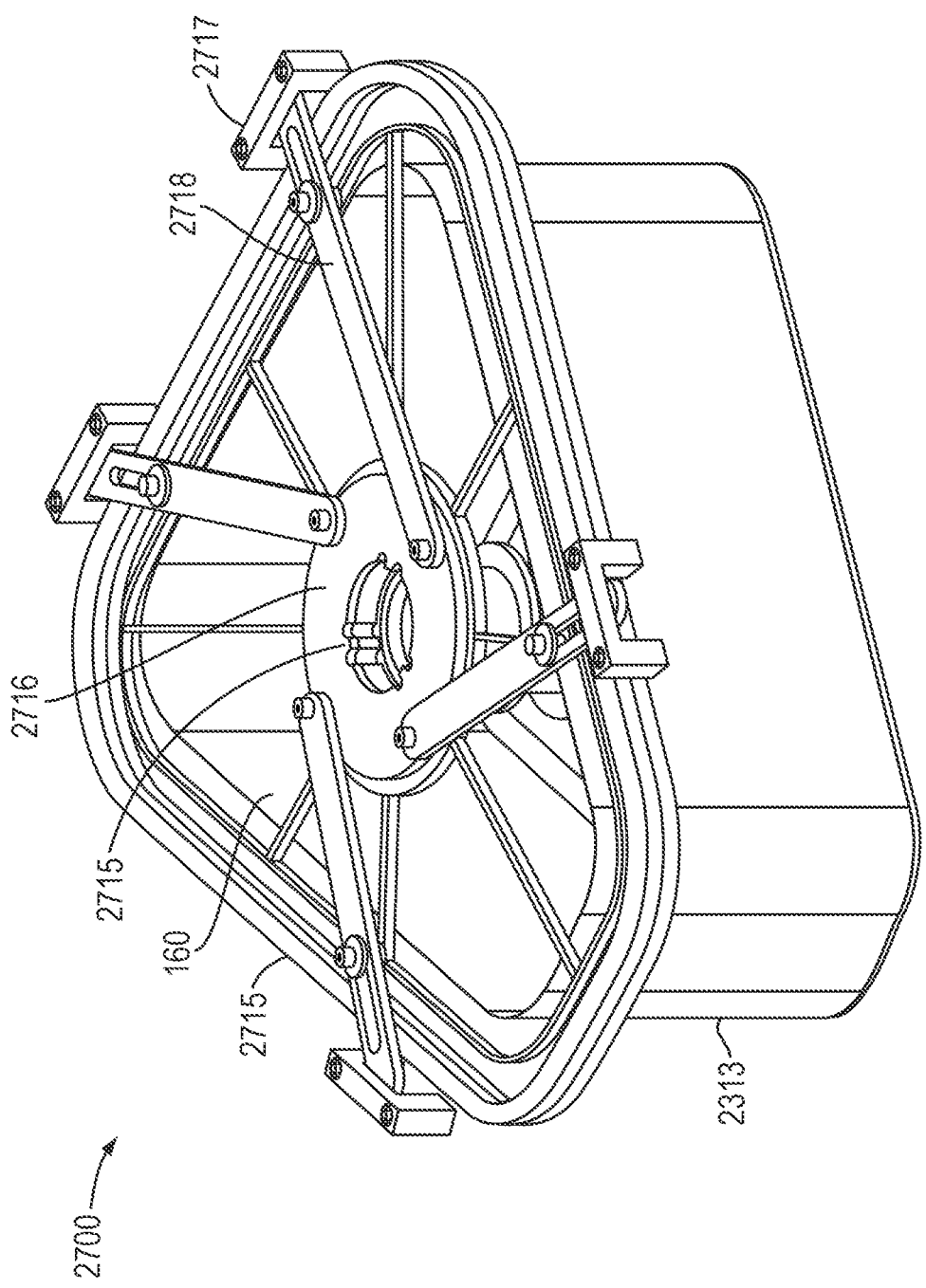
FIG. 27 is a perspective view of a vault access door and associated components in accordance with aspects of the disclosed embodiment.

FIG. 27 is a perspective view of a vault access door and associated components in accordance with aspects of the disclosed embodiment. FIG. 27 shows a vault access interface 2700 that includes a threshold 2313, a vault cover door 160, a hermetic seal 2715, a central rotating locking collar 2715 with gripper pegs 2715, locking bayonets 2718, and corresponding locking latches 2717. When attached, the central locking collar 2715 actuates the locking bayonets 2718 by sliding them into and out of their corresponding locking latches 2718. When the locking bayonets 2718 are engaged with the locking latches 2717, the vault cover door 160 is pressed against the hermetic seal 2715.

Figure 28:
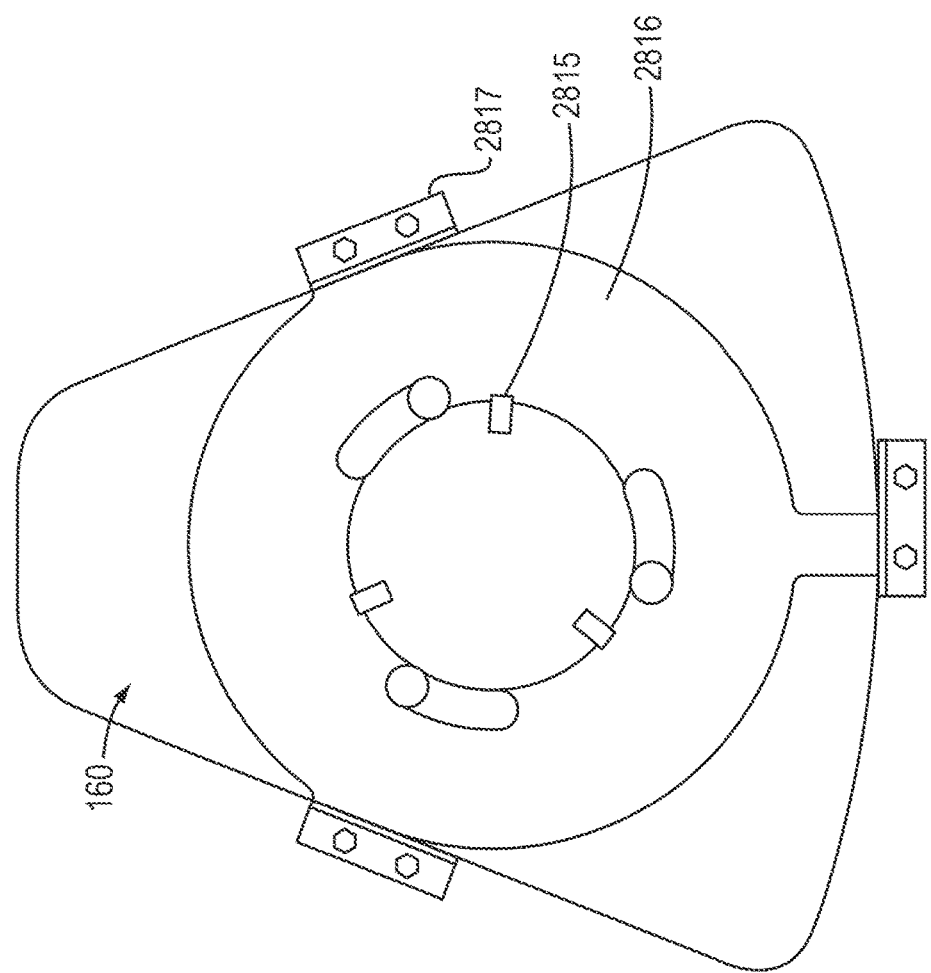
FIG. 28 is an illustration of a vault access cover and locking interface in accordance with aspects of the disclosed embodiment.

FIG. 28 is an illustration of a vault access cover and locking interface in accordance with aspects of the disclosed embodiment. FIG. 28 shows vault cover door 160 having a central locking collar 2816 with gripper pegs 2815, and rotating locks 2817. When the central locking collar 2816 is rotated by pegs 2815 in a clockwise direction, the rotating locks 2817 disengage and allow the vault cover door 160 to be lifted by the gripper pegs 2815.

Figure 29:
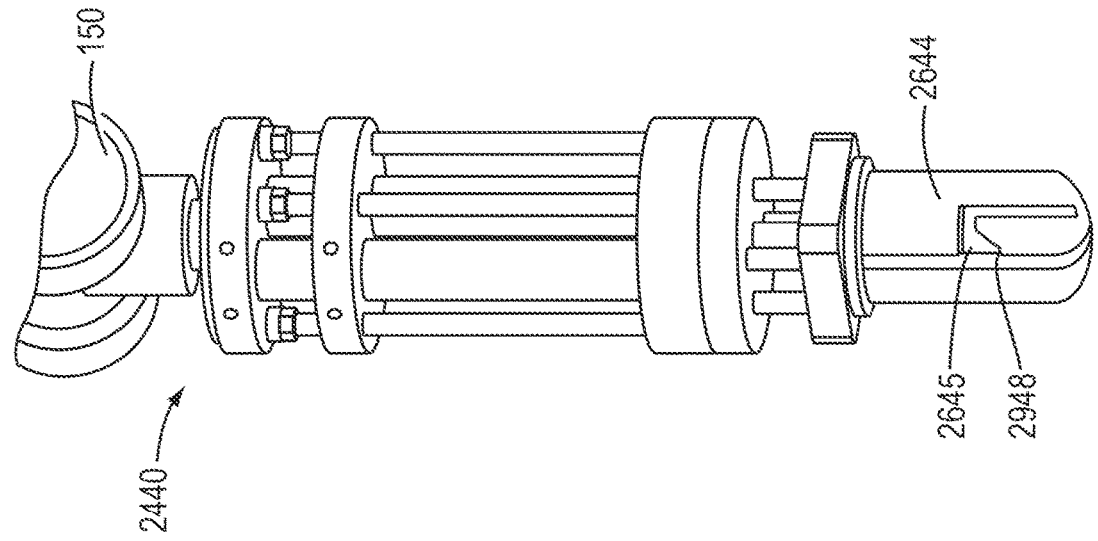
FIG. 29 is a photograph of a gripper configured to interface with the locking interface on the vault access door of FIG. 28 in accordance with aspects of the disclosed embodiment.

FIG. 29 is a photograph of a gripper 2644 configured to interface with the locking interface on the vault access door of FIG. 28 in accordance with aspects of the disclosed embodiment. FIG. 29 shows a gripper 2644 attached to a sample transfer robot 150. The gripper 2644 has an extending insulated sleeve 2943 with grooves 2645 configured to interface with the pegs on a vault cover door (2815 in FIG. 28). In operation, the sample transfer robot 150 lowers the extendable insulating sleeve 2943 of the gripper into a central locking collar (2816 of FIG. 28) having pegs (2815 of FIG. 28). The pegs (2815 of FIG. 28) slide along the length of the grooves 2645 and then the extendable insulating sleeve 2943 is rotated by the sample transfer robot 150 to disengage one or more rotating locks (2817 in FIG. 28). When the rotating locks are disengaged, the gripper 2644 moves the pegs (2815 of FIG. 28) into a lifting groove 2948 to enable the extendable insulating sleeve 2943 to lift the vault cover and transport it to, for example, a vault cover parking position (shown as 165 in FIG. 23B).

Figure 30A:
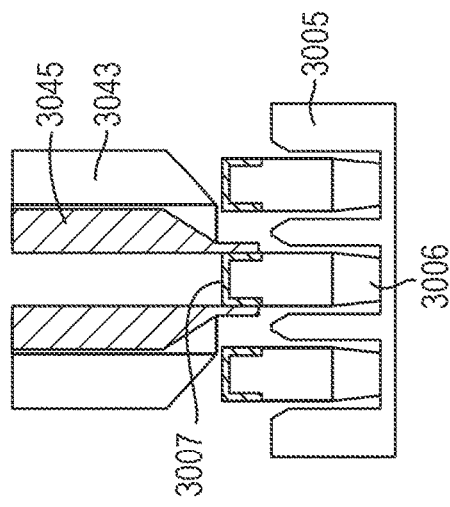
FIGS. 30A-D are cross-sectional illustrations of a gripper removing an individual sample tube from a tray in accordance with aspects of the disclosed embodiment.
Figure 30B:
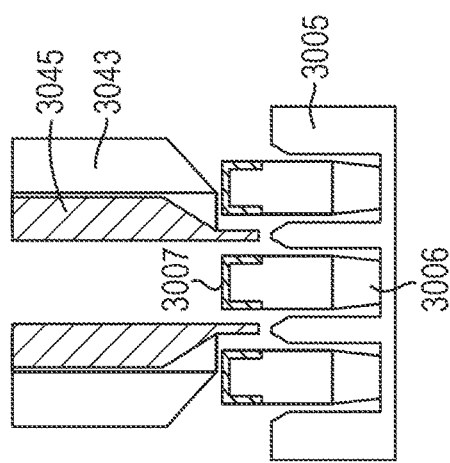
Figure 30C:
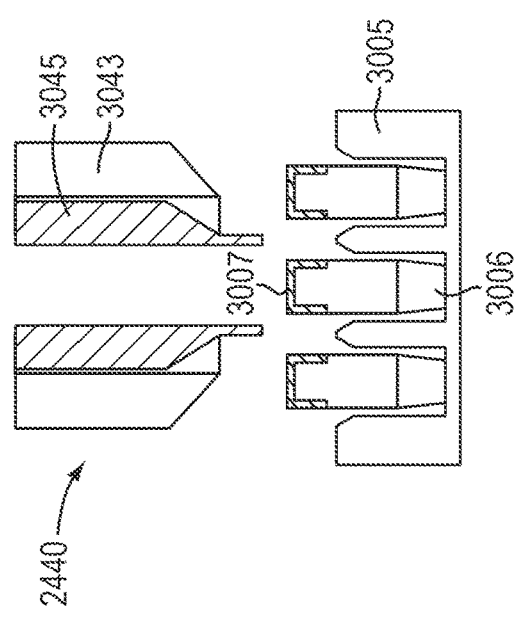
Figure 30D:
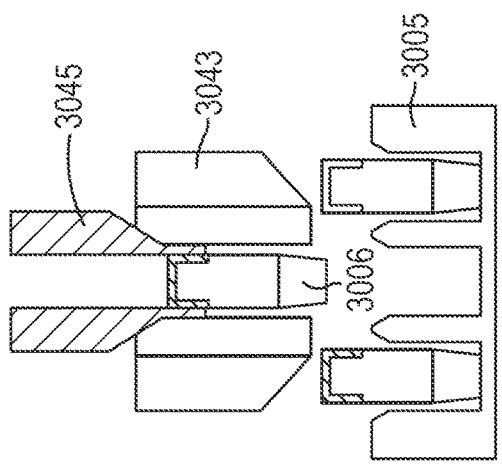

FIGS. 30A-D are cross-sectional illustrations of a gripper removing an individual sample tube 3006 from a tray 3005 in accordance with aspects of the disclosed embodiment. FIG. 30A shows a sample tray 3005 containing sample tubes 3006 with caps 3007. Typically, the sample tray 3005 is in a cryogenic environment and the samples contained need to be kept below a certain cryogenic temperature at all times, e.g., during a transfer. To reduce exposure of a sample to warm temperatures during a transfer through a non-cryogenic environment, for example, the enclosure of a SHM 2320, the gripper 2644 has picking fingers 3045 and an extendable insulating sleeve 3043 configured to extend over the picking fingers 3045. An example operation of the gripper 2644 is shown in FIGS. 30B-D. In FIG. 30B, the gripper 2644 descends toward to tray 3005 and aligns the picking fingers 3045 around a cap 3007 of a sample tube 3006 on the tray 3005. In FIG. 30C, the picking fingers 3045 of the gripper 2644 grasp the cap 3007 of a sample tube 3006 on the tray 2005. In FIG. 30D, the extendable insulating sleeve 3043 extends over the picking fingers 3045 holding the sample tube 3006. After the operation of FIG. 30D is complete, the sample transfer robot (not shown) may move the gripper 2644 and contained sample tube 3006 to a different cryogenic environment by transferring it through a non-cryogenic environment with the protection of the extendable insulating sleeve 3043.

The operation of the portable cryogenic workstation 190 of FIGS. 31A-B and the cryodock 135 of FIG. 23A-B are now discussed. The cryodock 135 is a receptacle configured to accept a removable cryogenic storage device, i.e., the portable cryogenic workstation, once placed in the cryoport (130 of FIG. 23A) and provide the sample transfer robot (150 of FIG. 23A) with access to an internal cryogenic storage environment of the portable cryogenic workstation. FIGS. 31A-B are illustrations of a removable cryogenic storage device in accordance with aspects of the disclosed embodiment. FIG. 31A shows a removable cryogenic storage device 190, also referred to as a portable cryogenic workstation, having an insulated lid 3152, also referred to as a portable cryogenic workstation cover, an insulated body 3151, and a handle 3156. FIG. 31B shows a cross-sectional view of the portable cryogenic workstation 190 of FIG. 31A. The body of the portable cryogenic workstation 3151 contains an inner chamber 3157 with a side-by-side (SBS) rack 3154, and insulation 3153, which may be, for example, expanded polystyrene, surrounding a bottom chamber 3155. The SBS rack 3154 may contain, for example, 48×2 ml FluidX tubes or 96x 1.4 ml Matrix tubes. The bottom chamber 3155 may contain a sponge adapted to be filled with nitrogen cryogen (e.g., liquid nitrogen). The portable cryogenic workstation 190 may be configured to hold samples in the SBS rack 3154 at −150° C. for up to 2 hours. The body of the portable cryogenic workstation 3151 is adapted to be placed into a cryoport (130 of FIG. 23A) and lifted into a sealing position with a cyodock (135 of FIG. 23B) of a SHM (2320 FIG. 23A) to be accessed by a sample transfer robot (150 of FIG. 23A). Portable cryogenic workstations suitable for use with the present invention are described in U.S. patent application Ser. No. 14/600,751, entitled "Portable Cryogenic Workstation," and 61/929,306, entitled "Sample Store," the entire contents of which are incorporated by reference herein.

Figure 32D:
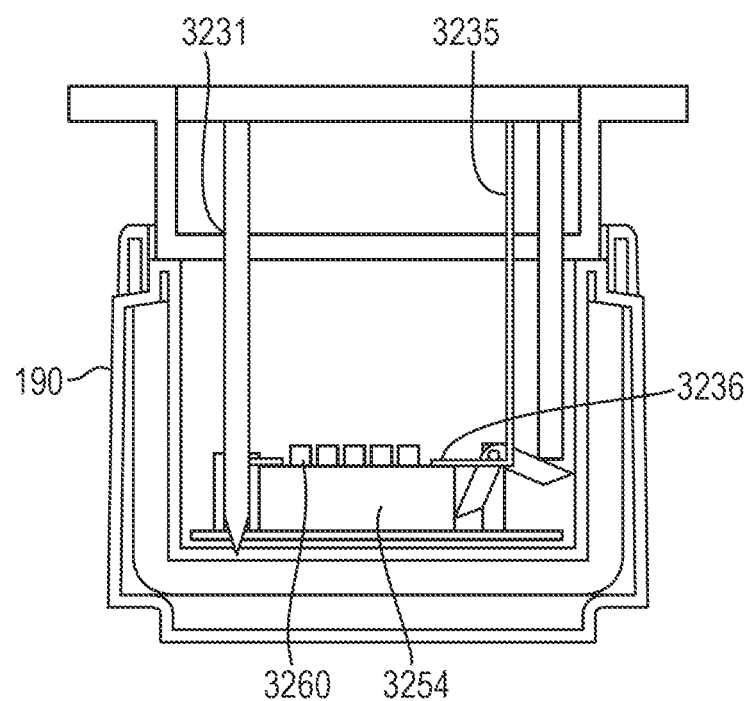

FIGS. 32A-D are illustrations of the interface between a SHM 2320 and a removable cryogenic storage device (e.g., portable cryogenic workstation, 190) in accordance with aspects of the disclosed embodiment. FIG. 32A shows a cryodock rack 3231 having a rack datum pin 3234, a rack actuating pin 3233, and a cryodock seal 3232. The cryodock rack 3231 is the interface between a portable cryogenic workstation 190 and the cryodock 135 in the SHM (120 of FIG. 23A). In operation, a portable cryogenic workstation 190, having been placed in a cryoport (130 of FIG. 23A), may be automatically moved vertically against the rack datum pin 3234, rack actuating pin 3233, and portable cryogenic workstation seal 3232 to dock the portable cryogenic workstation 190 to a SHM (2320 FIG. 23A). The docking may comprise the following four tasks in sequence: (i) aligning, (ii) clamping, (iii) seal compression, and (iv) Z movement prevention. FIG. 32B shows the portable cryogenic workstation 190 includes a floating rack carrier 3257 with an SBS rack 3254 and datum pin interface 3255. Following the closing of the cryoport door (130 in FIG. 23A), and before lifting the portable cryogenic workstation 190 to the picking position (shown in FIG. 32D) communication may take place between the cportable cryogenic workstation 190 and the automated cryogenic storage system (2300 of FIG. 23A), to establish if the temperature of the cportable cryogenic workstation 190 is suitable for input/output of samples to take place.

FIG. 32C shows the portable cryogenic workstation 190 lifted towards the cryodock rack 3231. The rack datum pin 3234 mates with the datum pin interface 3255 to center the floating rack carrier 3257 in the portable cryogenic workstation 190. The use of the floating rack carrier 3257 This divorces the positional accuracy of the portable cryogenic workstation 190 to the position accuracy of the cryodock rack 3231, making it easier to manufacture portable cryogenic workstation 190 whilst enabling reliable picking by a sample transfer robot 150. The rack actuating pin 3233 contacts the lever 3256 which is adapted to datum the SBS rack 3254 about the cryodock frame 3235, as shown in FIG. 32D. FIG. 32D shows the portable cryogenic workstation 190 lifted against the cryodock seal 3232. The rack actuating pin 3233 actuated the lever 3256, which in turn moved the SBS rack 3254 to line up with the cryodock frame 3235. A retainer lip 3236 is attached to the cryodock frame 3235 to prevent the SBS rack 3254 from being lifted during the picking of a contained sample tube 3260 by a sample transfer robot (150 of FIG. 23A). Additionally, during pick up and placement operations to and from the portable cryogenic workstation 190, a feature (not shown) may monitor the level of liquid nitrogen in the portable cryogenic workstation 190, to forewarn of possible temperature rise during the transfer. The portable cryogenic workstation 190 may also be automatically filled (or 'topped off') with more liquid nitrogen, to provide increased autonomy to the user once the portable cryogenic workstation 190 is removed with samples from the automated cryogenic storage system (2300 of FIG. 23A).

Figure 33B:
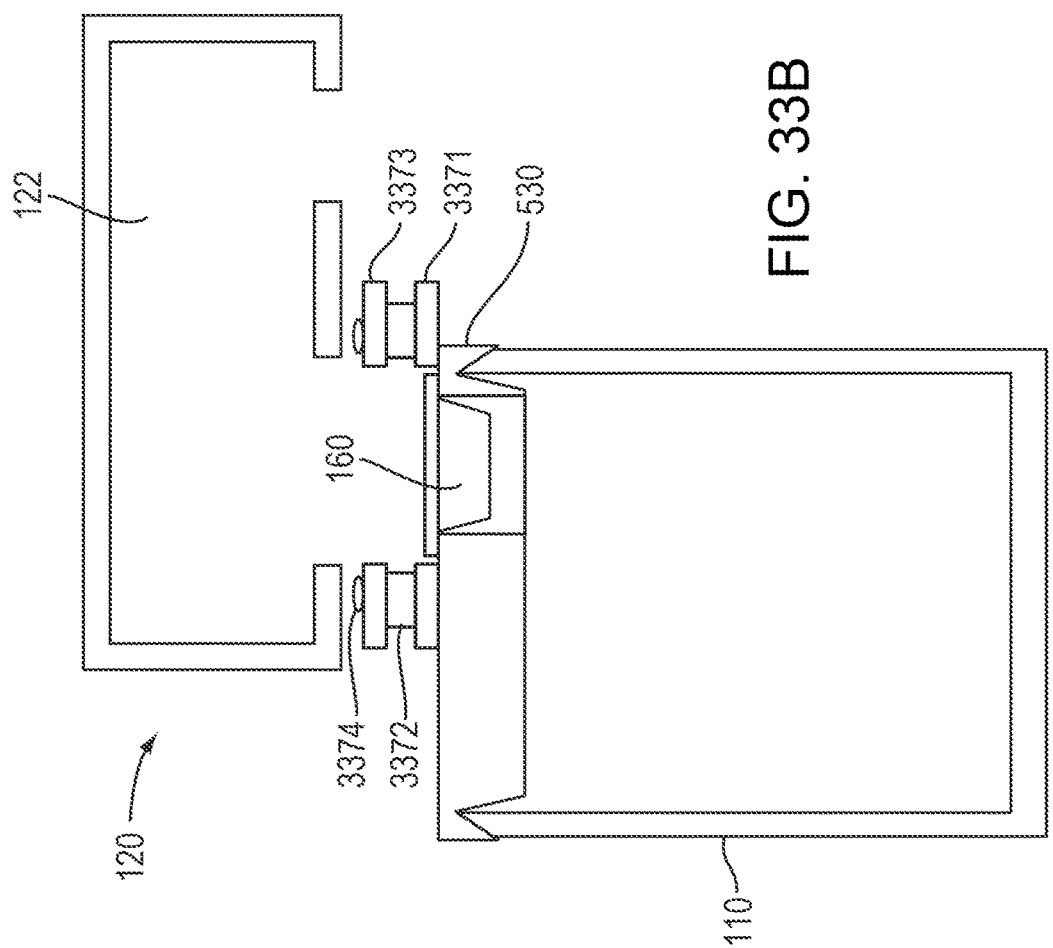
FIGS. 33A-D are illustrations of the interface between a sample handling module and a cryogenic storage vault in accordance with aspects of the disclosed embodiment.
Figure 33A:
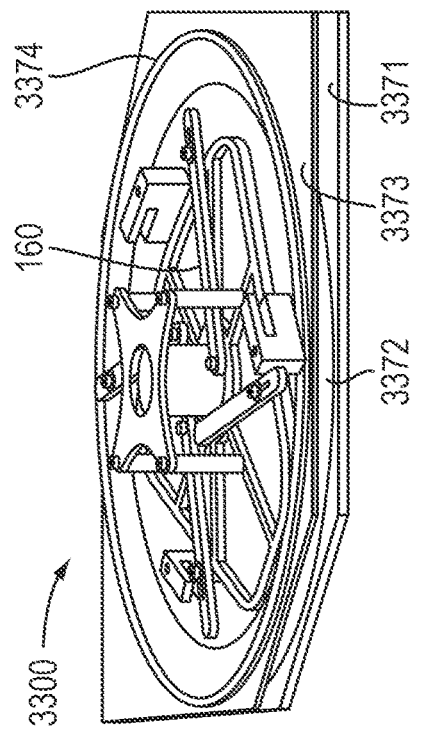

The sealed interface and assembly operation between the SHM (2320 of FIG. 23A) and the individual cryogenic storage vaults (110a-b of FIG. 23A) is now discussed. FIGS. 33A-D are illustrations of the interface between a SHM 2320 and a cryogenic storage vault 110 in accordance with aspects of the disclosed embodiment. FIG. 33A is a perspective view of a vault interface 3300. The vault interface 3300 is adapted to connect a cryogenic storage vault (110 of FIG. 23A) to a SHM (2320 of FIG. 23A). The vault interface 3300 includes a base plate 3371, a compliant ring 3372, which may be, for example, a ring of Armaflex LTD, and a top plate 3373. Referring now to FIG. 33B, a base plate 3371 of a vault interface 3000 is adapted to interface with a lid 530 of a cryogenic storage vault 110. The base plate may be the seat of the vault cover seal (2715 of FIG. 27). A top plate 3373 of a vault interface 3000 includes a seal 3374, which may be, for example, a Nitrile seal, configured to seal the top plate 3373 to a SHM 120. Together, the seal 3374 and the SHM 23020 provide an airtight seal between the vault cover 160 of the cryogenic storage vault 110 and the enclosure 122 of the SHM 2320.

Figure 33D:
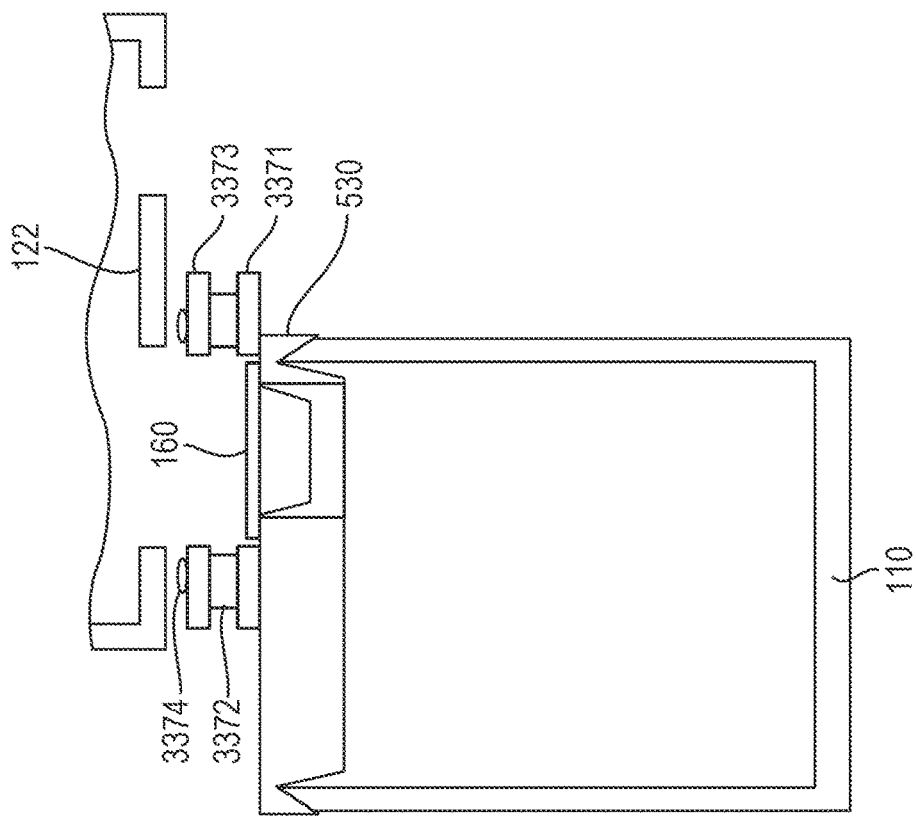
Figure 33C:
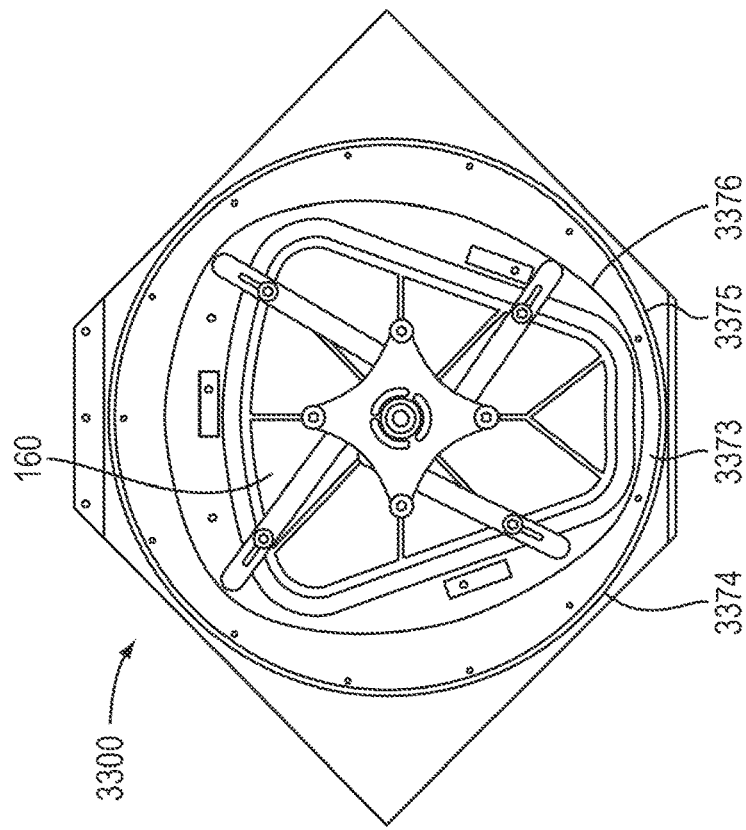

Referring now to FIGS. 33C and 33D, during assembly of the automated cryogenic storage system (2300 of FIG. 23A), the vault interface 3700 is attached to a lid 530 of a cryogenic storage vault 110 Next, the upper plate 3373 of the vault interface 3700 is screwed down to the lower plate 3371 via a series of fasteners in thru holes 3376 to compress the compliant ring 3372. With the compliant ring 3372 compressed, the Freezer, otherwise known as a cryogenic storage vault 110 is positioned under a SHM 120. Next, the upper plate 3373 is unscrewed from the lower plate 3371, allowing the compliant ring 3372 to expand and position the top plate 3373 against the SHM 120. Finally, the upper plate 3373 is fastened to the lower SHM assembly (2329 in FIG. 23B) of the SHM 120 to compress the seal 3374.

Figure 34:
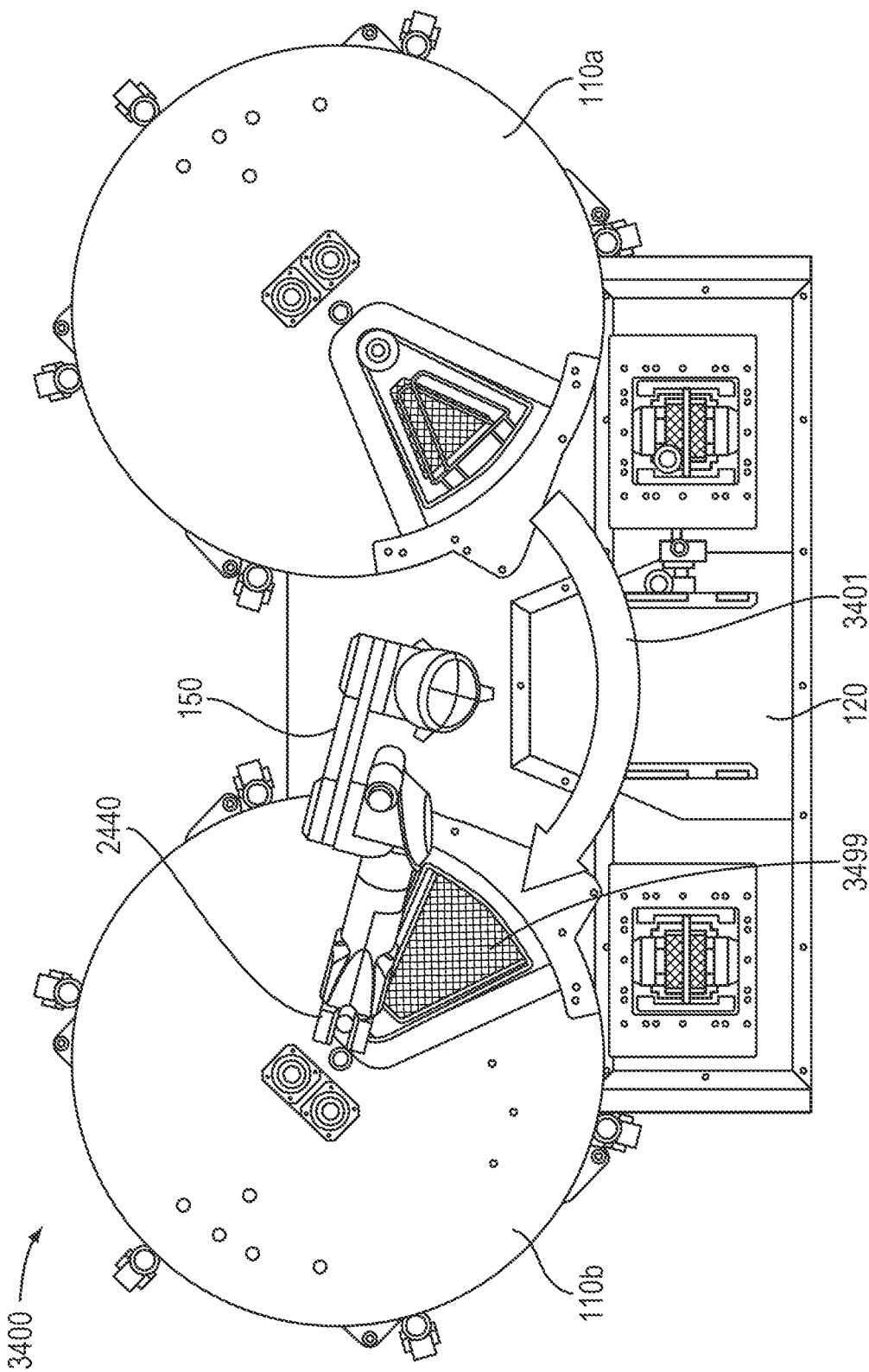
FIG. 34 is an illustration of a sample transfer robot configured to transfer a single sample tray between two cryogenic storage vaults in accordance with aspects of the disclosed embodiment.

FIGS. 34A-B are illustrations of a sample transfer robot configured to transfer a single sample tray between two cryogenic storage vaults in accordance with aspects of the disclosed embodiment. FIG. 34 shows an automated cryogenic storage system 3400 having two cryogenic storage vaults 110a-b and a SHM 122 with a sample transfer robot 150. The sample transfer robot 150 has a gripper 2440 configured to secure a tray 3499 and transferring the tray 3499 from a first cryogenic storage vault 110a to a second cryogenic storage vault 110b, as shown with arrow 3401. The threshold (2313 of FIG. 23B) is shown removed to allow individual trays to egress the cryogenic storage vaults 110a. This operation enables an entire tray to be transferred in the control environment of the SHM 120, which may be used in emergency situations or for preventative maintenance.

Figure 35:
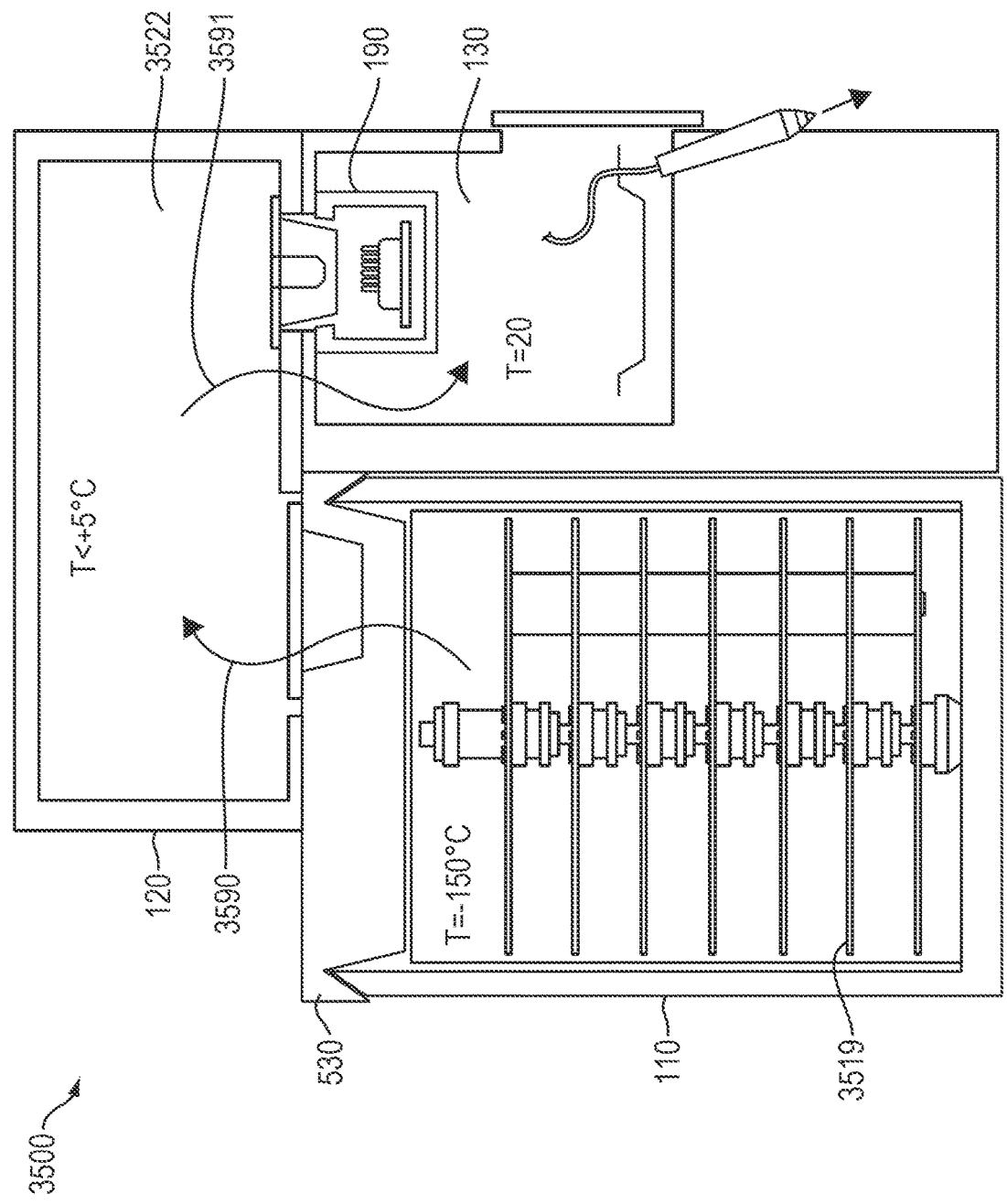
FIG. 35 is a diagram of the temperature control mechanism of an automatic cryogenic storage system having a sample handling module in accordance with aspects of the disclosed embodiment.

FIG. 35 is a diagram of the temperature and humidity control mechanism of an automatic cryogenic storage system 3500 having a SHM 120 in accordance with aspects of the disclosed embodiment. FIG. 35 shows an automated cryogenic storage system 3500 with three separate environments: An interior 3519 of a cryogenic storage vault 110, an interior 3522 of a SHM 120, and a cryodock 130 of the SHM 120. The environment in the cryogenic storage vault 3510 may be refrigerated to about −150° C. and a first flow of refrigerant 3590 from the cryogenic storage vault 3510 to the SHM 120 may maintain the interior 3522 of the SHM 120 near ambient temperature and at a suitable humidity. A second flow of refrigerant 3591 from the SHM 120 to the cryodock 130 may maintain appropriate temperature and humidity at the cryodock 130.

The refrigerant may be a cryogen such as, for example, liquid nitrogen in the cryogenic storage vault 3510, which may subsequently enter the SHM 120 as a gas (e.g., gaseous nitrogen ($N_2$)). The first flow 3590 may be the exhaust gas from a refrigeration coil in the cryogenic storage vault 3510 and may be controlled via a solenoid valve (not shown). The flows of refrigerant 3590, 3591 may also control the dew point of the interior 3522 of the SHM 120 and the cryodock 130 as low as, for example, about −100° C., such as about −75 to about −80° C. In some embodiments, the dew point of the interior 3522 of the SHM 120 and the cryodock 130 are maintained near about −50° C. such as, for example, about −40 to about −50° C. In some embodiments, the interior 3522 of the SHM 120 is maintained at a lower dew point than the cryodock 130.

Figures 36A, 36B:
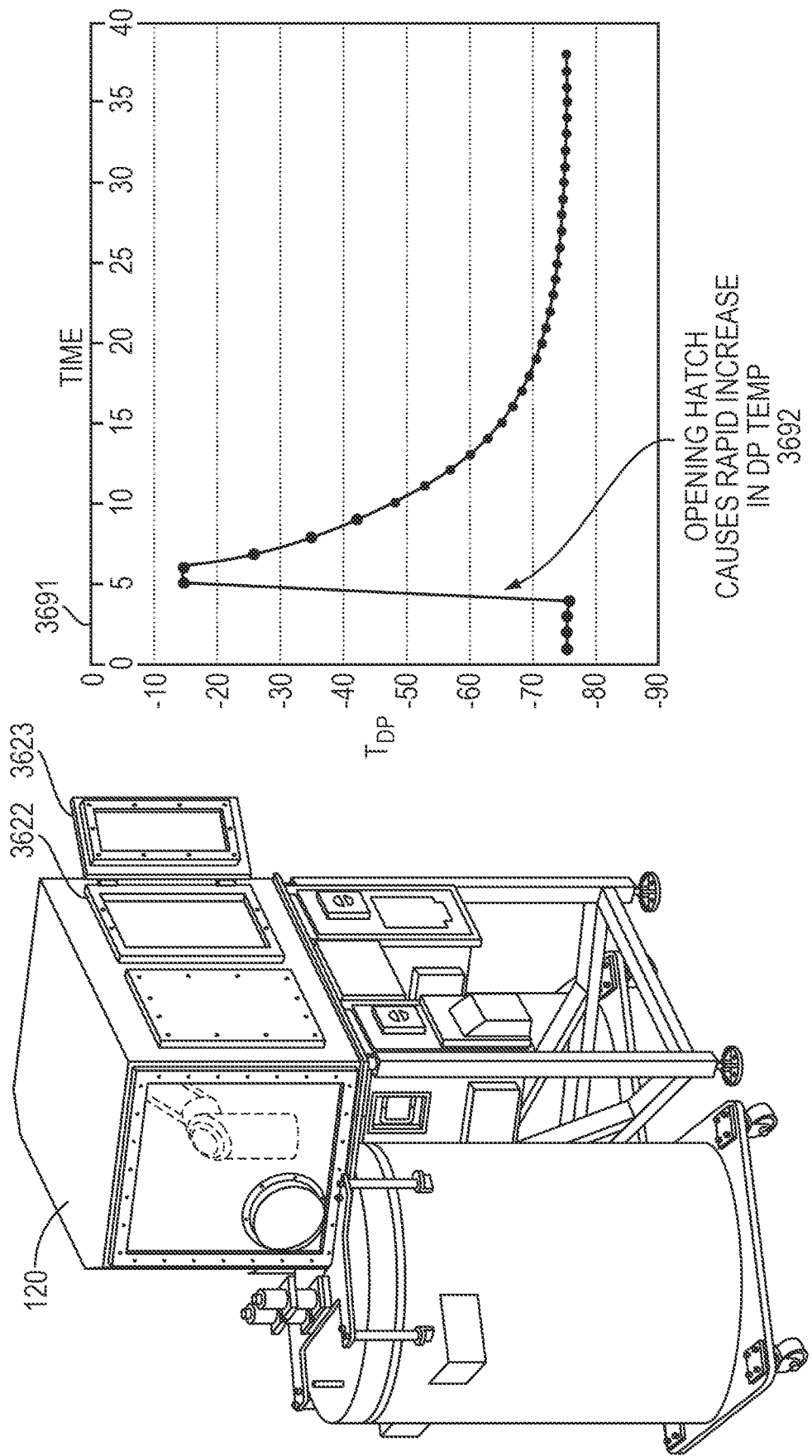
FIGS. 36A-B are illustrations of an automatic cryogenic storage system having a sample handling module with an open maintenance hatch in accordance with aspects of the disclosed embodiment.

FIG. 36A is an illustration of an automatic cryogenic storage system 3500 having a SHM 120 with an open access hatch 3622 in accordance with aspects of the disclosed embodiment. FIG. 35A shows a SHM 120 having access hatch 3622 and a corresponding door 3623. The SHM 120 may include a second access hatch. If one or both of the SHM 120 access hatches 3622 have been opened to provide access for preventative maintenance activities, the dew point temperature, indicating the level of humidity inside the SHM 120, rises significantly and rapidly as shown in FIG. 36B. FIG. 36B is a graph of the dew point change 3692 over time associated with opening and closing the access hatch 3622 of FIG. 32A at a specific time 3691. FIG. 36B shows that once the access hatch 3622 has been closed again, it takes considerably more time to reduce the dew point (humidity) to the value prior to opening the access hatch 3622.

Figure 37A:
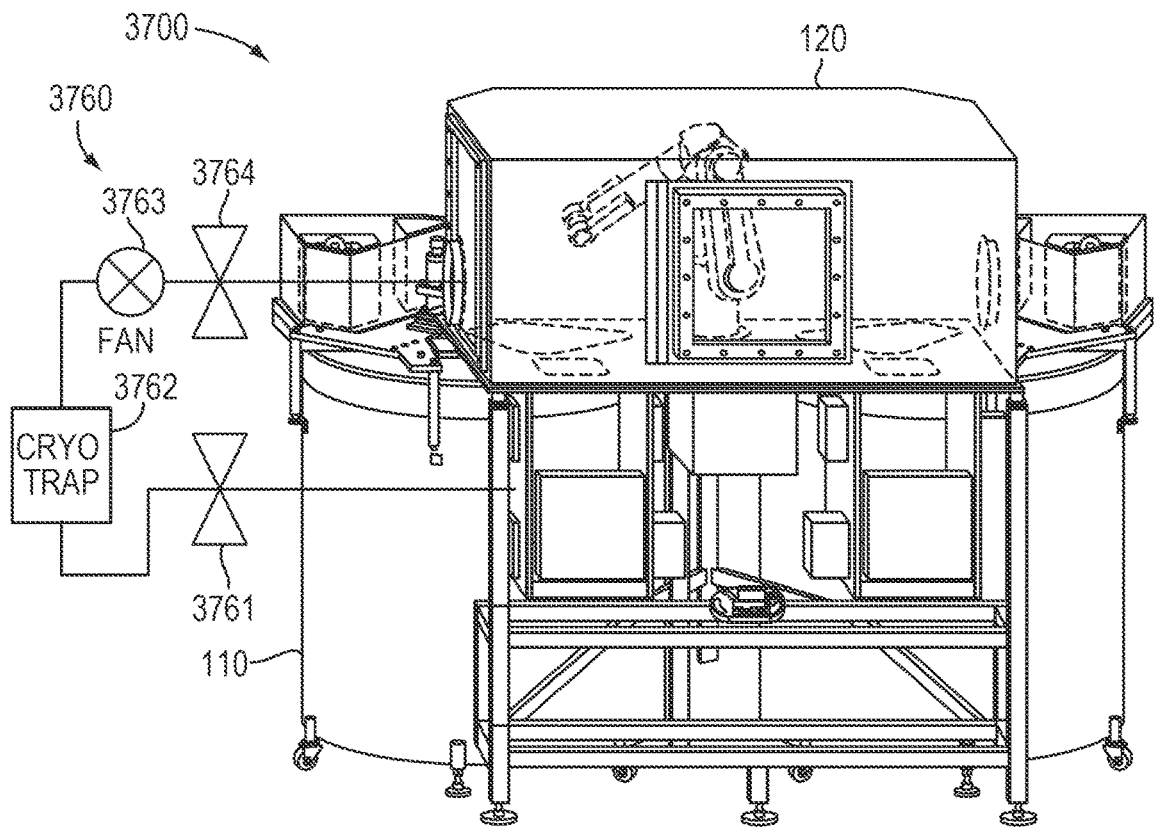
FIG. 37A is an illustration of an automatic cryogenic storage system having a sample handling device with a cryotrap configured to control humidity levels in the same handling environment in accordance with aspects of the disclosed embodiment.

FIG. 37A is an illustration of an automatic cryogenic storage system 3700 having a SHM 120 with a cryo-drying system 3762 configured to control humidity levels in the same handling environment in accordance with aspects of the disclosed embodiment. Based on the slow response of the system identified in FIG. 36B, it is desirable to identify a method to accelerate the humidity reduction process after access, in order to shorten maintenance visits. FIG. 37A shows automated cryogenic storage system 3700 including a SHM 120 and a cryogenic storage vault 110. The SHM 120 includes a cryo-drying system 3760 based on the "cryo-pumping" technology used commonly in semi-conductor manufacture. The cryo-drying system 3760 accelerates the return to acceptable level of humidity control after a disruption. The cryo-drying system 3760 comprises an output valve 3764, a fan 3763, a cryotrap grid (or plate) refrigerated to ultra-low temperatures (below −150° C.), and an input valve 3761.

In operation, after an increase in humidity inside the SHM 120 following a user access, the valves 3761,3764 are open and the fan 3763 is engaged to generate air flow from the SHM 120, through the cryotrap 3762, and back into the SHM 120. Any moisture present in the air flowing through the cryotrap 3762 is captured on a surface of the cryotrap 3762. Forcing the air flow through the cryotrap 3762 increases probability of the water molecules present in the airflow being trapped by the cold surface of the cryotrap 3762, thus accelerating the drying.

Figure 37B:
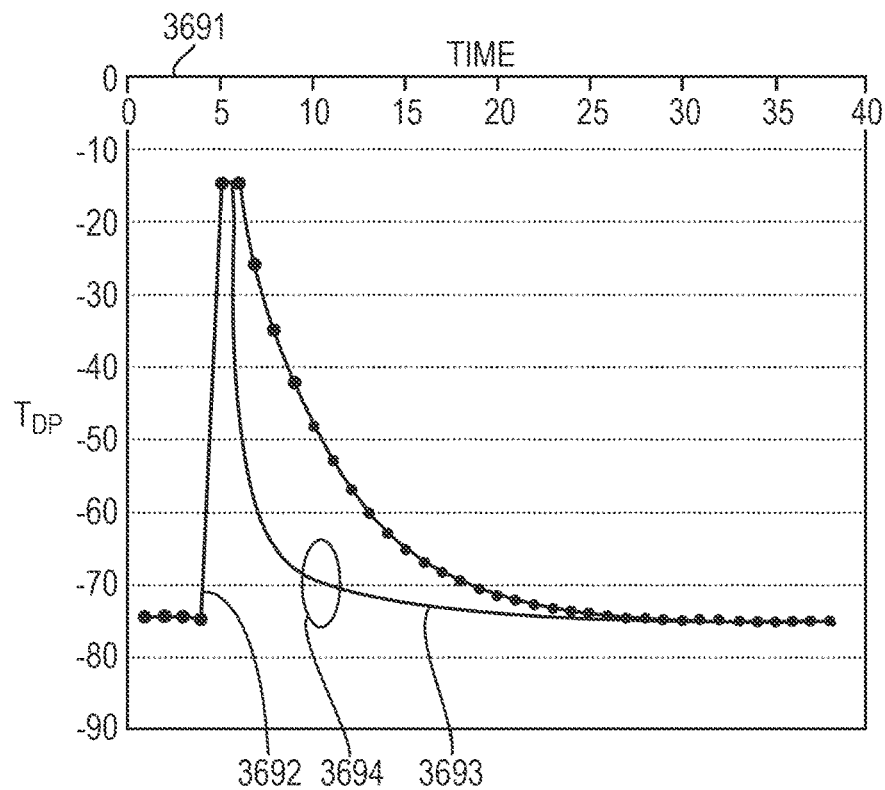
FIG. 37B is a graph of the dew point change over time associated with opening and closing the maintenance hatch of FIG. 32A and the effect of adding the cryotrap system of FIG. 33A in accordance with aspects of the disclosed embodiment.

FIG. 37B is a graph of the dew point change over time associated with opening and closing the maintenance hatch of FIG. 32A and the effect of adding the cryotrap system 3760 of FIG. 37A in accordance with aspects of the disclosed embodiment. Once the dew point in the SHM 120 is as low as desired (as highlighted on graph as 3794), the input and output valves 3761, 3764 can be shut closed and the fan 3763 turned off. With the fan 3763 off, air stops flowing through the cryotrap 3762, and the cryo-drying system 3760 is isolated from the SHM 120. Once the cryotrap 3762 has warmed up, whatever water it contains can vaporize without returning to the low-humidity environment inside the SHM 120.

The cryotrap system 3760 may be used in a variety of automated storage applications in refrigerated environments where the temperature of the plate on the cryotrap 3762 would be adjusted to suit the storage temperature. For example, in a −20° C. storage environment, the cryotrap 3762 would be set at −40° C., and in a −80° C. storage environment, it would be set significantly below −80° C. (e.g. −120° C.). While the cryo-dryer system can be used to accelerate the de-humidification after access to the sample handing module 120, it can also be used to control humidity on a permanent basis by isolating the cryotrap 3762 and releasing the captured moisture at regular intervals.

Disaster Recovery

Figure 38A:
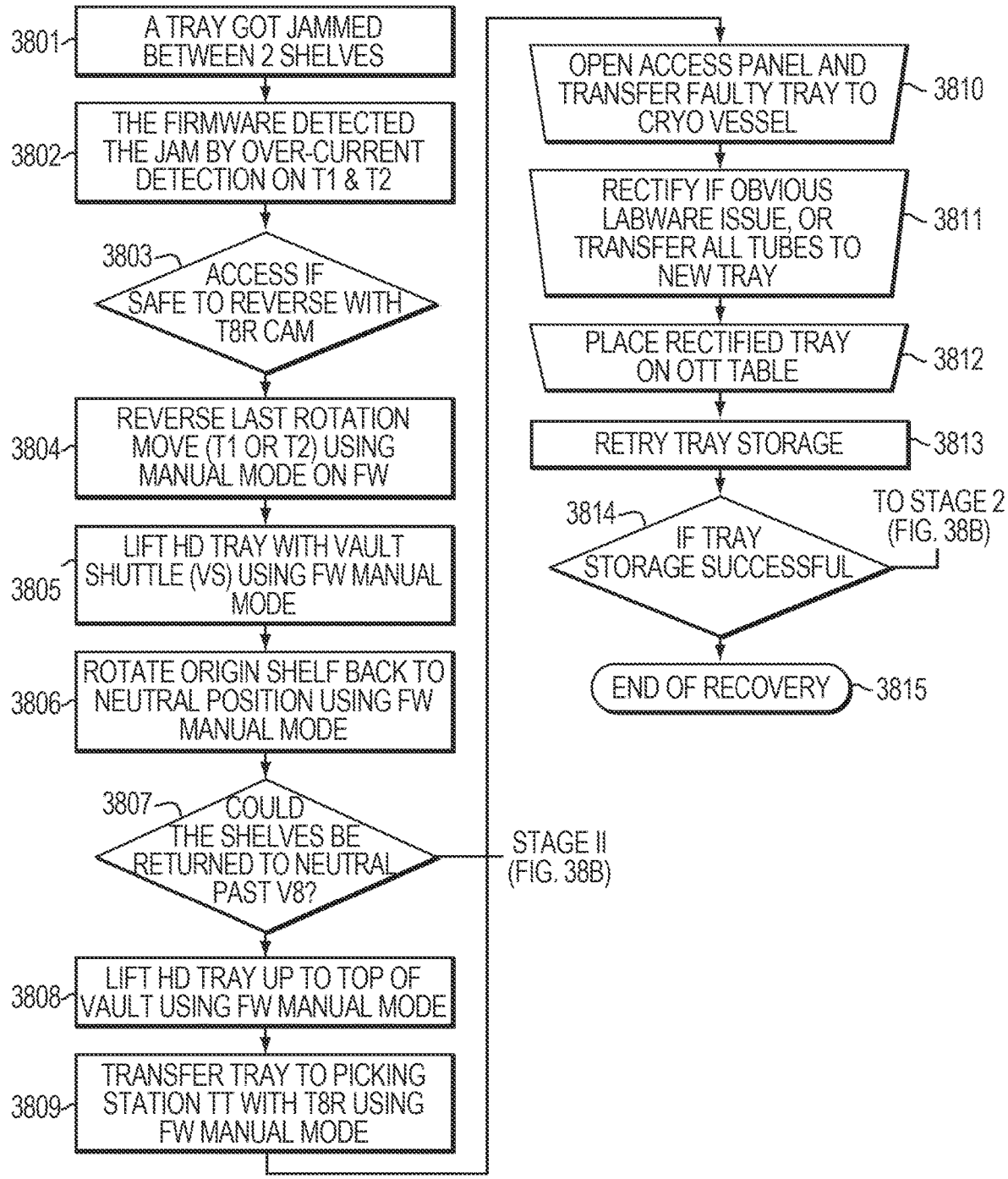
FIGS. 38A-D is a flowchart of a four-stage disaster recovery method.

FIGS. 38A-D is a flowchart of a four-stage disaster recovery method after. FIG. 38A is a flow chart of a first stage of a disaster recovery program initiated after the detection of a storage tray (910 of FIG. 9) jammed between two shelves (621, 622 of FIG. 6) of an automated cryogenic storage vault (110 of FIG. 1A)

Stage 1
  3801 A tray got jammed between two shelves.
  3802 The firmware detected the jam by over-current detection on T1 and T2.
  3803 Assess if safe to reverse with T8R cam.
  3804 Reverse last rotation move (T1 or T2) using manual mode on FW.
  3805 Lift HD tray with vault shuttle (VS) using FW manual mode
  3806 Rotate origin shelf back to neutral position using FW manual mode.
  3807 Could the shelves be returned to neutral past V8? If not, go to STAGE 2 via step 3816
  3808 Lift HD tray up to top of vault using FW manual mode
  3809 Transfer tray to picking station TT with T8R using FW manual mode.
  3810 Open access panel and transfer faulty tray to cryo vessel.
  3811 Rectify if obvious labware issue, or transfer all tubes to new tray
  3812 Place rectified ray on OTT table.
  3813 Retry tray storage
  3813 If tray storage successful, end recovery at step 3815,
  3813 If tray storage unsuccessful, go to STAGE 2.

Figure 38B:
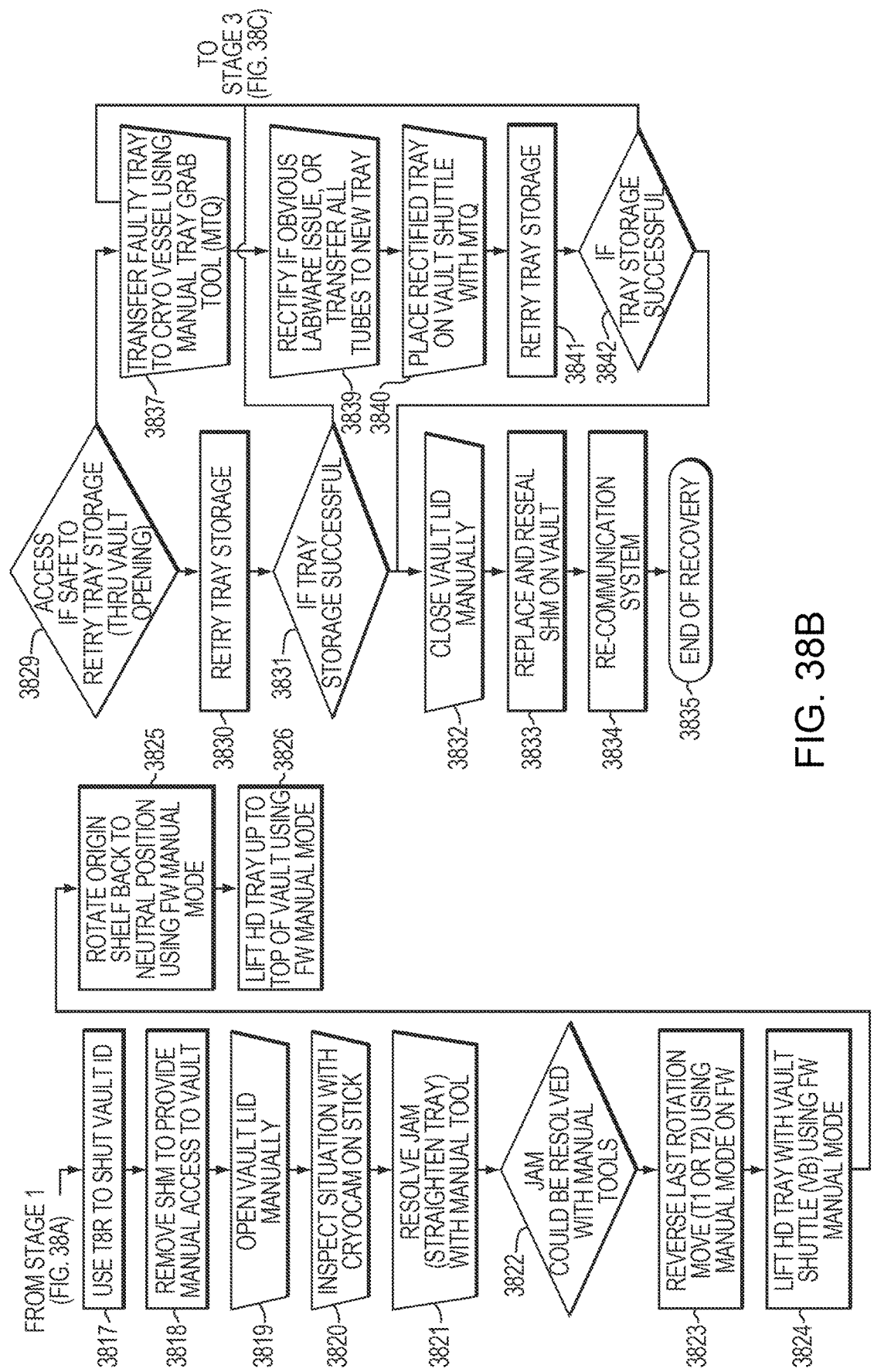

FIG. 38B is a flow chart of a second stage of a disaster recovery program initiated after determining that the jammed tray cannot be replaced successfully.

Stage 2
  3817 Use T8R to shut vault lid
  3818 Remove SHM to provide manual access to vault
  3819 Open vault lid manually
  3820 Inspect situation with cryocam on stick
  3821 Resolve jam (straighten tray) with manual tool.
  3822 If jam could be resolved with manual tools.
  3823 Reverse last rotation move (T1 or T2) using manual mode on FW.
  3824 Lift HD tray with vault shuttle (V8) using FW manual mode
  3825 Rotate origin shelf back to neutral position using FW manual mode.
  3826 Lift HD tray up to top of vault using FW manual mode
  3829 Access if safe to retry tray storage (thru vault opening), if not safe, go to step 3837.
  3830 If safe to retry tray storage, retry stray storage.
  3831 If stray storage unsuccessful, go to STAGE 3
  3832 If tray storage successful, close vault lid manually.
  3833 Replace and re-seal SHM on vault.
  3834 Re-commission system and end recovery at step 3834.
  3837 If not safe to retry tray storage, transfer faulty tray to cryo vessel using manual tray grab tool (MTQ).
  3839 Rectify if obvious labware issue, or transfer all tubes to new tray.
  3840 Place rectified tray on vault shuttle with MTQ.
  3841 Retry tray storage
  3842 If tray storage successful, go to step 3832
  3843 If tray storage unsuccessful, go to STAGE 3

Figure 38C:
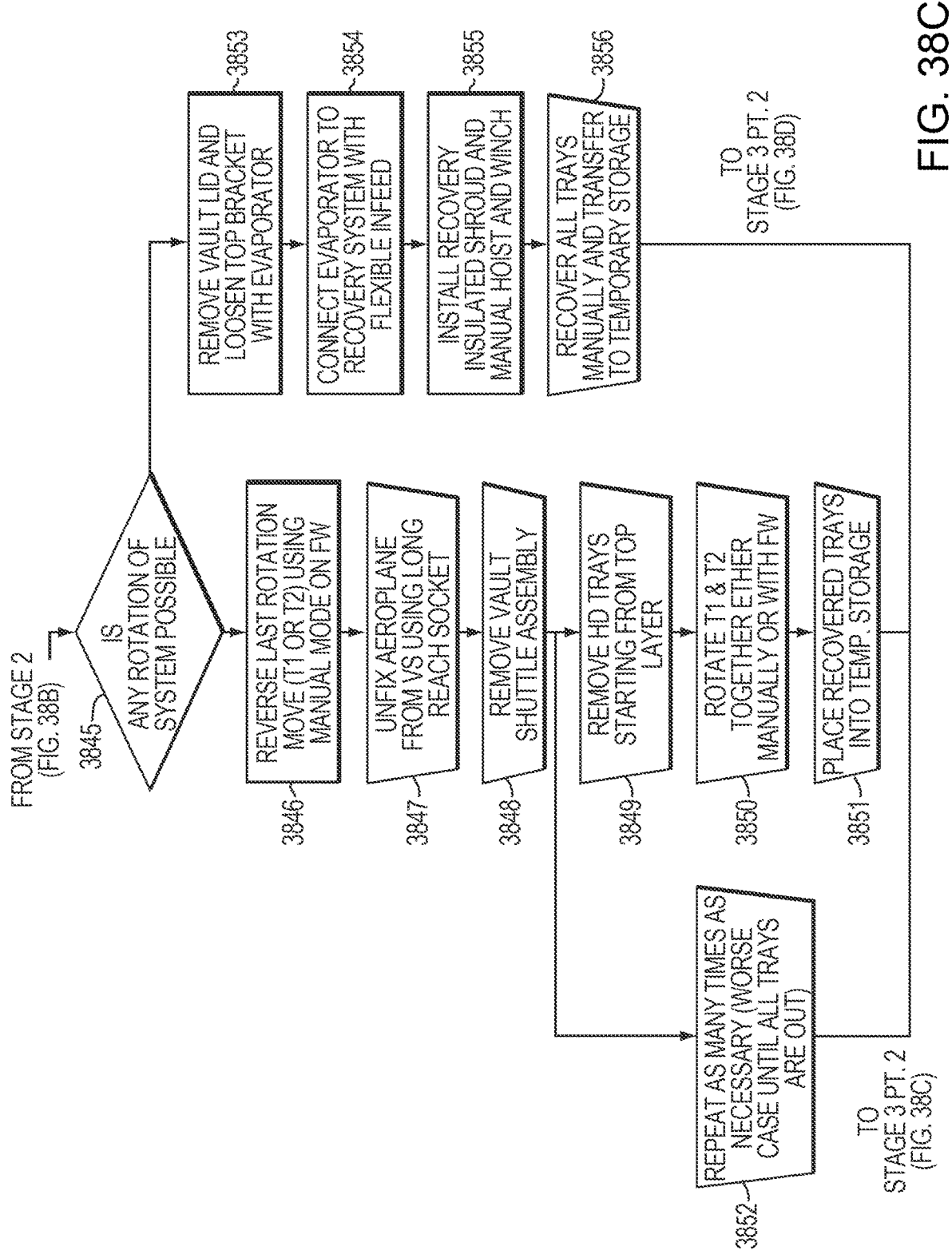

FIG. 38C is a flow chart of a third and fourth stage of a disaster recovery program initiated after determining that the jammed tray cannot be replaced successfully after manual manipulation of the tray.

Stage 3 Part 1
  3845 Is any rotation of system possible? If no, go to STAGE 4
  3846 If stage rotation of system possible, reverse last rotation move (T1 or T2) using manual mode on FW.
  3847 Unfix aeroplane from VS using long reach socket.
  3848 Remove vault shuttle assembly.
  3849 Remove HD trays starting from top layer
  3850 Rotation T1 and T2 together either manually or with FW
  3851 Place recovered trays into temporary storage.
  3852 Repeat steps 3849 to 3851 as many times as necessary, then go to STAGE 3 part 2.

Stage 4
  3853 Remove vault lid and loosen top bracket with evaporator.
  3854 Connect evaporator to recovery system with flexible infeed.
  3855 Install recovery insulated shroud and manual hoist and winch
  3856 Recover all trays manually and transfer to temporary storage, then go to STAGE 3 part 2.

Figure 38D:
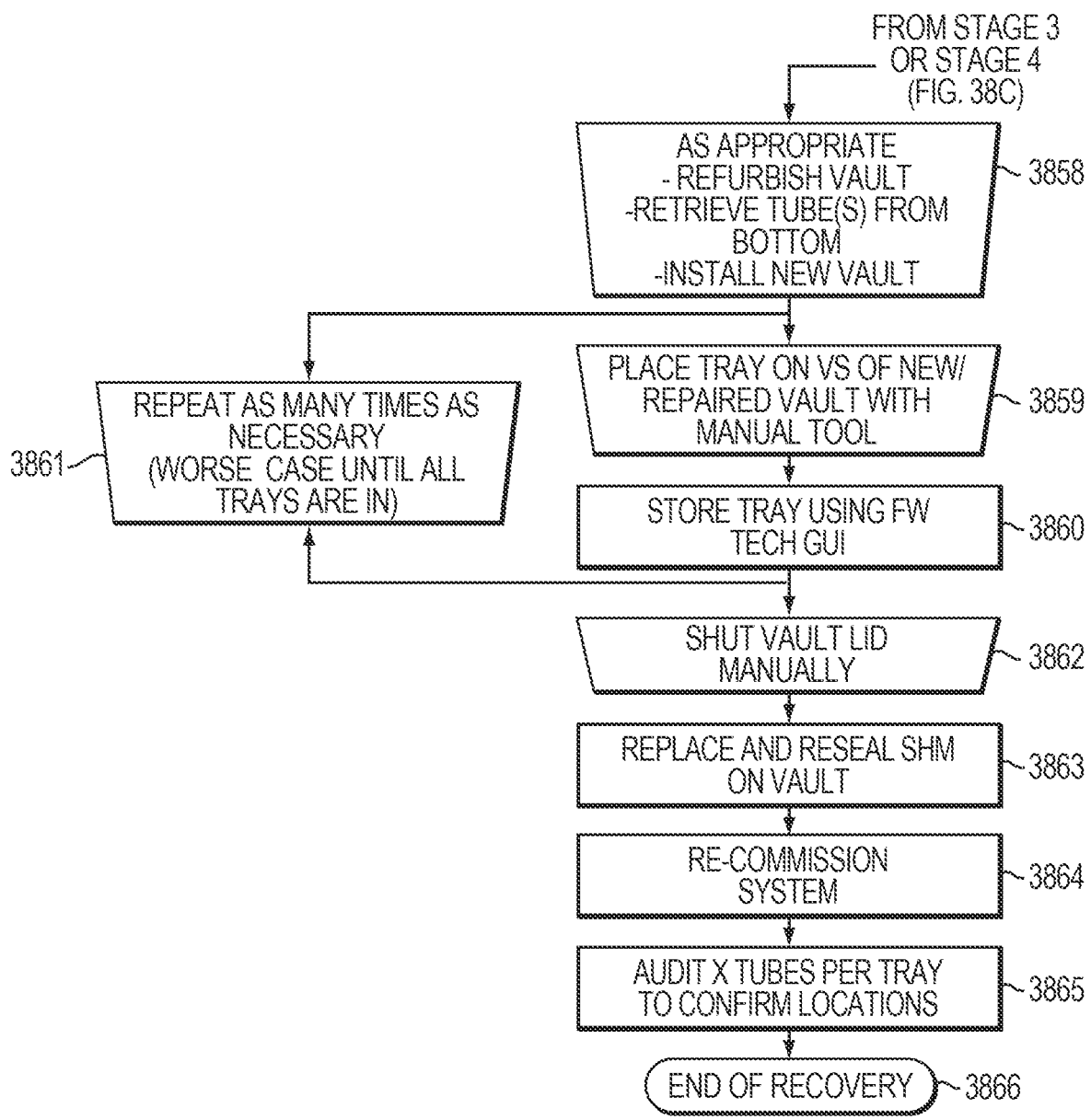

FIG. 38D is a flow chart of a final stage of a disaster recovery program initiated after opening the lid on the cryogenic storage vault to repair the cause of the jammed tray.

Stage 3 Part 2
  3858 As appropriate: (i) Refurbish vault. (ii) Retrieve tube(s) from bottom. (iii) Install new vault.
  3859 Place tray on VS of new/repaired vault with manual tool
  3860 Storage tray using FW tech GUI
  3861 Repeat steps 3859 and 3860 as many times as necessary.
  3862 Shut vault lid manually.
  3863 Replace and re-seal SHM on vault.
  3864 Re-commission system.
  3865 Audit tubes per tray to confirm locations and end recovery at step 3866.

Figure 39:
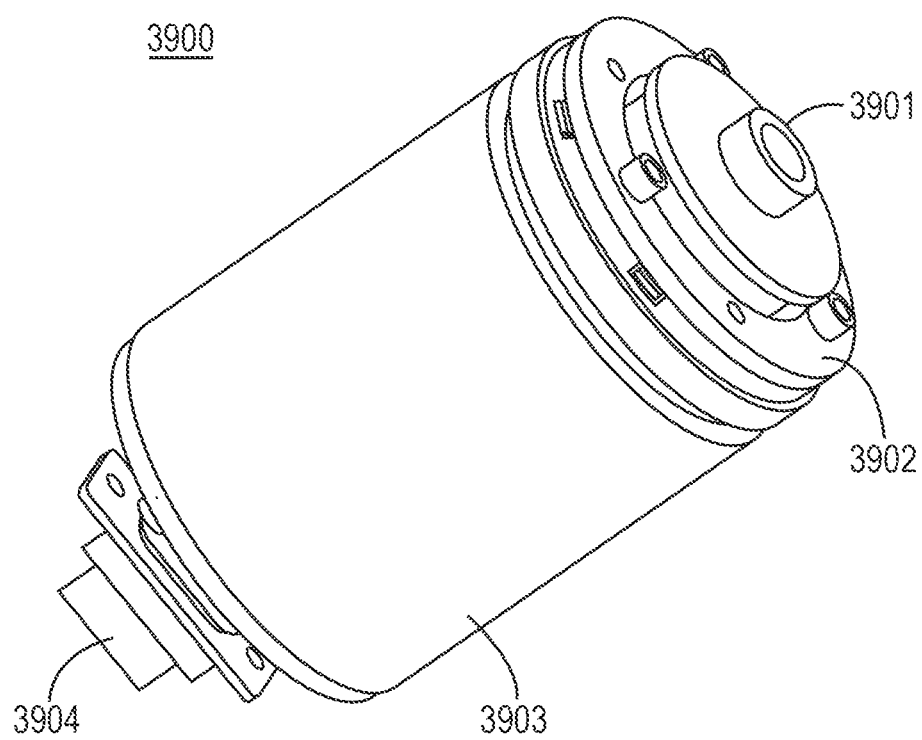
FIG. 39 is a schematic of a camera module for ultra-lower temperature environment.

FIG. 39 is a schematic of a camera module for ultra-lower temperature environment. FIG. 39 shows a camera module 3900 adapted for use in cryogenic environments. The camera module 3900 includes body 3903 and a lens 3901 and LED ring 3902 at a distal end of the camera module 3900. The body 3903 contains a camera sensor, e.g., CCD or CMOS, receiving an image circle from the camera lens 3901. The LED ring 3902 provides illumination in a direction outward from the camera lens 3901 to allow the camera module 3900 to operate in dark or lightless environments. The image sensor (not shown) sends raw image data through a data cable 3904 to image processing electronics (not show). Typically, image processing electronics are integrated with the camera body 3903, but their removal enables the camera module 3900 to operate in environments too cold for electronics to operate reliably.

Figure 40:
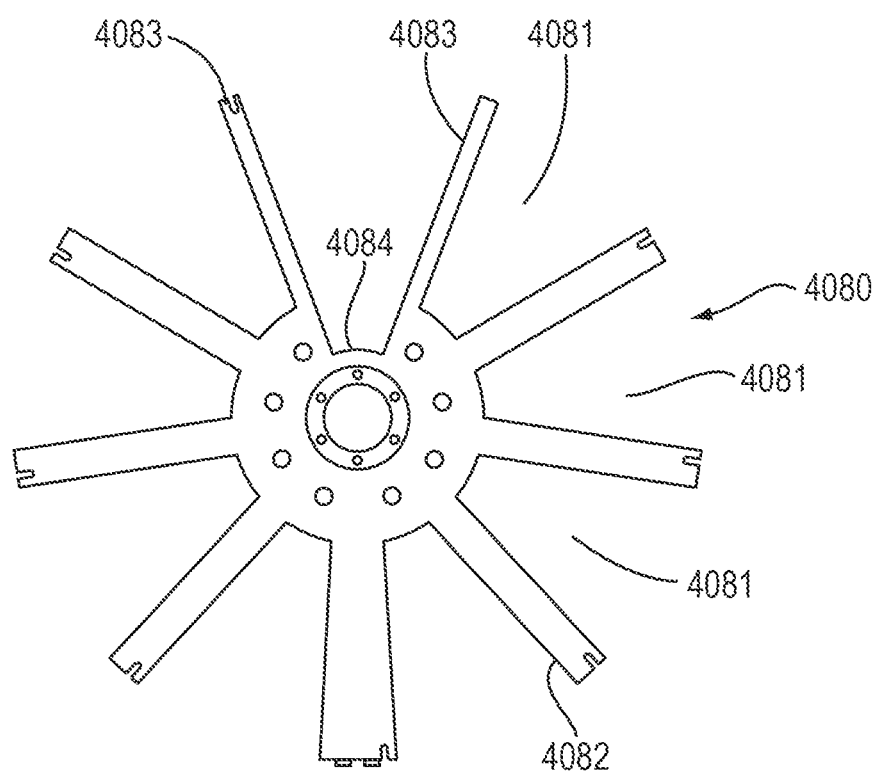
FIG. 40 is an illustration of an alternative rack embodiment.

FIG. 40 is an illustration of an alternative rack embodiment. FIG. 40 shows a star rack 4080 having a vault shuttle profiles 4084 and a plurality of tray profile 4081. The tray profiles 4081 are open at an outer end to enable an attached tray (not shown) to be removed vertically (out of the page) from the star rack 4080 by translating the tray radially away from the star rack 4080 and moving it vertically.

Figure 41:
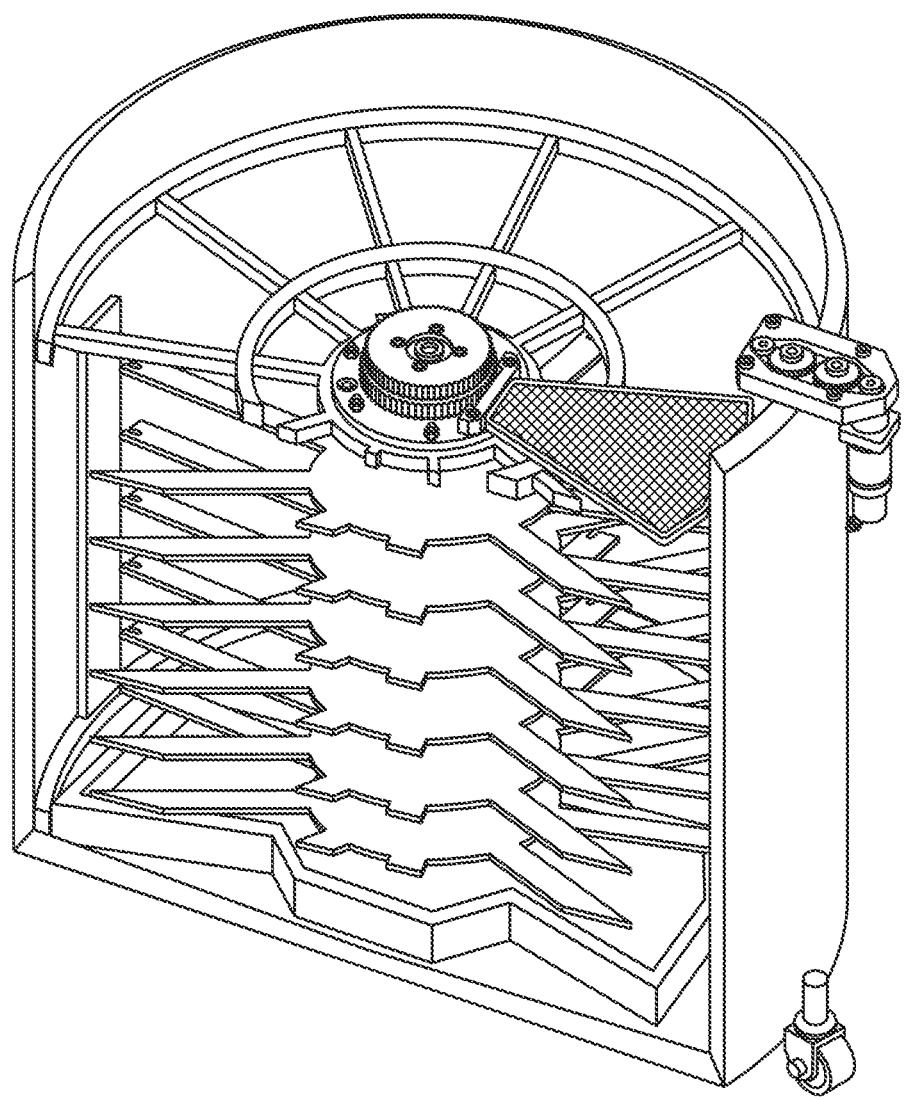
FIG. 41 is an illustration of a cryogenic storage vault having the alternative rack of FIG. 40.

FIG. 41 is an illustration of a cryogenic storage vault 110 having the alternative rack 4080 of FIG. 40.

Figure 42:
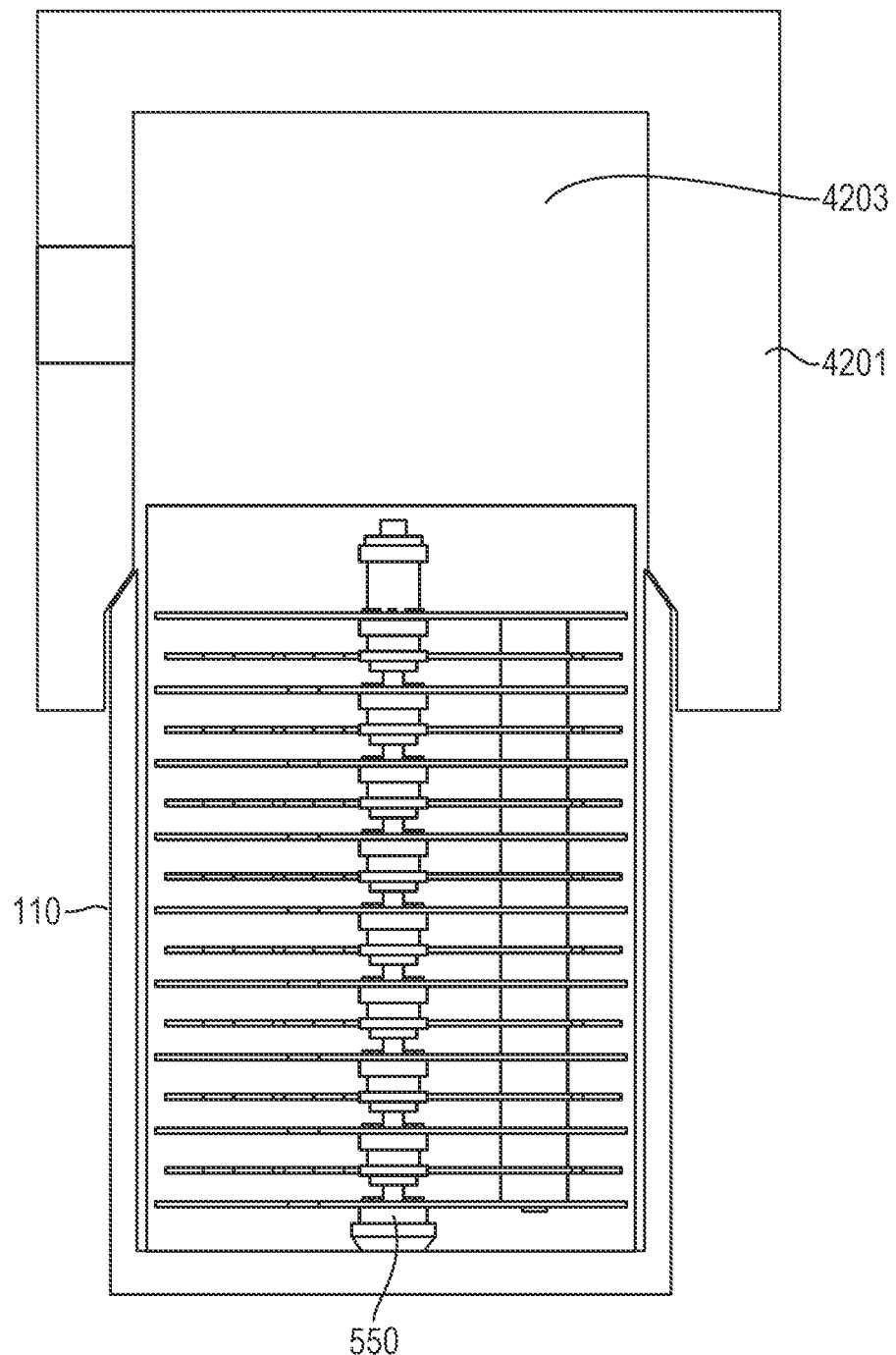
FIG. 42 is an illustration of a disaster recovery operation which includes complete disassembly of a cryogenic storage vault.

FIG. 42 is an illustration of a disaster recovery operation include complete disassembly of a cryogenic storage vault 110. FIG. 42 shows a cryogenic storage vault 110 having a spindle of racks 550 holding trays and an insulated shroud 4201 placed over the cryogenic storage vault 110. The insulated shroud 4201 forms a cavity 4203 above the cryogenic storage vault 110 to enable the spindle of racks 550 to be raised into the insulated shroud 4201 to be repaired or to service the cryogenic storage vault 110. Additionally, when the spindle of racks 550 are contained in the insulated shroud 4201, a replacement cryogenic storage vault (not shown) may be placed under the insulated shroud 4201 to transfer the spindle of racks 550 to the replacement cryogenic storage vault.

While this invention has been particularly shown and described with references to example embodiments thereof, it will be understood by those skilled in the art that various changes in form and details may be made therein without departing from the scope of the invention encompassed by the appended claims.

What is claimed is:

1. A lid for sealing a top portion of an insulated freezer, comprising:
    an upper metal skin extending to a top surface and external side surfaces of the lid, the external side surfaces extending to meet an external side wall of the insulated freezer;
    a lower metal plate extending to a bottom surface and internal side surfaces of the lid, at least a portion of the internal side surfaces contacting an inner side wall of the insulated freezer;
    an insulating foam occupying a layer between the upper metal skin and the lower metal plate; and
    at least one refrigerant coil supported by the lower metal plate, the at least one refrigerant coil being configured to expel a refrigerant gas from the at least one refrigerant coil into the insulated freezer via a plurality of orifices along a surface of the at least one refrigerant coil.

2. The lid of claim 1, wherein the upper metal skin, lower metal plate, and insulating foam are adapted to form an opening extending between the upper metal skin and the lower metal plate.

3. The lid of claim 2, wherein the opening forms a top-down shape conforming to a top-down shape of a storage tray.

4. The lid of claim 2, further comprising a threshold at a bottom portion of the opening, the threshold forming a top-down shape that frames a storage tray positioned at the bottom portion of the opening.

5. The lid of claim 1, wherein the at least one refrigerant coil includes a primary refrigerant coil and a secondary refrigerant coil.

6. The lid of claim 5, wherein the primary refrigerant coil is operable independent from of the secondary refrigerant coil.

7. The lid of claim 1, wherein the plurality of orifices are less than 1 mm in diameter.

8. The lid of claim 1, further comprising at least one solenoid valve coupled to a conduit adapted to carry refrigerant downstream from the at least one refrigerant coil.

9. The lid of claim 8, wherein the at least one solenoid valve is configured to enable a controlled amount of refrigerant gas to vent to a sample handling module.

10. A cryogenic storage vault comprising:
    an insulated freezer; and
    at least one refrigerant coil positioned at a top portion internal to the insulated freezer, the at least one refrigerant coil configured to expel a refrigerant gas into the insulated freezer via a plurality of orifices.

11. The storage vault of claim 10, further comprising at least one rack configured to store a plurality of trays, each storing a plurality of samples, the rack positioned below the at least one refrigerant coil.

12. The storage vault of claim 11, wherein the at least one refrigerant coil is further configured to expel the refrigerant gas through the rack toward a bottom portion of the insulated freezer.

13. The storage vault of claim 10, wherein the at least one refrigerant coil is further configured to expel the refrigerant gas in a manner that maintains a positive pressure within the insulated freezer.

14. The storage vault of claim 10, wherein the insulated freezer is a Dewar vessel.

15. The lid of claim 10, wherein the at least one refrigerant coil includes a primary refrigerant coil and a secondary refrigerant coil.

16. The lid of claim 15, wherein the primary refrigerant coil is operable independent from of the secondary refrigerant coil.

17. The lid of claim 15, wherein the at least one of the primary refrigerant coil and the secondary refrigerant coil is configured to expel a refrigerant gas into the insulated freezer via a plurality of orifices.

18. The lid of claim 17, wherein the plurality of orifices are less than 1 mm in diameter.

19. The lid of claim 10, further comprising at least one solenoid valve coupled to a conduit adapted to carry refrigerant downstream from the at least one refrigerant coil.

20. The lid of claim 19, wherein the at least one solenoid valve is configured to enable a controlled amount of refrigerant gas to vent to a sample handling module.

* * * * *